US008524227B2

(12) United States Patent
Xu et al.

(10) Patent No.: US 8,524,227 B2
(45) Date of Patent: *Sep. 3, 2013

(54) ANTI-IL-TIF ANTIBODIES

(75) Inventors: Wenfeng Xu, Mukilteo, WA (US);
Wayne R. Kindsvogel, Seattle, WA (US); Steven D. Hughes, Kenmore, WA (US); Yasmin A. Chandrasekher, Mercer Island, WA (US)

(73) Assignee: ZymoGenetics, Inc., Seattle, WA (US)

( * ) Notice: Subject to any disclaimer, the term of this patent is extended or adjusted under 35 U.S.C. 154(b) by 617 days.

This patent is subject to a terminal disclaimer.

(21) Appl. No.: 12/732,116

(22) Filed: Mar. 25, 2010

(65) Prior Publication Data

US 2012/0189628 A1 Jul. 26, 2012

Related U.S. Application Data

(62) Division of application No. 11/829,765, filed on Jul. 27, 2007, now Pat. No. 7,718,172, which is a division of application No. 10/395,741, filed on Mar. 24, 2003, now Pat. No. 7,265,211.

(60) Provisional application No. 60/366,842, filed on Mar. 22, 2002.

(51) Int. Cl.
*A61K 39/395* (2006.01)
*C07K 16/22* (2006.01)
*C07K 16/24* (2006.01)
*C07K 14/54* (2006.01)
*C12P 21/08* (2006.01)

(52) U.S. Cl.
USPC .......... 424/130.1; 424/133.1; 424/134.1; 424/141.1; 424/145.1; 424/178.1; 530/351; 530/387.1; 530/387.3; 530/388.1; 530/388.23; 530/391.3; 530/391.7

(58) Field of Classification Search
None
See application file for complete search history.

(56) References Cited

U.S. PATENT DOCUMENTS

| | | | |
|---|---|---|---|
| 4,443,549 A | 4/1984 | Sadowski | |
| 5,397,569 A | 3/1995 | Whitfill et al. | |
| 5,488,032 A | 1/1996 | Dower et al. | |
| 5,965,704 A | 10/1999 | Lok et al. | |
| 6,013,503 A | 1/2000 | Lok et al. | |
| 6,274,710 B1 | 8/2001 | Dumoutier et al. | |
| 6,551,799 B2 | 4/2003 | Gurney et al. | |
| 7,265,211 B2 | 9/2007 | Xu et al. | |
| 7,563,568 B2 | 7/2009 | Presnell et al. | |
| 7,674,461 B2 | 3/2010 | Xu et al. | |
| 8,124,077 B2 * | 2/2012 | Presnell et al. | 424/130.1 |
| 2003/0022827 A1 | 1/2003 | Weiss et al. | |
| 2003/0170823 A1 | 9/2003 | Presnell et al. | |
| 2004/0152125 A1 | 8/2004 | Presnell et al. | |
| 2009/0022723 A1 | 1/2009 | Xu et al. | |

FOREIGN PATENT DOCUMENTS

| | | |
|---|---|---|
| EP | 1191035 | 3/2002 |
| WO | 98/02542 A1 | 1/1998 |
| WO | WO 98/37193 | 8/1998 |
| WO | WO 99/07848 | 2/1999 |
| WO | WO 00/24758 | 5/2000 |
| WO | WO 00/39161 | 7/2000 |
| WO | WO 00/65027 | 11/2000 |
| WO | WO 00/70049 | 11/2000 |
| WO | WO 00/73457 | 12/2000 |
| WO | WO 00/77037 | 12/2000 |
| WO | WO 01/16318 | 3/2001 |
| WO | WO 01/36467 | 5/2001 |
| WO | WO 01/40467 | 6/2001 |
| WO | WO 01/46422 | 6/2001 |
| WO | WO 01/98342 | 12/2001 |
| WO | WO 02/10393 | 2/2002 |
| WO | WO 02/16611 | 2/2002 |
| WO | WO 02/20569 | 3/2002 |
| WO | WO 02/024912 | 3/2002 |
| WO | WO 02/066647 | 8/2002 |
| WO | WO 02/068476 | 9/2002 |
| WO | WO 02/072607 | 9/2002 |
| WO | WO 03/035096 | 5/2003 |

OTHER PUBLICATIONS

Colcher et al. Effects of genetic engineering on the pharmacokinetics of antibodies. Quarterly J Nuc Med 43(2): 132-139, 1999.*
Dumoutier et al., "Cutting Edge: STAT Activation by IL-19, IL-20 and mda-7 Through IL-20 Receptor Complexes of Two Types,"*J. Immunol.* 167:3545-3549, 2001.
Dumoutier, L et al.,"Cloning and Characterization of IL-22 Binding Protein, a Natural Antagonist of IL-10-Related T Cell-Derived Inducible Factor/IL-22," *J. Immunol.* 166:7090-7095, 2001.
Kotenko et al., "Identification, Cloning, and Characterization of a Novel Soluble Receptor That Binds IL-22 and Neutralizes Its Activity," *J. Immunol.* 166:7096-7013, 2001.
Xu et al., "A soluble class II cytokine receptor, IL-22RA2, is a naturally occurring IL-22 antagonist," *Proc. Nat. Acad. Sci.* 98:9511-9516, 2001.
Gruenberg et al., "A novel, soluble homologue of the human IL-10 receptor with preferential expression in placenta," *Genes and Immunity* 2:329-334, 2001.
Xie et al., "Interleukin (IL)-22, a Novel Human Cytokine That Signals through the Interferon Receptor-related Proteins CRF2-4 and IL-22R," *J. Biol. Chem.* 275(40):31335-31339, 2000.
Dumoutier et al. "Human interleukin-10-related T cell-derived inducible factor: Molecular cloning and functional characterization as an hepatocyte-stimulating factor," *Proc. Nat. Acad. Sci.* 97(18):10144-10149, 2000.

(Continued)

*Primary Examiner* — Bridget E Bunner
(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to blocking the activity of IL-TIF polypeptide molecules. IL-TIF is a cytokine involved in inflammatory processes and human disease. The present invention includes anti-IL-TIF antibodies and binding partners, as well as methods for antagonizing IL-TIF using such antibodies and binding partners in IL-TIF-related human inflammatory diseases, amongst other uses disclosed.

16 Claims, 1 Drawing Sheet

(56) References Cited

OTHER PUBLICATIONS

Dumoutier et al., IL-TIF/IL-22: genomic organization and mapping of the human and mouse genes, *Genes and Immunity*. 1:488-494, 2000.

Xu, X. et al., EMBL Database, Chinese National Human Genome Center at Shanghai, Oct. 5, 2000: AV714177.

Incyte Pharmaceuticals, Inc. clone, 1999: SHLW01158999.

Wells, "Additivity of Mutational Effects in Proteins," *Biochemistry* 29(37):8509-8517, 1990.

Liu et al., "Expression Cloning and Characterization of a Human IL-10 Receptor," *J. Immunol.* 152:1821-1829, 1994.

Blumberg et al., "Interleukin 20: Discovery, Receptor Identification, and Role in Epidermal Function," *Cell* 104:9-19, 2001.

Zhang et al., "Identification, Purification, and Characterization of a Soluble Interleukin (IL)-13-binding Protein," *J. Biochem*. 272:9474-9480, 1997.

Kotenko et al., "Jak-Stat signal transduction pathway through the eyes of cytokine class II receptor complexes," *Oncogene* 19:2557-2565, 2000.

Kotenko et al., "Identification of the Functional Interleukin-22 (IL-22) Receptor Complex," *J. Biochem*. 276(4):2725-2732, 2001.

Wei et al., "Cloning and characterization of mouse IL-22 binding protein," *Genes and Immunity* 34:204-211, 2003.

Bork et al., "Go hunting in sequence databases but watch out for the traps," *TIG* 12(10):425-0426, 1996.

Bork, "Powers and Pitfalls in Sequence Analysis: The 70% Hurdle," *Genome Research* 10:398-400, 2000.

Sempowski et al., "Subsets of Murine Lung Fibroblasts Express Membrane-Bound and Soluble IL-4 Receptors," *J. Immonol*. 152:3606-3614, 1994.

Bork et al., "Predicting functions from protein sequences—where are the bottlenecks," *Nature Genetics* 18:313-318, 1998.

Parrish-Novak et al., "Interleukins 19, 20, and 24 Signal through Two Distinct Receptor Complexes," *J. Biochem* 277(49):47517-47523, 2002.

Uhlar et al., "Serum amyloid A, the major vertebrate acute-phase reactant," *Eur. J. Biochem*. 265:501-523, 1999.

Hillier et al., GenBank Accession No. AA132964, Nov. 27, 1996.

Hillier et al., GenBank Accession No. T70354, Mar. 7, 1995.

Hillier et al., GenBank Accession No. T70439, Mar. 7, 1995.

Muzny et al., EMBL Database, AC007458, Jan. 23, 2003.

Moore, "G. Genetically engineered antibodies," *Clin. Chem*. 35(9):1849-1853, 1989.

Ballow et al., "Immunopharmacology, immunomodulation and immunotherapy," *J. Am. Med. Assoc*. 278(22):2008-2017, 1997.

Dillman et al., "Monoclonal antibodies in the treatment of malignancy: basic concepts and recent developments," *Cancer Invest*. 19(8):833-841, 2001.

Dumoutier et al., "Cloning and Characterization of IL-10-Related T Cell-Derived Inducible Factor (IL-TIF), a Novel Cytokine Structurally Related to IL-10 and Inducible by IL-9," *Journal of Immunology* 164: 1814-1819, 2000.

Bleicher et al., "Crystal structure of IL-22/IL-22R1 complex and its implications for the IL-22 signaling mechanism," FEBS Letters 582(20): 2985-2992, 2008.

Presnell et al., U.S. Appl. No. 12/499,636, filed Jul. 8, 2009.

Presnell et al., U.S. Appl. No. 09/471,767, filed Dec. 23, 1999.

Klenk, Hans-Peter et al., "The complete genome sequence of the hyperthermophilic, sulphate-reducing archaeon *Archaeoglobus fulgidus*," Nature, vol. 390:364-370 (1970).

International Search Report for Application No. PCT/US00/35308, 3 pages, dated Apr. 11, 2001.

International Preliminary Examination Report, for Application No. PCT/US00/35308, 18 pages, dated Mar. 27, 2002.

U.S. Appl. No. 13/342,675, Scott R. Presnell, filed Jan. 3, 2012, mailed Dec. 7, 2012.

\* cited by examiner

```
                        10        20        30        40
hIL-TIF         MGTLATSCLLLALLVQGGAAAPISSHCRLDKSNFQQPYITNRTFMLA
                ::::::::::::::::::::::::::::::::::::::::::::::
mIL-TIF         X:::::::::::::::::::::::::::::::::::::::::::::
       MAVLQKSMSFSLMGTLAASCLLLIALWAQEANALPVNTRCKLEVSNFQQPYIVNRTFMLA
                        10        20        30        40        50        60

50        60        70        80        90       100
hIL-TIF         KEASLADNNTDVRLIGEKLFHGVSMSERCYLMKQVLNFTLEEVLFPQSDRFQPYMQEVVP
                ::::::::::::::::::::::::::::::::::::::::::::::::::::::::::
mIL-TIF         KEASLADNNTDVRLIGEKLFRGVNAKDQCYLMKQVLNFTLEDVLLPQSDRFQPYMQEVVP
                        70        80        90       100       110       120

110       120       130       140       150       160
hIL-TIF         FLARLSNRLSTCHIEGDDLHIQRNVQKLKDTVKKLGESGEIKAIGELDLLFMSLRNACI
                :::::::::::::::::::::::::::::::::::::::::::::::::::::::X.
mIL-TIF         FLTKLSNQLSSCHISGDDQNIQKNVRRLKETVKKLGESGEIKAIGELDLLFMSLRNACV
                       130       140       150       160       170
```

ANTI-IL-TIF ANTIBODIES

REFERENCE TO RELATED APPLICATIONS

This application is a divisional of U.S. application Ser. No. 11/829,765, filed Jul. 27, 2007, now U.S. Pat. No. 7,718,172, which is a divisional of U.S. application Ser. No. 10/395,741, filed Mar. 24, 2003, now U.S. Pat. No. 7,265,211, which claims the benefit of U.S. Provisional Application Serial No. 60/366,842, filed Mar. 22, 2002, all of which are herein incorporated by reference. Under 35 U.S.C. §119(e)(1), this application claims benefit of said Provisional Application.

BACKGROUND OF THE INVENTION

Cytokines generally stimulate proliferation or differentiation of cells of the hematopoietic lineage or participate in the immune and inflammatory response mechanisms of the body.

Examples of cytokines that affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The interleukins are a family of cytokines that mediate immunological responses, including inflammation. The interleukins mediate a variety of inflammatory pathologies. Central to an immune response is the T cell, which produce many cytokines and adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Moreover, cytokine-influenced inflammation is manifested in acute disease as well as chronic disease in humans. For example, enhanced inflammatory states are evident in toxic shock syndrome, sepsis, endotoxemia, inflammatory bowel disease (IBD), psoriasis, asthma, Chron's Disease, rheumatoid arthritis as well as many other diseases. In many instances the chronic inflammatory state is directly involved in the debilitating aspects of such diseases, prolonging the disease and resulting in increased damage to chronically inflamed tissues. As such anti-inflammatory agents are sought.

The demonstrated in vivo activities of the cytokine family illustrates the enormous clinical potential of, and need for, other cytokines, cytokine agonists, and cytokine antagonists. For example, demonstrated in vivo activities of the pro-inflammatory cytokine family illustrates the enormous clinical potential of, and need for antagonists of pro-inflammatory molecules. The present invention addresses these needs by providing antibodies to a pro-inflammatory cytokine, IL-TIF, including neutralizing anti-human IL-TIF antibodies, as well as providing uses for anti-IL-TIF antibodies in inflammatory disease, as well as related compositions and methods.

BRIEF DESCRIPTION OF THE DRAWING

FIG. 1 is a multiple alignment of human IL-TIF polypeptide (hIL-TIF) (SEQ ID NO:3), and mouse IL-TIF polypeptide (mIL-TIF)(SEQ ID NO:38). The":" in the figure indicates amino acids that are identical between the mouse and human sequences, and the "." in the figure indicates amino acids that are conserved substitutions. There is 78.4% identity between the human and mouse sequences over the entire sequence (167 amino acid overlap).

DESCRIPTION OF THE INVENTION

The present invention provides such polypeptides for these and other uses that should be apparent to those skilled in the art from the teachings herein.

Within one aspect, the present invention provides a method of producing an antibody to a polypeptide comprising: inoculating an animal with a polypeptide selected from the group consisting of: (a) a polypeptide consisting of 30 to 144 amino acids, wherein the polypeptide is identical to a contiguous sequence of amino acids in SEQ ID NO:3 from amino acid number 23 (Gly) to amino acid number 779 (Thr); (b) a polypeptide consisting of the amino acid sequence of SEQ ID NO:3 from amino acid number 23 (Pro), to amino acid number 167 (Ile); (c) a polypeptide consisting of the amino acid sequence of SEQ ID NO:3 from amino acid number 1 (Met), to amino acid number 167 (Ile); (d) a polypeptide consisting of the amino acid sequence of SEQ ID NO:2 from amino acid number 1 (Met), to amino acid number 179 (Ile); (e) a polypeptide consisting of the amino acid sequence of SEQ ID NO:3 from amino acid number 29 (Arg) to amino acid number 34 (Asn); (f) a polypeptide consisting of the amino acid sequence of SEQ ID NO:3 from amino acid number 121 (His) to amino acid number 126 (Asp); (g) a polypeptide consisting of the amino acid sequence of SEQ ID NO:3 from amino acid number 134 (Gln) to amino acid number 139 (Thr); (h) a polypeptide consisting of the amino acid sequence of SEQ ID NO:3 from amino acid number 137 (Lys) to amino acid number 142 (Lys); (i) a polypeptide consisting of the amino acid sequence of SEQ ID NO:3 from amino acid number 145 (Glu) to amino acid number 150 (Lys); (j) a polypeptide consisting of the amino acid sequence of SEQ ID NO:3 from amino acid number 41 (Thr), to amino acid number 53 (Leu); (k) a polypeptide consisting of the amino acid sequence of SEQ ID NO:3 from amino acid number 80 (Met) to amino acid number 91 (Val); (l) a polypeptide consisting of the amino acid sequence of SEQ ID NO:3 from amino acid number 103 (Met) to amino acid number 116 (Arg); (m) a polypeptide consisting of the amino acid sequence of SEQ ID NO:3 from amino acid number 149 (Ile) to amino acid number 162 (Leu); and (n) a polypeptide consisting of an epitope of amino acid sequence of SEQ ID NO:3 as predicted from a Jameson-Wolf plot; and wherein the polypeptide elicits an immune response in the animal to produce the antibody; and isolating the antibody from the animal; and wherein the antibody specifically binds to a polypeptide of SEQ ID NO:2 or SEQ ID NO:3; and inhibits the pro-inflammatory activity of the polypeptide of SEQ ID NO:2 or SEQ ID NO:3.

Within another aspect, the present invention provides an antibody produced by the method as disclosed above, which specifically binds to a polypeptide of SEQ ID NO:2 or SEQ ID NO:3. In one embodiment, the antibody is as disclosed above, wherein the antibody is selected from the group consisting of: (a) polyclonal antibody, (b) murine monoclonal antibody, (c) humanized antibody derived from (b), (d) an antibody fragment, and (e) human monoclonal antibody.

Within another aspect, the present invention provides an antibody or antibody fragment that specifically binds to a polypeptide of comprising a sequence of amino acid residues selected from the group consisting of: (a) the amino acid sequence as shown in SEQ ID NO:3 from amino acid number 23 (Pro), to amino acid number 167 (Ile); (b) the amino acid sequence as shown in SEQ ID NO:3 from amino acid number 1 (Met), to amino acid number 167 (Ile); and (c) the amino acid sequence as shown in SEQ ID NO:2 from amino acid number 1 (Met), to amino acid number 179 (Ile); and inhibits the pro-inflammatory activity of the polypeptide of SEQ ID NO:2 or SEQ ID NO:3. Within one embodiment, the antibody as described above or produced by a method described above, wherein the antibody further comprises a radionuclide, enzyme, substrate, cofactor, fluorescent marker, chemiluminescent marker, peptide tag, magnetic particle, drug, or toxin.

Within another aspect the present invention provides a method for inhibiting IL-TIF-induced proliferation or differentiation of hematopoietic cells and hematopoietic cell progenitors comprising culturing bone marrow or peripheral blood cells with a composition comprising an amount of an antibody as disclosed above or produced by a method disclosed above sufficient to reduce proliferation or differentiation of the hematopoietic cells in the bone marrow or peripheral blood cells as compared to bone marrow or peripheral blood cells cultured in the absence of soluble cytokine receptor. In one embodiment, the method for inhibiting IL-TIF-induced proliferation or differentiation of hematopoietic cells and hematopoietic cell progenitors is as disclosed above, wherein the hematopoietic cells and hematopoietic progenitor cells are lymphoid cells. In another embodiment, the method for inhibiting IL-TIF-induced proliferation or differentiation of hematopoietic cells and hematopoietic cell progenitors is as disclosed above, wherein the lymphoid cells are macrophages or T cells.

Within another aspect the present invention provides a method of reducing IL-TIF-induced or IL-9 induced inflammation comprising administering to a mammal with inflammation an amount of a composition of a an antibody as disclosed above or produced by a method disclosed above sufficient to reduce inflammation.

Within another aspect the present invention provides method of suppressing an inflammatory response in a mammal with inflammation comprising: (1) determining a level of serum amyloid A protein; (2) administering a composition comprising an antibody as described above or produced by a method described above an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Within another aspect the present invention provides method for detecting a cancer in a patient, comprising: obtaining a tissue or biological sample from a patient; incubating the tissue or biological sample with an antibody as described above or produced by a method described above under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase in the level of antibody bound to the patient tissue or biological sample relative to the normal control tissue or biological sample is indicative of a cancer in the patient.

Within another aspect the present invention provides a method of treating a mammal afflicted with an inflammatory disease in which IL-TIF or serum amyloid A plays a role, comprising: administering an antagonist of IL-TIF or serum amyloid A to the mammal such that the inflammation is reduced, wherein the antagonist is selected from the group consisting of an antibody or binding polypeptide that specifically binds a polypeptide or polypeptide fragment of IL-TIF (SEQ ID NO:3). Within another embodiment the method of treating a mammal afflicted with an inflammatory disease is as described above wherein the disease is a chronic inflammatory disease. Within another embodiment the method of treating a mammal afflicted with an inflammatory disease is as described above wherein the disease is a chronic inflammatory disease selected from the group consisting of: inflammatory bowel disease; ulcerative colitis; Crohn's disease; arthritis; and psoriasis. Within another embodiment the method of treating a mammal afflicted with an inflammatory disease is as described above wherein the disease is an acute inflammatory disease. Within another embodiment the method is as described above, wherein the disease is an acute inflammatory disease selected from the group consisting of: endotoxemia; septicemia; toxic shock syndrome; and infectious disease.

Within another embodiment the method of treating a mammal afflicted with an inflammatory disease is as described above, wherein the antibody further comprises a radionuclide, enzyme, substrate, cofactor, fluorescent marker, chemiluminescent marker, peptide tag, magnetic particle, drug, or toxin.

Within another aspect, the present invention provides an antibody comprising a monoclonal antibody that that binds to an epitope of human IL-TIF (SEQ ID NO:3) selected from the group consisting of: (a) an epitope consisting of the amino acid sequence of SEQ ID NO:3 from amino acid number 28 (Cys) to amino acid number 35 (Phe); (b) an epitope consisting of the amino acid sequence of SEQ ID NO:3 from amino acid number 52 (Ser) or 55 (Asp) to amino acid number 59 (Asp) or 62 (Leu); (c) an epitope consisting of the amino acid sequence of SEQ ID NO:3 from amino acid number 94 (Pro) or 95 (Gln) to amino acid number 100 (Gln) or 103 (Met); (d) an epitope consisting of the amino acid sequence of SEQ ID NO:3 from amino acid number 113 (Leu) to amino acid number 118 (Ser) or 119 (Thr); (e) an epitope consisting of the amino acid sequence of SEQ ID NO:3 from amino acid number 123 (Glu) to amino acid number 126 (Asp) or 128 (His); (f) an epitope consisting of the amino acid sequence of SEQ ID NO:3 from amino acid number 134 (Gln) or 144 (Gly) to amino acid number 147 (Gly); (g) an epitope consisting of the amino acid sequence of SEQ ID NO:3 from amino acid number 49 (Lys) to amino acid number 77 (Cys); (h) an epitope consisting of the amino acid sequence of SEQ ID NO:3 from amino acid number 89 (Glu) to amino acid number 101 (Pro), and further comprising a Cys at the N-terminus or C-terminus; and (i) an epitope consisting of the amino acid sequence of SEQ ID NO:3 from amino acid number 132 (Asn) to amino acid number 145 (Glu), and further comprising a Cys at the N-terminus or C-terminus; and wherein the antibody neutralizes the pro-inflammatory activity of the human IL-TIF polypeptide of SEQ ID NO:2 or SEQ ID NO:3. In one embodiment, the antibody is as disclosed above, wherein the antibody further comprises a radionuclide, enzyme, substrate, cofactor, fluorescent marker, chemiluminescent marker, peptide tag, magnetic particle, drug, or toxin. In another embodiment, the antibody is as disclosed above, wherein the antibody is selected from the group consisting of: (a) a murine monoclonal antibody, (b) a humanized antibody derived from (a), (c) an antibody fragment, and (d) a human monoclonal antibody.

Within another aspect, the present invention provides an antibody comprising a monoclonal antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1 (ATCC PTA-5037); (e) the hybridoma clone 266.12.6.1.3.2.1 (ATCC PTA-5034); and the hybridoma clone 266.19.1.10.5.2 (ATCC PTA-5036). In one embodiment, the antibody is as disclosed above, wherein the antibody further comprises a radionuclide, enzyme, substrate, cofactor, fluorescent marker, chemiluminescent marker, peptide tag, magnetic particle, drug, or toxin. In another embodiment, the antibody is as disclosed above, wherein the antibody is selected from the group consisting of: (a) a murine monoclonal antibody, (b) a humanized antibody derived from (a), and (c) an antibody fragment.

Within another aspect, the present invention provides a method of treating a pathological condition in a subject associated with IL-TIF activity comprising administering an effective amount of the antibody as disclosed above, thereby treating said pathological condition. In one embodiment, the method is as disclosed above, wherein said pathological condition is a chronic inflammatory condition. In another embodiment, the method is as disclosed above, wherein said chronic inflammatory condition is selected from the group consisting of: inflammatory bowel disease; ulcerative colitis; Crohn's disease; arthritis; and psoriasis. In another embodiment, the method is as disclosed above, wherein said pathological condition is an acute inflammatory condition. In another embodiment, the method is as disclosed above, wherein said acute inflammatory condition is selected from the group consisting of: endotoxemia; septicemia; toxic shock syndrome; and infectious disease.

Within another aspect, the present invention provides a method of treating a pathological condition in a subject associated with IL-TIF activity comprising administering an effective amount of the antibody as disclosed above, thereby treating said pathological condition. In one embodiment, the method is as disclosed above, wherein said pathological condition is a chronic inflammatory condition. In another embodiment, the method is as disclosed above, wherein said chronic inflammatory condition is selected from the group consisting of: inflammatory bowel disease; ulcerative colitis; Crohn's disease; arthritis; and psoriasis. In another embodiment, the method is as disclosed above, wherein said pathological condition is an acute inflammatory condition. In another embodiment, the method is as disclosed above, wherein said acute inflammatory condition is selected from the group consisting of: endotoxemia; septicemia; toxic shock syndrome; and infectious disease.

These and other aspects of the invention will become evident upon reference to the following detailed description of the invention. Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

An "anti-idiotype antibody" is an antibody that binds with the variable region domain of an immunoglobulin. In the present context, an anti-idiotype antibody binds with the variable region of an anti-Zcytor16 antibody, and thus, an anti-idiotype antibody mimics an epitope of Zcytor16.

An "antibody fragment" is a portion of an antibody such as $F(ab)_2$, $F(ab)_2$, Fab', Fab, and the like. Regardless of structure, an antibody fragment binds with the same antigen that is recognized by the intact antibody. For example, an anti-Zcytor16 monoclonal antibody fragment binds with an epitope of Zcytor16.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain Construction of humanized antibodies for therapeutic use in humans that are derived from murine antibodies, such as those that bind to or neutralize a human protein, is within the skill of one in the art.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of specification.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

IL-TIF polynucleotides are expressed in T-cells, activated T- and B-cells, and lymphoid tissue. The human IL-TIF nucleotide sequence is represented in SEQ ID NO:1. IL-TIF has also been designated "IL-22."

Analysis of SEQ ID NO:1 reveals that there are two possible initiation Methionine residues for a IL-TIF cytokine polypeptide translated therefrom. The two deduced IL-TIF polypeptide amino acid sequences are shown in SEQ ID NO:2 (a 179 amino acid polypeptide having the initiating Met at nucleotide 21 in SEQ ID NO:1) and SEQ ID NO:3 (a 167 amino acid polypeptide having the initiating Met at nucleotide 57 in SEQ ID NO:1). Although both of these sequences encode a IL-TIF polypeptide, based on similarity of the IL-TIF sequence to IL-10 and other cytokines, and the presence of a strong signal sequence, SEQ ID NO:3 encodes a fully functional secreted cytokine polypeptide.

Sequence analysis of the deduced amino acid sequence as represented in SEQ ID NO:3 indicates a 167 amino acid polypeptide containing a 22 amino acid residue secretory signal sequence (amino acid residues 1 (Met) to 21 (Ala) of SEQ ID NO:3), and a mature polypeptide of 146 amino acids (amino acid residues 22 (Ala) to 167 (Ile) of SEQ ID NO:3). N-terminal sequence shows that the mature start at residue 22 (Ala) of SEQ ID NO:3 or 34 (Ala) of SEQ ID NO:2.

In general, cytokines are predicted to have a four-alpha helix structure, with the 1$^{st}$ and 4$^{th}$ helices being most important in ligand-receptor interactions. The 1$^{st}$ and 4$^{th}$ helices are more highly conserved among members of the family. Referring to the human IL-TIF amino acid sequence shown in SEQ ID NO:3, alignment of human IL-TIF, human IL-10, human zcyto10 (WO US98/25228) (a.k.a. IL-20), and human MDA7 (Genbank Accession No. Q13007) amino acid sequences suggests that IL-TIF helix A is defined by amino acid residues 41 (Thr) to 53 (leu) of SEQ ID NO:3; helix B by amino acid residues 80 (Met) to 91 (Val) of SEQ ID NO:3; helix C by amino acid residues 103 (Met) to 116 (Arg) of SEQ ID NO:3; and helix D by amino acid residues 149 (Ile) to 162 Leu) of SEQ ID NO:3. Structural analysis suggests that the A/B loop is long, the B/C loop is short and the C/D loop is long. This loop structure results in an up-up-down-down helical organization. Four cysteine residues are conserved between IL-10 and IL-TIF corresponding to amino acid residues 8, 28, 77 and 120 of SEQ ID NO:3. Consistent cysteine placement is further confirmation of the four-helical-bundle structure.

The corresponding polynucleotides encoding the IL-TIF polypeptide regions, domains, motifs, residues and sequences described herein are as shown in SEQ ID NO:1. Moreover, the corresponding IL-TIF polypeptide regions, domains, motifs, residues and sequences described herein are also as shown in SEQ ID NO:2 and SEQ ID NO:3.

Four-helical bundle cytokines are also grouped by the length of their component helices. "Long-helix" form cytokines generally consist of between 24-30 residue helices and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. IL-TIF is believed to be a new member of the short-helix form cytokine group. Studies using CNTF and IL-6 demonstrated that a CNTF helix can be exchanged for the equivalent helix in IL-6, conferring CTNF-binding properties to the chimera. Thus, it appears that functional domains of four-helical cytokines determined on the basis of structural homology, irrespective of sequence identity, and can maintain functional integrity in a chimera (Kallen et al., *J. Biol. Chem.* 274: 11859-11867, 1999). Using similar methods, putative regions conferring receptor binding specificity in IL-TIF comprise the regions of amino acid residues of SEQ ID NO:3 that include: residues 53-60, residues 85-91, and residues 121-140. These regions will be useful for preparing chimeric molecules, particularly with other short-helix form cytokines to determine and modulate receptor binding specificity. Moreover knowledge of the structure of IL-TIF is useful for one of skill in the art to identify epitopes and functional domain polypeptide fragments of IL-TIF for use in preparing antibodies of the present invention.

Receptors for IL-TIF have been identified, comprising zcytor16 (SEQ ID NO:32, and SEQ ID NO:33) ((commonly owned WIPO Publication No. WO 01/40467)), zcytor11 (SEQ ID NO:18, and SEQ ID NO:19) (Commonly owned U.S. Pat. No. 5,965,704), and CRF2-4 (Genbank Accession No. Z17227). Moreover several IL-TIF responsive cell lines have been identified (Dumontier et al., *J. Immunol.* 164:1814-1819, 2000; Dumontier, L. et al., *Proc. Nat'l. Acad. Sci.* 97:10144-10149, 2000; Xie M H et al., *J. Biol. Chem.* 275: 31335-31339, 2000; Kotenko S V et al., *J. Biol. Chem.* 276: 2725-2732, 2001), as well as those that express the IL-TIF receptor subunit zcytor11. Moreover, commonly owned zcytor16 receptor was shown to bind IL-TIF and antagonize its activity (SEQ ID NO:3) (commonly owned WIPO Publication No. WO. 01/40467); the mouse IL-TIF (IL-TIF) sequence is shown in Dumontier et al., *J. Immunol.* 164:1814-1819, 2000), and was independently cloned, designated, mouse IL-TIF herein, and is shown in SEQ ID NO:37 and corresponding polypeptide sequence shown in SEQ ID NO:38. Moreover, commonly owned zcytor11 (U.S. Pat. No. 5,965,704) and CRF2-4 receptor also bind IL-TIF (See, WIPO publication WO 00/24758; Dumontier et al., *J. Immunol.* 164:1814-1819, 2000; Spencer, S D et al., *J. Exp. Med.* 187:571-578, 1998; Gibbs, V C and Pennica Gene 186:97-101, 1997 (CRF2-4 cDNA); Xie, M H et al., *J. Biol. Chem.* 275: 31335-31339, 2000; and Kotenko, S V et al., *J. Biol. Chem.* 276:2725-2732, 2001). Moreover, IL-10β receptor may be involved as a receptor for IL-TIF, and it is believed to be synonymous with CRF2-4 (Dumoutier, L. et al., *Proc. Nat'l. Acad. Sci.* 97:10144-10149, 2000; Liu Y et al, *J. Immunol.* 152; 1821-1829, 1994 (IL-10R cDNA). These receptors are discussed herein in relation to the uses of IL-TIF, and as antagonists thereto.

The present invention utilizes polynucleotide molecules, including DNA and RNA molecules, that encode the IL-TIF polypeptides disclosed herein. Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the IL-TIF polypeptide of SEQ ID NO:3. Those skilled in the art will recognize that the degenerate sequence of SEQ ID NO:4 also provides all RNA sequences encoding SEQ ID NO:3 by substituting U for T. Thus, IL-TIF polypeptide-encoding polynucleotides comprising nucleotide 1 or 66 to nucleotide 501 of SEQ ID NO:4 and their RNA equivalents are contemplated by the present invention. Table 1 sets forth the one-letter codes used within SEQ ID NO:4 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |

TABLE 2-continued

| Amino Acid | One Letter Code | Codons | Degenerate Codon |
|---|---|---|---|
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:3. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into polynucleotides by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferential codons can be tested and optimized for expression in various species, and tested for functionality as disclosed herein.

Methods for preparing DNA and RNA are well known in the art. In general, RNA is isolated from a tissue or cell that produces large amounts of IL-TIF RNA. Such tissues and cells are identified by Northern blotting (Thomas, *Proc. Natl.*

Acad. Sci. USA 77:5201, 1980), reverse transcriptase PCR (RT-PCR) or by screening conditioned medium from various cell types for activity on target cells or tissue. Once the activity or RNA producing cell or tissue is identified, total RNA can be prepared using guanidinium isothiocyanate extraction followed by isolation by centrifugation in a CsCl gradient (Chirgwin et al., *Biochemistry* 18:52-94, 1979). Poly (A)⁺ RNA is prepared from total RNA using the method of Aviv and Leder (*Proc. Natl. Acad. Sci. USA* 69:1408-12, 1972). Complementary DNA (cDNA) is prepared from poly(A)⁺ RNA using known methods. In the alternative, genomic DNA can be isolated. Polynucleotides encoding IL-TIF polypeptides are then identified and isolated by, for example, hybridization or PCR.

A full-length clone encoding IL-TIF can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to IL-TIF fragments, or other specific binding partners.

IL-TIF polynucleotide sequences disclosed herein can also be used as probes or primers to clone 5' non-coding regions of a IL-TIF gene. In view of the tissue-specific expression observed for IL-TIF by Northern blotting and RT PCR (See, Examples 2 and 3), this gene region is expected to provide for hematopoietic- and lymphoid-specific expression. Promoter elements from a IL-TIF gene could thus be used to direct the tissue-specific expression of heterologous genes in, for example, transgenic animals or patients treated with gene therapy. Cloning of 5' flanking sequences also facilitates production of IL-TIF proteins by "gene activation" as disclosed in U.S. Pat. No. 5,641,670. Briefly, expression of an endogenous IL-TIF gene in a cell is altered by introducing into the IL-TIF locus a DNA construct comprising at least a targeting sequence, a regulatory sequence, an exon, and an unpaired splice donor site. The targeting sequence is a IL-TIF 5' non-coding sequence that permits homologous recombination of the construct with the endogenous IL-TIF locus, whereby the sequences within the construct become operably linked with the endogenous IL-TIF coding sequence. In this way, an endogenous IL-TIF promoter can be replaced or supplemented with other regulatory sequences to provide enhanced, tissue-specific, or otherwise regulated expression.

Counterpart IL-TIF polypeptides and polynucleotides from other species (orthologs) can be isolated. Of particular interest are IL-TIF polypeptides from other mammalian species, including murine, porcine, ovine, bovine, canine, feline, equine, and other primate polypeptides. Orthologs of human IL-TIF can be cloned using information and compositions provided by the present invention in combination with conventional cloning techniques well known in the art, e.g., by using degenerate probes based on the disclosed sequences, or PCR (Mullis, U.S. Pat. No. 4,683,202) using primers designed from the representative human IL-TIF sequence disclosed herein. Within an additional method, the cDNA library can be used to transform or transfect host cells, and expression of the cDNA of interest can be detected with an antibody to IL-TIF polypeptide, binding studies or activity assays. Similar techniques can also be applied to the isolation of genomic clones. Example 5 shows that a IL-TIF ortholog is present in mouse genomic DNA.

A polynucleotide sequence for the mouse ortholog of human IL-TIF has been identified and is shown in SEQ ID NO:37 and the corresponding amino acid sequence shown in SEQ ID NO:38. Analysis of the mouse IL-TIF polypeptide encoded by the DNA sequence of SEQ ID NO:37 revealed an open reading frame encoding 179 amino acids (SEQ ID NO:38) comprising a predicted secretory signal peptide of 33 amino acid residues (residue 1 (Met) to residue 33 (Ala) of SEQ ID NO:38), and a mature polypeptide of 146 amino acids (residue 34 (Leu) to residue 179 (Val) of SEQ ID NO:38). IL-TIF helix A is defined by amino acid residues 53 to 65 of SEQ ID NO:38; helix B by amino acid residues 92 to 103 of SEQ ID NO:38; helix C by amino acid residues 115 to 124 of SEQ ID NO:38; and helix D by amino acid residues 161 to 174 of SEQ ID NO:38. Four conserved cysteine residues in mouse IL-TIF are conserved with the human sequence corresponding to amino acid residues 20, 40, 89; and 132 of SEQ ID NO:38. Moreover, in the mouse sequence alternative starting Methionine residues exist at positions 8 and 13 as shown in SEQ ID NO:38, but the signal peptide cleavage after residue 33 (Ala) would still result in the 146 amino acid mature sequence as described above. The mature sequence for the mouse IL-TIF begins at Leu$_{34}$ (as shown in SEQ ID NO:38), which corresponds to Ala$_{22}$ (as shown in SEQ ID NO:3) in the human sequence. There is about 78% identity between the mouse and human sequences over the entire amino acid sequence corresponding to SEQ ID NO:3 and SEQ ID NO:38. The above percent identities were determined using a FASTA program with ktup=1, gap opening penalty=12, gap extension penalty=2, and substitution matrix=BLOSUM62, with other FASTA parameters set as default. The corresponding polynucleotides encoding the mouse IL-TIF polypeptide regions, domains, motifs, residues and sequences described above are as shown in SEQ ID NO:37.

Those skilled in the art will recognize that the sequence disclosed in SEQ ID NO:1 represents a single allele of human IL-TIF and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:3. cDNAs generated from alternatively spliced mRNAs, which retain the properties of the IL-TIF polypeptide, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Moreover, isolation of IL-TIF-encoding nucleic acid molecules that can hybridize under stringent conditions to nucleic acid molecules having the nucleotide sequence of SEQ ID NO:1, to nucleic acid molecules having the nucleotide sequence of nucleotides 87 to 587 of SEQ ID NO:1, or to nucleic acid molecules having a nucleotide sequence complementary to SEQ ID NO:1, is well within the skill of one in the art. See, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)).

To prepare the antibodies or binding polypeptides of the present invention, IL-TIF polypeptides may be used that have a substantially similar sequence identity to the polypeptides of SEQ ID NO:3, or their orthologs. The term "substantially similar sequence identity" is used herein to denote polypeptides comprising at least 70%, at least 80%, at least 90%, at least 95%, or greater than 95% sequence identity to the sequences shown in SEQ ID NO:3, or their orthologs. The present invention also includes polypeptides that comprise an amino acid sequence having at least 70%, at least 80%, at least 90%, at least 95% or greater than 95% sequence identity to the sequence of amino acid residues 1 to 167, or 23 to 167 of SEQ ID NO:3; or amino acid residues 1 to 179, or 35 to 179 of SEQ ID NO:2. The present invention further includes nucleic acid molecules that encode such polypeptides. Methods for determining percent identity are described below.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes).

$$\frac{\text{Total number of identical matches}}{\left[\begin{array}{c}\text{length of the longer sequence plus the}\\ \text{number of gaps introduced into the longer}\\ \text{sequence in order to align the two sequences}\end{array}\right]} \times 100$$

density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

Variant IL-TIF polypeptides or polypeptides with substantially similar sequence identity are characterized as having one or more amino acid substitutions, deletions or additions.

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant IL-TIF. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:3) and a test sequence that have either the highest These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 110 to 180 amino acid residues that comprise a sequence that is at least 70%, preferably at least 90%, and more preferably 95% or more identical to the corresponding region of SEQ ID NO:3. Polypeptides comprising affinity tags can further comprise a proteolytic cleavage site between the IL-TIF polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in IL-TIF polypeptides so as to minimize disruption of higher order structure essential to biological activity. For example, when the IL-TIF polypeptide comprises one or more helices, changes in amino acid residues will be made so as not to disrupt the helix geometry and other components of the molecule where changes in conformation abate some critical function, for example, an active site, or binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the IL-TIF protein sequence as shown in SEQ ID NO:3 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in IL-TIF, hydrophilic regions include: (1) amino acid number 29 (Arg) to amino acid number 34 (Asn) of SEQ ID NO:3; (2) amino acid number 121 (His) to amino acid number 126 (Asp) of SEQ ID NO:3; (3) amino acid number 134 (Gln) to amino acid number 139 (Thr) of SEQ ID NO:3; (4) amino acid number 137 (Lys) to amino acid number 142 (Lys) of SEQ ID NO:3; and (5) amino acid number 145 (Glu) to amino acid number 150 (Lys) of SEQ ID NO:2.

Those skilled in the art will recognize that hydrophilicity or hydrophobicity will be taken into account when designing modifications in the amino acid sequence of a IL-TIF polypeptide, or in choosing epitopes for generation of antibodies to IL-TIF, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO:3. Cysteine residues at positions 8, 27, 77 and 120 of SEQ ID NO:3, will be relatively intolerant of substitution.

The identities of essential amino acids can also be inferred from analysis of sequence similarity between IL-10, zcyto10, and MDA7 with IL-TIF. Using methods such as "FASTA" analysis described previously, regions of high similarity are identified within a family of proteins and used to analyze amino acid sequence for conserved regions. An alternative approach to identifying a variant IL-TIF polynucleotide on the basis of structure is to determine whether a nucleic acid molecule encoding a potential variant IL-TIF gene can hybridize to a nucleic acid molecule having the nucleotide sequence of SEQ ID NO:1, as discussed above.

Other methods of identifying essential amino acids in IL-TIF polypeptides are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996).

The present invention also includes using functional fragments of IL-TIF polypeptides, antigenic epitopes, epitope-bearing portions of IL-TIF polypeptides, and nucleic acid molecules encoding such functional fragments, antigenic epitopes, epitope-bearing portions of IL-TIF polypeptides, to generate polypeptides for use in generating activity blocking or antagonizing antibodies and binding polypeptides to IL-TIF. A "functional" IL-TIF or fragment thereof as defined herein is characterized by its proliferative or differentiating activity, by its ability to induce or inhibit specialized cell functions, or by its ability to bind specifically to an anti-IL-TIF antibody, cell, or IL-TIF receptor (either soluble or immobilized). As previously described herein, IL-TIF is characterized by a four-helical-bundle structure comprising helix A (amino acid residues 41-53), helix B (amino acid residues 80-91), helix C (amino acid residues 103-116) and helix D (amino acid residues 149-162), as shown in SEQ ID NO:3. Thus, the present invention further contemplates using fusion proteins encompassing: (a) polypeptide molecules comprising one or more of the helices described above; and (b) functional fragments comprising one or more of these helices. The other polypeptide portion of the fusion protein may be contributed by another four-helical-bundle cytokine, such as IL-10, zcyto10, MDA7, IL-15, IL-2, IL-4 and GM-CSF, or by a non-native and/or an unrelated secretory signal peptide that facilitates secretion of the fusion protein.

Routine deletion analyses of nucleic acid molecules can be performed to obtain functional fragments of a nucleic acid molecule that encodes a IL-TIF polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for IL-TIF activity, or for the ability to bind anti-IL-TIF antibodies or IL-TIF receptor. One alternative to exonuclease digestion is to use oligonucleotide-directed mutagenesis to introduce deletions or stop codons to specify production of a desired IL-TIF fragment. Alternatively, particular fragments of a IL-TIF gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5 A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1 Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204), and region-directed mutagenesis (Derbyshire et al., *Gene* 46:145 (1986), and Ner et al., *DNA* 7:127, (1988)).

Variants of the disclosed IL-TIF nucleotide and polypeptide sequences can also be generated through DNA shuffling as disclosed by Stemmer, *Nature* 370:389 (1994), Stemmer, *Proc. Natl. Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-IL-TIF antibodies or soluble IL-TIF receptor, can be recovered from the host cells and rapidly sequenced using modern equipment. These methods allow the rapid determination of the importance of individual amino acid residues in a polypeptide of interest, and can be applied to polypeptides of unknown structure.

In addition, useful antibodies and binding polypeptides of the present invention, IL-TIF proteins (or polypeptide fragments thereof) can be joined to other bioactive molecules, particularly other cytokines, to provide multi-functional molecules. For example, anti-IL-TIF antibodies and binding partners can be joined to other cytokines to enhance or prolong their biological properties.

The present invention thus contemplates using a series of hybrid molecules in which a segment comprising one or more of the helices of IL-TIF is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tent-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202: 301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for IL-TIF amino acid residues.

The present invention also provides polypeptide fragments or peptides comprising an epitope-bearing portion of a IL-TIF polypeptide described herein. Such fragments or peptides may comprise an "immunogenic epitope," which is a part of a protein that elicits an antibody response when the entire protein is used as an immunogen Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein. Hopp/Woods hydrophilicity profiles can be used to determine regions that have the most antigenic potential (Hopp et al., 1981, ibid. and Hopp, 1986, ibid.). In IL-TIF these regions include: (1) amino acid number 29 (Arg) to amino acid number 34 (Asn) of SEQ ID NO:3; (2) amino acid number 121 (His) to amino acid number 126 (Asp) of SEQ ID NO:3; (3) amino acid number 134 (Gln) to amino acid number 139 (Thr) of SEQ ID NO:3; (4) amino acid number 137 (Lys) to amino acid number 142 (Lys) of SEQ ID NO:3; and (5) amino acid number 145 (Glu) to amino acid number 150 (Lys) of SEQ ID NO:2. Moreover, IL-TIF antigenic epitopes as predicted by a Jameson-Wolf plot, e.g., using DNASTAR Protean program (DNASTAR, Inc., Madison, Wis.) serve as preferred antigens, and can be determined by one of skill in the art. Such antigens include (1) amino acid number 28 (Cys) to amino acid number 35 (Phe) of SEQ ID NO:3; (2) amino acid number 52 (Ser) or 55 (Asp) to amino acid number 59 (Asp) or 62 (Leu) of SEQ ID NO:3; (3) amino acid number 94 (Pro) or 95 (Gln) to amino acid number 100 (Gln) or 103 (Met) of SEQ ID NO:3; (4) amino acid number 113 (Leu) to amino acid number 118 (Ser) or 119 (Thr) of SEQ ID NO:3; (5) amino acid number 123 (Glu) to amino acid number 126 (Asp) or 128 (His) of SEQ ID NO:3; and (6) amino acid number 134 (Gln) or 144 (Gly) to amino acid number 147 (Gly) of SEQ ID NO:3. Other antigens include huIL-TIF-1 (SEQ ID NO:34; comprising amino acid number 49 (Lys) to amino acid number 77 (Cys) of SEQ ID NO:3) or huIL-TIF-2 (SEQ ID NO:35; comprising amino acid number 89 (Glu) to amino acid number 101 (Pro) of SEQ ID NO:3) or huIL-TIF-3 (SEQ ID NO:36; comprising amino acid number 132 (Asn) to amino acid number 145 (Glu) of SEQ ID NO:3).

Antigenic epitope-bearing peptides and polypeptides preferably contain at least four to ten amino acids, at least ten to fifteen amino acids, or about 15 to about 30 amino acids of SEQ ID NO:3. Such epitope-bearing peptides and polypeptides can be produced by fragmenting a IL-TIF polypeptide, or by chemical peptide synthesis, as described herein. Moreover, epitopes can be selected by phage display of random peptide libraries (see, for example, Lane and Stephen, *Curr. Opin. Immunol* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology, pages* 9.3.1-9.3.5 and pages 9.4.1-9.4.11 (John Wiley & Sons 1997).

Regardless of the particular nucleotide sequence of a variant IL-TIF polynucleotide, the polynucleotide encodes a polypeptide that is characterized by its pro-inflammatory activity, proliferative or differentiating activity, its ability to induce or inhibit specialized cell functions, or by the ability to bind specifically to an anti-IL-TIF antibody or IL-TIF receptor. More specifically, variant IL-TIF polynucleotides will encode polypeptides which exhibit at least 50% and preferably, greater than 70%, 80% or 90%, of the activity of the polypeptide as shown in SEQ ID NO:3.

For any IL-TIF polypeptide, including variants and fusion proteins, one of ordinary skill in the art can readily generate a fully degenerate polynucleotide sequence encoding that variant using the information set forth in Tables 1 and 2 above.

The present invention further provides a variety of other polypeptide fusions (and related multimeric proteins comprising one or more polypeptide fusions). For example, a IL-TIF polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-IL-TIF polypeptide fusions can be expressed in genetically engineered cells (to produce a variety of multimeric IL-TIF analogs). Auxiliary domains can be fused to IL-TIF polypeptides to target them to specific cells, tissues, or macromolecules. For example, a IL-TIF polypeptide or protein could be targeted to a predetermined cell type by fusing a IL-TIF polypeptide to a ligand that specifically binds to a receptor on the surface of that target cell. In this way, polypeptides and proteins can be targeted for therapeutic or diagnostic purposes. A IL-TIF polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

Using the methods discussed herein, one of ordinary skill in the art can identify and/or prepare a variety of polypeptides that have substantially similar sequence identity to amino acid residues 1-167 or 23-167 of SEQ ID NO:3, or functional fragments and fusions thereof, wherein such polypeptides or fragments or fusions retain the properties of the wild-type protein such as the ability to stimulate, enhance or promote inflammation, proliferation, differentiation, induce specialized cell function or bind the IL-TIF receptor or IL-TIF antibodies.

For use in generating antibodies or binding polypeptides of the present invention, IL-TIF polypeptides, including full-length polypeptides, functional fragments, antigenic epitopes, epitope-bearing portions of IL-TIF polypeptides, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a IL-TIF polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a IL-TIF polypeptide into the secretory pathway of a host cell, a secretory signal sequence (also known as a leader sequence, prepro sequence or pre sequence) is provided in the expression vector. The secretory signal sequence may be that of IL-TIF (e.g., amino acid 1 (Met) to 21 (Ala) of SEQ ID NO:3), or may be derived from another secreted protein (e.g., t-PA) or synthesized de novo. The secretory signal sequence is operably linked to the IL-TIF DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells are well known in the art. See, e.g., Wigler et al., *Cell* 14:725, 1978; Corsaro and Pearson, *Somatic Cell Genetics* 7:603, 1981: Graham and Van der Eb, *Virology* 52:456, 1973; Neumann et al., *EMBO J.* 1:841-5, 1982; Hawley-Nelson et al., Focus 15:73, 1993; Ciccarone et al., *Focus* 15:80, 1993; and Miller and Rosman, *BioTechniques* 7:980-90, 1989; Wang and Finer, *Nature Med.* 2:714-6, 1996. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells known in the art. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. The second method of making recombinant baculovirus utilizes a transposon-based system described by Luckow (Luckow, V. A, et al., *J Virol* 67:4566-79, 1993). See, Hill-Perkins, M. S, and Possee, R. D., *J. Gen. Virol.* 71:971-6, 1990; Bonning, B. C. et al., *J. Gen. Virol.* 75:1551-6, 1994; and, Chazenbalk, G. D., and Rapoport, B., *J. Biol. Chem.* 270:1543-9, 1995. Moreover, vectors can include an in-frame fusion with DNA encoding an epitope tag at the C- or N-terminus of the expressed IL-TIF polypeptide, or polypeptide fragment, for example, a Glu-Glu epitope tag (Grussenmeyer, T. et al., *Proc. Natl. Acad. Sci.* 82:7952-4, 1985). Also, See, in general, Glick and Pasternak, *Molecular Biotechnology: Principles and Applications of Recombinant DNA*, ASM Press, Washington, D.C., 199; and King, L. A. and Possee, R. D., ibid.; O'Reilly, D. R. et al., ibid.; Richardson, C. D., ibid.).

Fungal cells, including yeast cells, can also be used within the present invention to generate IL-TIF polypeptides and polypeptide fragments used to generate antibodies of the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075; Kingsman et al., U.S. Pat. No. 4,615,974; and Bitter, U.S. Pat. No. 4,977,092). See also U.S. Pat. Nos. 4,990,446; 5,063,154; 5,139,936 and 4,661,454. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.).

For use in the present invention, it is preferred to purify IL-TIF polypeptides and polypeptide fragments to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant IL-TIF polypeptides (or chimeric IL-TIF polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography Principles & Methods*, Pharmacia LKB Biotechnology, Uppsala, Sweden, 1988.

IL-TIF polypeptides and polypeptide fragments can be isolated by exploitation of their physical properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol., Vol.* 182, "Guide to Protein Purification", M. Deutscher, (ed.), Acad. Press, San Diego, 1990, pp. 529-39) and use of the soluble IL-TIF receptor. Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid IL-TIF proteins, are constructed using regions or domains of IL-TIF in combination with those of other human cytokine family proteins (e.g. interleukins or GM-CSF), or heterologous proteins (Sambrook et al., ibid., Altschul et al., ibid., Picard, *Cur. Opin. Biology,* 5:511-5, 1994, and references therein). These methods allow the determination of the biological importance of larger domains or regions in a polypeptide of interest. Such hybrids may alter reaction kinetics, binding, alter cell proliferative activity, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a helix conferring a biological function may be swapped between IL-TIF with the functionally equivalent helices from another family member, such as IL-10, zcyto10, MDA7, IL-15, IL-2, IL-4 and GM-CSF. Such components include, but are not limited to, the secretory signal sequence, helices A, B, C, D and four-helical-bundle cytokines. Such fusion proteins would be expected to have a biological functional profile that is the same or similar to IL-TIF polypeptides or other known four-helical-bundle cytokine family proteins, depending on the fusion constructed. Moreover, such fusion proteins may exhibit other properties as disclosed herein.

Standard molecular biological and cloning techniques can be used to swap the equivalent domains between the IL-TIF polypeptide and those polypeptides to which they are fused. Generally, a DNA segment that encodes a domain of interest, e.g., IL-TIF helices A through D, or other domain described herein, is operably linked in frame to at least one other DNA segment encoding an additional polypeptide (for instance a domain or region from another cytokine, such as IL-10, or zcyto10, MDA7 or the like), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a mature four helical bundle cytokine fusion protein containing helix A, followed by helix B, followed by helix C, followed by helix D. or for example, any of the above as interchanged with equivalent regions from another four helical bundle cytokine family protein. Such fusion proteins can be expressed, isolated, and assayed for activity as described herein. Moreover, such fusion proteins can be used to express and secrete fragments of the IL-TIF polypeptide, to be used, for example to inoculate an animal to generate anti-IL-TIF antibodies as described herein. For example a secretory signal sequence can be operably linked to helix A, B, C or D, or a combination thereof (e.g., operably linked polypeptides comprising helices A-B, B-C, C-D, A-C, A-D, B-D, or IL-TIF polypeptide fragments described herein), to secrete a fragment of IL-TIF polypeptide that can be purified as described herein and serve as an antigen to be inoculated into an animal to produce anti-IL-TIF antibodies, as described herein.

IL-TIF polypeptides or fragments thereof may also be prepared through chemical synthesis. IL-TIF polypeptides may be monomers or multimers; glycosylated or non-glycosylated; pegylated or non-pegylated; and may or may not include an initial methionine amino acid residue. For example, the polypeptides can be prepared by solid phase peptide synthesis, for example as described by Merrifield, *J. Am. Chem. Soc.* 85:2149, 1963.

The activity of IL-TIF molecules can be measured using a variety of assays that measure proliferation of and/or binding to cells expressing the IL-TIF receptor. Of particular interest are changes in IL-TIF-dependent cells. Suitable cell lines to be engineered to be IL-TIF-dependent include the IL-3-dependent BaF3 cell line (Palacios and Steinmetz, *Cell* 41: 727-734, 1985; Mathey-Prevot et al., *Mol. Cell. Biol.* 6: 4133-4135, 1986), FDC-P1 (Hapel et al., *Blood* 64: 786-790, 1984), and MO7e (Kiss et al., *Leukemia* 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today*, 8th Ann. Mtg. Int. Soc. Exp. Hematol. 1979, 145-156, 1980). For example, Baf3 cells expressing the IL-TIF heterodimeric receptor zcytor11/CRF2-4, as described herein, can be used to assay the activity of IL-TIF, IL-TIF receptor-binding fragments, and IL-TIF variants. The BaF3 stable cell line that co-expressing zcytor11 and CRF2-4 (IL-TIF receptor) exhibits dose-dependent proliferative response to IL-TIF protein in the media without IL-3.

IL-TIF is useful for stimulating proliferation, activation, differentiation and/or induction or inhibition of specialized cell function of cells involved in homeostasis of hematopoiesis and immune function. In particular, IL-TIF polypeptides are useful for stimulating proliferation, activation, differentiation, induction or inhibition of specialized cell functions of cells of the hematopoetic lineages, including, but not limited to, T cells, B cells, NK cells, dendritic cells, monocytes, and macrophages. Proliferation and/or differentiation of hematopoietic cells can be measured in vitro using cultured cells or in vivo by administering IL-TIF molecules to the appropriate animal model. Antibodies or binding polypeptides of the present invention can be assessed by showing antagonism or inhibition of such activities. Assays measuring cell proliferation or differentiation are well known in the art. For example, assays measuring proliferation include such assays as chemosensitivity to neutral red dye (Cavanaugh et al., *Investigational New Drugs* 8:347-354, 1990, incorporated herein by reference), incorporation of radiolabelled nucleotides (Cook et al., *Analytical Biochem.* 179:1-7, 1989, incorporated herein by reference), incorporation of 5-bromo-2'-deoxyuridine (BrdU) in the DNA of proliferating cells (Porstmann et al., *J. Immunol. Methods* 82:169-179, 1985, incorporated herein by reference), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989; all incorporated herein by reference).

IL-10 is a cytokine that inhibits production of other cytokines, induces proliferation and differentiation of activated B lymphocytes, inhibits HIV-1 replication and exhibits antagonistic effects on gamma interferon. IL-10 appears to exist as a dimer formed from two alpha-helical polypeptide regions related by a 180° rotation. See, for example, Zdanov et al., *Structure:* 3(6): 591-601 (1996). IL-10 has been reported to be a product of activated Th2 T-cells, B-cells, keratinocytes and monocytes/macrophages that is capable of modulating a Th1 T-cell response. Such modulation may be accomplished by inhibiting cytokine synthesis by Th1 T-cells. See, for example, Hus et al., *Int. Immunol.* 4: 563 (1992) and D'Andrea et al., *J. Exp. Med.* 178: 1042 (1992). IL-10 has also been reported to inhibit cytokine synthesis by natural killer cells and monocytes/macrophages. See, for example, Hus et al. cited above and Fiorentino et al., *J. Immunol.* 146: 3444 (1991). In addition, IL-10 has been found to have a protective effect with respect to insulin dependent diabetes mellitus. Similarly, as a cytokine sharing polypeptide structure and some sequence similarity to IL-10, IL-TIF can have these above disclosed activities, and the assays used to assess IL-10 activity can be applied to assay IL-TIF activity.

IL-TIF can be assayed in vivo using viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161-89, 1994; and J. T. Douglas and D. T. Curiel, *Science & Medicine* 4:44-53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022-2032, 1998; Raper, S. E. et al., *Human Gene Therapy* 9:671-679, 1998). In addition, deletion of E2b is reported to reduce immune responses (Amalfitano, A. et al., *J. Virol.* 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can also be used for protein production in vitro. By culturing adenovirus-infected cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

In view of the tissue distribution observed for IL-TIF receptor agonists (including the natural ligand/substrate/cofactor/etc.) and/or antagonists have enormous potential in both in vitro and in vivo applications. Compounds identified as IL-TIF agonists are useful for expansion, proliferation, activation, differentiation, and/or induction or inhibition of specialized cell functions of cells involved in homeostasis of hematopoiesis and immune function. Agonists are thus useful in specifically promoting the growth and/or development of T-cells, B-cells, platelets and other cells of the lymphoid and myeloid lineages ex vivo or in culture.

Antagonists, such as antibodies and binding partners of the present invention are useful to diagnose and treat diseases that manifest acurte and chronic inflammation, as they can decrease inflammation induced by IL-TIF. Antagonists are also useful as research reagents for characterizing sites of ligand-receptor interaction. Antagonists are useful to reduce or ablate inflammation and may be involved in inhibiting expansion, proliferation, activation, and/or differentiation of cells involved in regulating hematopoiesis. Inhibitors of IL-TIF activity (IL-TIF antagonists) include anti-IL-TIF antibodies, binding polypeptides and soluble IL-TIF receptors, as well as other peptidic and non-peptidic agents (including ribozymes).

IL-TIF can also be used to identify inhibitors (antagonists) of its activity. Test compounds are added to the assays disclosed herein to identify compounds that inhibit the activity of IL-TIF. In addition to those assays disclosed herein, samples can be tested for inhibition of IL-TIF activity within a variety of assays designed to measure receptor binding, the stimulation/inhibition of IL-TIF-dependent cellular responses or proliferation of IL-TIF receptor-expressing cells.

A IL-TIF polypeptide can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the $F_c$ portions are disulfide bonded to each other and two non-Ig polypeptides are arrayed in closed proximity to each other. Fusions of this type can be used to (e.g., for dimerization, increasing stability and in vivo half-life, affinity purify ligand, in vitro assay tool, antagonist). For use in assays, the chimeras are bound to a support via the $F_c$ region and used in an ELISA format. $F_c$ fusions may represent preferred therapeutic proteins with different pharmacokinetics and altered action.

To assist in isolating anti-IL-TIF and binding partners of the present invention, an assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding Alternatively, ligand/receptor binding can be analyzed using SELDI™ technology (Ciphergen, Inc., Palo Alto, Calif.). Moreover, BIACORE technology, described above, can be used in competition experiments to determine if different monoclonal antibodies bind the same or different epitopes on the IL-TIF polypeptide, and as such, be used to aid in epitope mapping of neutralizing anti-IL-TIF antibodies of the present invention.

Ligand-binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

IL-TIF polypeptides can also be used to prepare antibodies of the present invention that bind to IL-TIF epitopes, peptides or polypeptides. The IL-TIF polypeptide or a fragment thereof serves as an antigen (immunogen) to inoculate an animal and elicit an immune response. Such antibodies can be used to block the biological action of pro-inflammatory IL-TIF and are useful as anti-inflammatory therapeutics in a variety of diseases as described herein. One of skill in the art would recognize that antigenic, epitope-bearing polypeptides contain a sequence of at least 6, preferably at least 9, and more preferably at least 15 to about 30 contiguous amino acid residues of a IL-TIF polypeptide (e.g., SEQ ID NO:3). Polypeptides comprising a larger portion of a IL-TIF polypeptide, i.e., from 30 to 100 residues up to the entire length of the amino acid sequence are included. Antigens or immunogenic epitopes can also include attached tags, adjuvants and carriers, as described herein. Suitable antigens include the IL-TIF polypeptide encoded by SEQ ID NO:3 from amino acid number 23 to amino acid number 167, or a contiguous 9 to 144, or 30 to 144 amino acid fragment thereof. Other suitable antigens include helices of the four-helical-bundle structure, as described herein. Preferred peptides to use as antigens are hydrophilic peptides such as those predicted by one of skill in the art from a hydrophobicity plot, as described herein. For example suitable hydrophilic peptides include: (1) amino acid number 29 (Arg) to amino acid number 34 (Asn) of SEQ ID NO:3; (2) amino acid number 121 (His) to amino acid number 126 (Asp) of SEQ ID NO:3; (3) amino acid number 134 (Gln) to amino acid number 139 (Thr) of SEQ ID NO:3; (4) amino acid number 137 (Lys) to amino acid number 142 (Lys) of SEQ ID NO:3; and (5) amino acid number 145 (Glu) to amino acid number 150 (Lys) of SEQ ID NO:2. Moreover, IL-TIF antigenic epitopes as predicted by a Jameson-Wolf plot, e.g., using DNASTAR Protean program (DNASTAR, Inc., Madison, Wis.) serve as preferred antigens, and are determined by one of skill in the art, and described herein. Such antigens include (1) amino acid number 28 (Cys) to amino acid number 35 (Phe) of SEQ ID NO:3; (2) amino acid number 52 (Ser) or 55 (Asp) to amino acid number 59 (Asp) or 62 (Leu) of SEQ ID NO:3; (3) amino acid number 94 (Pro) or 95 (Gln) to amino acid number 100 (Gln) or 103 (Met) of SEQ ID NO:3; (4) amino acid number 113 (Leu) to amino acid number 118 (Ser) or 119 (Thr) of SEQ ID NO:3; (5) amino acid number 123 (Glu) to amino acid number 126 (Asp) or 128 (His) of SEQ ID NO:3; and (6) amino acid number 134 (Gln) or 144 (Gly) to amino acid number 147 (Gly) of SEQ ID NO:3. Other antigens include huIL-TIF-1 (SEQ ID NO:34; comprising amino acid number 49 (Lys) to amino acid number 77 (Cys) of SEQ ID NO:3) or huIL-TIF-2 (SEQ ID NO:35; comprising amino acid number 89 (Glu) to amino acid number 101 (Pro) of SEQ ID NO:3) or huIL-TIF-3 (SEQ ID NO:36; comprising amino acid number 132 (Asn) to amino acid number 145 (Glu) of SEQ ID NO:3).

Antibodies from an immune response generated by inoculation of an animal with these antigens (or immunogens) can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a IL-TIF polypeptide or a fragment thereof. The immunogenicity of a IL-TIF polypeptide may be increased through the use of an adjuvant, such as alum (aluminum hydroxide) or Freund's complete or incomplete adjuvant. Polypeptides useful for immunization also include fusion polypeptides, such as fusions of IL-TIF or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-IL-TIF antibodies herein bind to a IL-TIF polypeptide, peptide or epitope with an affinity at least 10-fold greater than the binding affinity to control (non-IL-TIF) polypeptide. It is preferred that the antibodies exhibit a binding affinity ($K_a$) of $10^6$ $M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, G., Ann. NY Acad. Sci. 51: 660-672, 1949).

Whether anti-IL-TIF antibodies do not significantly cross-react with related polypeptide molecules is shown, for example, by the antibody detecting IL-TIF polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human IL-TIF, and IL-TIF mutant polypeptides. Moreover, antibodies can be "screened against" known related polypeptides, to isolate a population that specifically binds to the IL-TIF polypeptides. For example, antibodies raised to IL-TIF are adsorbed to related polypeptides adhered to insoluble matrix; antibodies specific to IL-TIF will flow through the matrix under the proper buffer conditions. Screening allows isolation of polyclonal and monoclonal antibodies non-cross-reactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies:*

*Principles and Practice*, Goding, J. W. (eds.), *Academic Press Ltd.*, 1996; Benjamin et al., *Ann. Rev. Immunol* 2: 67-101, 1984. Specifically binding anti-IL-TIF antibodies can be detected by a number of methods in the art, and disclosed below.

A variety of assays known to those skilled in the art can be utilized to detect antibodies which bind to IL-TIF proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant IL-TIF protein or polypeptide.

Alternative techniques for generating or selecting antibodies useful herein include in vitro exposure of lymphocytes to IL-TIF protein or peptide, and selection of antibody display libraries in phage or similar vectors (for instance, through use of immobilized or labeled IL-TIF protein or peptide). Genes encoding polypeptides having potential IL-TIF polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the IL-TIF sequences disclosed herein to identify proteins which bind to IL-TIF. These "binding polypeptides" which interact with IL-TIF polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of IL-TIF polypeptides; for detecting or quantitating soluble IL-TIF polypeptides as marker of underlying pathology or disease. These binding polypeptides can also act as IL-TIF "antagonists" to block IL-TIF binding and signal transduction in vitro and in vivo. These anti-IL-TIF binding polypeptides would be useful for inhibiting IL-TIF activity or protein-binding.

Antibodies to IL-TIF may be used for tagging cells that express IL-TIF; for isolating IL-TIF by affinity purification; for diagnostic assays for determining circulating levels of IL-TIF polypeptides; for detecting or quantitating soluble IL-TIF as a marker of underlying pathology or disease; in analytical methods employing FACS; for screening expression libraries; for generating anti-idiotypic antibodies; and as neutralizing antibodies or as antagonists to block IL-TIF activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to IL-TIF or fragments thereof may be used in vitro to detect denatured IL-TIF or fragments thereof in assays, for example, Western Blots or other assays known in the art.

Several anti-human-IL-TIF neutralizing monoclonal antibodies have been made and hybridomas expressing said neutralizing antibodies were deposited in the ATCC. Hybridomas expressing neutralizing monoclonal antibodies to human-IL-TIF were deposited and received on Mar. 5, 2003, with the American Type Tissue Culture Collection (ATCC; 10801 University Boulevard, Manassas, Va. 20110-2209) patent depository as original deposit under the Budapest Treaty and were given the following ATCC Accession Nos.: 266.16.1.4.4.1 (ATCC PTA-5035); 266.5.1.2.2.3 (ATCC PTA-5033); 267.17.1.1.4.1 (ATCC PTA-5038; 267.4.1.1.4.1 (ATCC PTA-5037); 266.12.6.1.3.2.1 (ATCC PTA-5034); 266.19.1.10.5.2 (ATCC PTA-5036 . Such antibodies can be humanized, and modified as described herein, and used therapeutically to treat psoriasis, psoriatic arthritis, IBD, colitis, endotoxemia as well as in other therapeutic applications described herein.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, IL-TIF polypeptides or anti-IL-TIF antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates. Such cytokine toxin fusion proteins can be used for in vivo killing of target tissues.

In another embodiment, IL-TIF cytokine fusion proteins or antibody-cytokine fusion proteins can be used for in vivo killing of target tissues (for example, leukemia, lymphoma, lung cancer, colon cancer, melanoma, pancreatic cancer, ovarian cancer, blood and bone marrow cancers, or other cancers wherein IL-TIF receptors are expressed) (See, generally, Hornick et al., *Blood* 89:4437-47, 1997). The described fusion proteins enable targeting of a cytokine to a desired site of action, thereby providing an elevated local concentration of cytokine. Suitable IL-TIF polypeptides or anti-IL-TIF antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the IL-TIF polypeptide or anti-IL-TIF antibody targets vascular cells or tissues, such polypeptide or antibody may be conjugated with a radionuclide, and particularly with a beta-emitting radionuclide, to reduce restenosis. Such therapeutic approaches pose less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Moreover, inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, rheumatoid arthritis, multiple sclerosis, inflammatory bowel disease, colitis, and the like), septic shock and multiple organ failure. Importantly, these diverse disease states share common inflammatory mediators. The collective diseases that are characterized by inflammation have a large impact on human morbidity and mortality. Therefore it is clear that anti-inflammatory antibodies and binding polypeptides, such as anti-IL-TIF antibodies and binding polypeptides described herein, could have crucial therapeutic potential for a vast number of human and animal diseases, from asthma and allergy to autoimmunity and septic shock. As such, use of anti-inflammatory anti IL-TIF antibodies and binding polypeptides described herein can be used therapeutically as IL-TIF antagonists described herein, particularly in diseases such as arthritis, endotoxemia, inflammatory bowel disease, psoriasis, related disease and the like.

1. Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides, such as anti-IL-TIF antibodies and binding polypeptides of the present invention. For Example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be IL-9 or IL-TIF, and as such a molecule that binds or inhibits IL-TIF, such as anti IL-TIF antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol* 89:9784-788, 1992; Myers et al., *Life Sci.* 61:1861-78, 1997; and Wang et al., *Immunol* 92:8955-959, 1995).

The administration of soluble zcytor16 comprising polypeptides, such as zcytor16-Fc4 or other zcytor16 soluble and fusion proteins to these CIA model mice was used to evaluate the use of zcytor16 to ameliorate symptoms and alter the course of disease. Since the ligand of zcytor16, IL-TIF, induces production of SAA, which is implicated in the pathogenesis of rheumatoid arthritis, and zcytor16 was demonstrated to be able to inhibit IL-TIF and SAA activity in vitro and in vivo, the systemic or local administration of zcytor16 comprising polypeptides, such as zcytor16-Fc4 or other zcytor16 soluble and fusion proteins can potentially suppress the inflammatory response in RA. The injection of 10 µg zcytor16-Fc (three times a week for 4 weeks) significantly reduced the disease score (paw score, incident of inflammation or disease). Other potential therapeutics include Zcytor16 polypeptides, soluble zcytor11/CRF2-4 receptor polypeptides, or anti IL-TIF antibodies or binding partners of the present invention, and the like.

One group has shown that an anti-mouse IL-TIF antibody may reduce symptoms in a mouse CIA-model relative to control mice, thus showing conceptually that neutralizing antibodies to IL-TIF may be beneficial in treating human disease. The administration of a single mouse-IL-TIF-specific rat monoclonal antibody (P3/1) reduced the symptoms of arthritis in the animals when introduced prophylactically or after CIA-induced arthritis was induced in the model (WIPO Publication 02/068476; published Sep. 9, 2002). Therefore, the anti-IL-TIF antibodies of the present invention, including the neutralizing anti-human IL-TIF antibodies of the present invention, can be used to neutralize IL-TIF in the treatment of specific human diseases such as psoriasis, psoriatic arthritis, arthritis, endotoxemia, inflammatory bowel disease (IBD), colitis, and other inflammatory conditions disclosed herein.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory antibodies and binding polypeptides, such as anti-IL-TIF antibodies and binding polypeptides of the present invention, could aid in preventing and treating endotoxemia in humans and animals. Zcytor16 polypeptides, soluble zcytor11/CRF2-4 receptor polypeptides, or anti IL-TIF antibodies or binding partners, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that 1ug injection of *E. coli* LPS into a C57B1/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF.

The administration of soluble zcytor16 comprising polypeptides, such as zcytor16-Fc4 or other zcytor16 soluble and fusion proteins to these LPS-induced model was used to evaluate the use of zcytor16 to ameliorate symptoms and alter the course of LPS-induced disease. The model showed induction of IL-TIF by LPS injection and the potential treatment of disease by zcytor16 polypeptides. Since LPS induces the production of pro-inflammatory IL-TIF, SAA or other pro-inflammatory factors possibly contributing to the pathology of endotoxemia, the neutralization of IL-TIF activity, SAA or other pro-inflammatory factors by its antagonist zcytor16 polypeptide can be used to reduce the symptoms of endotoxemia, such as seen in endotoxic shock. Other potential therapeutics include Zcytor16 polypeptides, soluble zcytor11/CRF2-4 receptor polypeptides, or anti IL-TIF antibodies or binding partners of the present invention, and the like.

3. Inflammatory Bowel Disease. IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. Zcytor16 polypeptides, soluble zcytor11/CRF2-4 receptor polypeptides, or anti IL-TIF antibodies or binding partners, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of soluble zcytor16 comprising polypeptides, such as zcytor16-Fc4 or other zcytor16 soluble and fusion proteins to these TNBS or DSS models can be used to evaluate the use of zcytor16 to ameliorate symptoms and alter the course of gastrointestinal disease. We observed the increased expression of IL-TIF in colon tissues of DSS-mice by RT-PCR, and the synergistic activity of IL-TIF with IL-1beta on intestinal cell lines. It indicates IL-TIF may play a role in the inflammatory response in colitis, and the neutralization of IL-TIF activity by administrating zcytor16 polypeptides is a potential therapeutic approach for IBD. Other potential therapeutics include Zcytor16 polypeptides, soluble zcytor11/CRF2-4 receptor polypeptides, or anti IL-TIF antibodies or binding partners of the present invention, and the like.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. Zcytor16 polypeptides, soluble zcytor11/CRF2-4 receptor polypeptides, or anti IL-TIF antibodies or binding partners, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

IL-20 is a novel IL-10 homologue that causes neonatal lethality with skin abnormalities including aberrant epidermal differentiation in IL-20 transgenic mice (Blumberg H et al., *Cell* 104:9-19, 2001) IL-20 receptor is dramatically upregulated in psoriatic skin. Since IL-TIF shares a receptor subunit (zcytor11) with IL-20 receptor, and IL-TIF transgenic mice display a similar phenotype, it is possible that IL-TIF is also involved in the inflammatory skin diseases such as psoriasis. The administration of zcytor16 polypeptide, either subcutaneous or topically, may potential reduce the inflammation and symptom. Other potential therapeutics include Zcytor16 polypeptides, soluble zcytor11/CRF2-4 receptor polypeptides, or anti IL-TIF antibodies or binding partners of the present invention, and the like.

IL-TIF has been shown to be induced in the presence of IL-9, and is suspected to be involved in promoting Th1-type immune responses, and inflammation. IL-9 stimulates proliferation, activation, differentiation and/or induction of immune function in a variety of ways and is implicated in asthma, lung mastocytosis, and other diseases, as well as activates STAT pathways. Antagonists of IL-TIF or IL-9 function can have beneficial use against such human diseases. The present invention provides such novel antagonists of IL-TIF.

IL-TIF has been show to be involved in up-regulate the production of acute phase reactants, such as serum amyloid A (SAA), α1-antichymotrypsin, and haptoglobin, and that IL-TIF expression is increased upon injection of lipopolysaccharide (LPS) in vivo suggesting that IL-TIF is involved in inflammatory response (Dumoutier, L. et al., *Proc. Nat'l. Acad. Sci.* 97:10144-10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, *J. Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, as IL-TIF acts as a pro-inflammatory molecule and induces production of SAA, antagonists would be useful in treating inflammatory disease and other diseases associated with acute phase response proteins induced by IL-TIF. Such antagonists are provided by the present invention. For example, method of reducing IL-TIF-induced or IL-9 induced inflammation comprises administering to a mammal with inflammation an amount of a composition of anti-IL-TIF antibody or binding polypeptide sufficient to reduce inflammation. Moreover, a method of suppressing an inflammatory response in a mammal with inflammation can comprise: (1) determining a level of serum amyloid A protein; (2) administering a composition comprising an anti-IL-TIF antibody or binding polypeptides described herein in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Over expression of IL-TIF was shown in human psoriatic lesions, suggesting that IL-TIF is involved in human psoriasis. Moreover, as described herein, over expression of IL-TIF in transgenic mice showed epidermal thickening and immune cell involvement indicative of a psoriatic phenotype, and in addition injection of IL-TIF into normal mice showed epidermal thickening and immune cell involvement indicative of a psoriatic phenotype which was ablated by the soluble receptor antagonist zcytor16. Such in vivo data further suggests that the pro-inflammatory IL-TIF is involved in psoriasis. As such, antagonists to IL-TIF activity, such as the anti-human-IL-TIF monoclonal antibodies of the present invention, as well as soluble receptors and antibodies thereto, are useful in therapeutic treatment of inflammatory diseases, particularly as antagonists to IL-TIF in the treatment of psoriasis. Moreover, antagonists to IL-TIF activity, such as the anti-human-IL-TIF monoclonal antibodies of the present invention, as well as soluble receptors and antibodies thereto, are useful in therapeutic treatment of other inflammatory diseases for example as antagonists to IL-TIF in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

Moreover, anti-IL-TIF antibodies of the present invention can be used in the prevention and therapy against weight loss associated with a number of inflammatory diseases described herein, as well as for cancer (e.g., chemotherapy and cachexia), and infectious diseases. For example, severe weight loss is a key marker associated with models for septicemia, MS, RA, and tumor models. In addition, weight loss is a key parameter for many human diseases including cancer, infectious disease and inflammatory disease. Weight loss was shown in mice injected with IL-TIFAdenovirus described herein. Anti-IL-TIF antibodies and IL-22 antagonists such as soluble zcytor11 receptors and antibodies thereto, as well as zcytor16 receptors, can be tested for their ability to prevent and treat weight loss in mice injected with IL-TIF andenovires described herein. Methods of determining a prophylactic or therapeutic regimen for such IL-22 antagonists is known in the art and can be determined using the methods described herein.

IL-TIF is implicated in inducing inflammatory response including induction of the acute-phase response (Dumoutier, L. et al., *Proc. Nat'l. Acad. Sci.* 97:10144-10149, 2000). Thus, particular embodiments of the present invention are directed toward use of anti-IL-TIF antibodies and binding polypeptides as antagonists in inflammatory and immune diseases or conditions such as psoriasis, arthritis, pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, toxic shock syndrome, endotoxemia, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-TIF or IL-9 cytokine production is desired.

Moreover, anti-IL-TIF antibodies and binding polypeptides described herein are useful to:

Antagonize IL-TIF directly or block signaling via the IL-TIF receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

Antagonize IL-TIF directly or block signaling via the IL-TIF receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via zcytor16 (Hughes C et al., *J. Immunol* 153: 3319-3325, 1994). Alternatively antibodies, such as monoclonal antibodies (MAb) to zcytor16-comprising receptors, can also be used as an antagonist to deplete unwanted immune cells to treat autoimmune disease. Asthma, allergy and other atopic disease may be treated with an MAb against, for example, anti-IL-TIF monoclonal antibody to inhibit the immune response or to deplete offending cells. Blocking or inhibiting signaling via IL-TIF receptors, using the antibodies and binding partners of the present invention, may also benefit diseases of the pancreas, kidney, pituitary and neuronal cells. IDDM, NIDDM, pancreatitis, and pancreatic carcinoma may benefit. Anti-IL-TIF antibodies and binding polypeptides may serve as a target for MAb therapy of cancer where an antagonizing MAb inhibits cancer growth and targets immune-mediated killing. (Holliger P, and Hoogenboom, H: *Nature Biotech.* 16: 1015-1016, 1998). Mabs IL-TIF may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

Soluble zcytor16 monomeric, homodimeric, heterodimeric and multimeric polypeptides described herein can be used to neutralize/block IL-TIF activity in the treatment of autoimmune disease, atopic disease, NIDDM, pancreatitis and kidney dysfunction, and inflammatory diseases, as described above.

The anti-IL-TIF antibodies and binding polypeptides of the present invention are useful as antagonists of the IL-TIF cytokine. Such antagonistic effects can be achieved by direct neutralization or binding of the IL-TIF. In addition to antagonistic uses, the anti-IL-TIF antibodies and binding polypeptides of the present invention can bind IL-TIF and act as carrier proteins for the IL-TIF cytokine, in order to transport the Ligand to different tissues, organs, and cells within the body. As such, the anti-IL-TIF antibodies and binding polypeptides of the present invention can be fused or coupled to molecules, polypeptides or chemical moieties that direct the soluble-receptor-Ligand complex to a specific site, such as a tissue, specific immune cell, or tumor. For example, in acute infection or some cancers, benefit may result from induction of inflammation and local acute phase response proteins by the action of IL-TIF. Thus, the anti-IL-TIF antibodies and binding polypeptides of the present invention can be used to specifically direct the action of the IL-TIF. See, Cosman, D. *Cytokine* 5: 95-106, 1993; and Fernandez-Botran, R. *Exp. Opin. Invest. Drugs* 9:497-513, 2000.

Moreover, the anti-IL-TIF antibodies and binding polypeptides of the present invention can be used to stabilize the IL-TIF, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Fernandez-Botran, R. supra. Moreover, anti-IL-TIF antibodies and binding polypeptides can be combined with a cognate ligand such as IL-TIF to comprise a ligand/antibody complex. Such complexes may be used to stimulate responses from cells presenting a companion receptor subunit such as, for example, zcytor11 or CRF2-4. The cell specificity of zcytor16/ligand complexes may differ from that seen for the ligand administered alone. Furthermore the complexes may have distinct pharmacokinetic properties such as affecting half-life, dose/response and organ or tissue specificity. ZcytoR16/IL-TIF complexes thus may have agonist activity to enhance an immune response or stimulate mesangial cells or to stimulate hepatic cells. Alternatively only tissues expressing a signaling subunit the heterodimerizes with the complex may be affected analogous to the response to IL6/IL6R complexes (Hirota H. et al., *Proc. Nat'l. Acad. Sci.* 92:4862-4866, 1995; Hirano, T. in Thomason, A. (Ed.) "The Cytokine Handbook", $3^{rd}$ Ed., p. 208-209). Soluble receptor/cytokine complexes for IL12 and CNTF display similar activities.

IL-TIF was isolated from tissue known to have important immunological function and which contain cells which play a role in the immune system. IL-TIF ligand is expressed in CD3+ selected, activated peripheral blood cells. This suggests that IL-TIF expression may be regulated and increase after T cell activation. Moreover, IL-TIF polypeptides may have an effect on the growth/expansion and/or differentiated state of T- or B-Cells, T- or B-cell progenitors, NK cells or NK progenitors. Moreover, IL-TIF can effect proliferation and/or differentiation of T cells and B cells in vivo. Factor that both stimulate proliferation of hematopoietic progenitors and activate mature cells are generally known. NK cells are responsive to IL-2 alone, but proliferation and activation generally require additional growth factors. For example, it has been shown that IL-7 and Steel Factor (c-kit ligand) were required for colony formation of NK progenitors. IL-15+IL-2 in combination with IL-7 and Steel Factor was more effective (Mrozek et al., *Blood* 87:2632-2640, 1996). However, unidentified cytokines may be necessary for proliferation of specific subsets of NK cells and/or NK progenitors (Robertson et. al., *Blood* 76:2451-2438, 1990). A composition comprising IL-TIF and IL-15 may stimulate NK progenitors and NK cells, as a composition that is more potent than previously described factors and combinations of factors. Similarly, such combinations of factors that include IL-TIF may also affect other hematopoietic and lymphoid cell types, such as T-cells, B-cells, macrophages, dendritic cells, and the like. Antibodies or binding polypeptides of the present invention can be used or assayed by showing antagonism or inhibition of such activities.

Most four-helix bundle cytokines as well as other proteins produced by activated lymphocytes play an important biological role in cell differentiation, activation, recruitment and homeostasis of cells throughout the body. Therapeutic utility includes treatment of diseases which require immune regulation including autoimmune diseases, such as, rheumatoid arthritis, multiple sclerosis, myasthenia gravis, systemic lupus erythomatosis (SLE) and diabetes. IL-TIF may be important in the regulation of inflammation, and therefore effectors, such as antagonist antibodies of the present invention would be useful in treating rheumatoid arthritis, asthma, ulcerative colitis, inflammatory bowel disease, Crohn's disease, psoriasis, pancreatitis, and sepsis. There may be a role of IL-TIF in mediating tumor cell killing and therefore would be useful in the treatment of cancer such as ovarian cancer, lung cancer, melanoma, and colon cancer. IL-TIF may be a potential therapeutic in suppressing the immune system which would be important for reducing graft rejection. IL-TIF may have usefulness in prevention of graft-vs-host disease.

The IL-TIF can also be used ex vivo, such as in autologous marrow culture. Briefly, bone marrow is removed from a patient prior to chemotherapy or organ transplant and treated with IL-TIF, optionally in combination with one or more other cytokines. The treated marrow is then returned to the patient after chemotherapy to speed the recovery of the marrow or after transplant to suppress graft vs. Host disease. In addition, the IL-TIF can also be used for the ex vivo expansion of marrow or peripheral blood progenitor (PBPC) cells. Prior to treatment, marrow can be stimulated with stem cell factor (SCF) to release early progenitor cells into peripheral circulation. These progenitors can be collected and concentrated from peripheral blood and then treated in culture with IL-TIF, optionally in combination with one or more other cytokines, including but not limited to IL-10, zcyto10, MDA7, SCF, IL-2, IL-4, IL-7 or IL-15, to differentiate and proliferate into high-density lymphoid cultures, which can then be returned to the patient following chemotherapy or transplantation.

Alternatively, IL-TIF may activate the immune system which would be important in boosting immunity to infectious diseases, treating immunocompromised patients, such as HIV+ patients, or in improving vaccines. In particular, IL-TIF stimulation or expansion of T-cells, B-cells, NK cells, and the like, or their progenitors, would provide therapeutic value in treatment of viral infection, and as an anti-neoplastic factor. NK cells are thought to play a major role in elimination of metastatic tumor cells and patients with both metastases and solid tumors have decreased levels of NK cell activity (Whiteside et. al., *Curr. Top. Microbiol. Immunol* 230:221-244, 1998).

Further analysis of mice injected with IL-TIF adenovirus reveals that albumin levels are reduced relative to control adenovirus injected animals, and glucose levels are depressed significantly. However liver enzymes (ALT and AST) are at similar levels to those seen for mice injected with control adenovirus. IL-TIF may specifically inhibit or alter liver cell functions. Alternatively excess IL-TIF may synergize with viral infection leading to adverse effects on the liver. Thus antagonists (antibodies, muteins, soluble receptors) may be useful to treat viral disease. Especially viral diseases that target the liver such as: Hepatitis B, Hepatitis C and Adenovirus. Viral disease in other tissues may be treated with antagonists to IL-TIF, for example viral meningitis, and HIV-related disease.

Mice injected with IL-TIF adenovirus display weight-loss, loss of mobility and a failure to groom, and a reduction in circulating lymphocytes. These changes are typical of those seen during septic shock and other inflammatory conditions. These effects may be caused directly by IL-TIF or indirectly by induction of elevated levels of proinflammatory cytokines such as IL-1, TNFα, and IL-6. Antagonists to IL-TIF may be useful to treat septic shock, adult respiratory distress syndrome, endotoxemia, and meningitis. Other diseases that may benefit from IL-TIF antagonists include: Hemorrhagic shock, disseminated intravascular coagulopathy, myocardial ischemia, stroke, rejection of transplanted organs, pulmonary fibrosis, inflammatory hyperalgesia and cachexia.

Mice injected with IL-TIF adenovirus display reduced numbers of peripheral blood lymphocytes. This is likely to be a direct inhibitory effect of IL-TIF on peripheral blood lymphocytes. Antagonizing IL-TIF may promote lymphocyte maintenance and growth especially when they are needed to eradicate bacterial, viral or parasitic pathogens. Thus antagonizing IL-TIF may benefit patients with: Tuberculosis, cryptogenic fibrosing alveolitis, pneumonia, meningococal disease, AIDS, HIV-related lung disease, hepatitis, viral meningitis, malaria, and dysentery (*Shigella dysenteriae*).

The lymphocyte inhibitory effects of IL-TIF may be used to reduce autoimmunity and to inhibit the growth of lymphoma tumors, especially non-Hodgkin's lymphoma and lymphoid leukemias. IL-TIF may also be used to inhibit lymphocytes and promote graft acceptance for organ transplant patients. Kidney and bone marrow grafts would be suitable indications.

Mice injected with IL-TIF adenovirus display significantly increased numbers of platelets. Mild bleeding disorders (MBDs) associated with platelet dysfunctions are relatively common (Bachmann, *Seminars in Hematology* 17: 292-305, 1980), as are a number of congenital disorders of platelet function, including Bernard-Soulier syndrome (deficiency in platelet GPIb), Glanzmann's thrombasthenia (deficiency of GPIIb and GPIIIa), congenital afibrinogenemia (diminished or absent levels of fibrinogen in plasma and platelets), and gray platelet syndrome (absence of a-granules). In addition there are a number of disorders associated with platelet secretion, storage pool deficiency, abnormalities in platelet arachidonic acid pathway, deficiencies of platelet cyclooxygenase and thromboxane synthetase and defects in platelet activation (reviewed by Rao and Holmsen, *Seminars in Hematology* 23: 102-118, 1986).

IL-TIF was shown to increase platelet and neutrophils in vivo in animals, and can be used therapeutically wherever it is desirable to increase the level of platelets and neutrophils, such as in the treatment of cytopenia, such as that induced by aplastic anemia, myelodisplastic syndromes, chemotherapy or congenital cytopenias. The proteins are also useful for increasing platelet production, such as in the treatment of thrombocytopenia. Thrombocytopenia is associated with a diverse group of diseases and clinical situations that may act alone or in concert to produce the condition. Lowered platelet counts can result from, for example, defects in platelet production, abnormal platelet distribution, dilutional losses due to massive transfusions, or abnormal destruction of platelets. For example, chemotherapeutic drugs used in cancer therapy may suppress development of platelet progenitor cells in the bone marrow, and the resulting thrombocytopenia limits the chemotherapy and may necessitate transfusions. In addition, certain malignancies can impair platelet production and platelet distribution. Radiation therapy used to kill malignant cells also kills platelet progenitor cells. Thrombocytopenia may also arise from various platelet autoimmune disorders induced by drugs, neonatal alloimmunity or platelet transfusion alloimmunity. The IL-TIF can reduce or eliminate the need for transfusions, thereby reducing the incidence of platelet alloimmunity Abnormal destruction of platelets can result from: (1) increased platelet consumption in vascular grafts or traumatized tissue; or (2) immune mechanisms associated with, for example, drug-induced thrombocytopenia, idiopathic thrombocytopenic purpura (ITP), autoimmune diseases, hematologic disorders such as leukemia and lymphoma or metastatic cancers involving bone marrow. Other indications for the IL-TIF include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites.

Over expression of IL-TIF was shown in human psoriatic lesions, suggesting that IL-TIF is involved in human psoriasis. Moreover, as described herein, over expression of IL-TIF in transgenic mice showed epidermal thickening and immune cell involvement indicative of a psoriatic phenotype, and in addition injection of IL-TIF into normal mice showed epidermal thickening and immune cell involvement indicative of a psoriatic phenotype which was ablated by the soluble receptor antagonist zcytor16. Such in vivo data further suggests that the pro-inflammatory IL-TIF is involved in psoriasis. As such, antagonists to IL-TIF activity, such as the anti-human-IL-TIF monoclonal antibodies of the present invention, as well as soluble receptors and antibodies thereto, are useful in therapeutic treatment of inflammatory diseases, particularly as antagonists to IL-TIF in the treatment of psoriasis. Moreover, antagonists to IL-TIF activity, such as the anti-human-IL-TIF monoclonal antibodies of the present invention, as well as soluble receptors and antibodies thereto, are useful in therapeutic treatment of other inflammatory diseases for example as antagonists to IL-TIF in the treatment of atopic dermatitis, IBD, colitis, Endotoxemia, arthritis, rheumatoid arthritis, and psoriatic arthritis, adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

In utero administration of neutralizing anti-IL-TIF or IL-20 antibodies can be used to show efficacy in vivo in disease models by reducing or eliminating the skin phenotype found IL-TIF transgenic pups which over express IL-TIF, or IL-20 transgenic pups which over express IL-20. There are precedents in the art for in utero treatment with neutralizing monoclonal antibodies (mAbs). In one case, the development of the B-1 subset of B cells was dramatically affected by treating pregnant female mice with a mAb specific for the B cell-specific molecule, CD19 (e.g., Krop I. Et al., *Eur. J. Immunol.* 26(1):238-42, 1996). Krop et al. injected timed pregnant mice intraperitoneally with 500 ug of rat anti-mouse CD19 mAb (or a rat isotype-matched control Ab) in PBS beginning on day 9 of gestation, with subsequent injections every other day until birth. Pups were also injected once with 500 ug of these antibodies at 10 days of age. In another case, Tanaka et al., found that in utero treatment with monoclonal antibody to IL-2 receptor beta-chain completely abrogates development of Thy-1+ dendritic epidermal cells. The two distinct subunits of the IL-2 receptor, i.e. the alpha-chain (IL-2R alpha) and the beta-chain (IL-2R beta), are expressed in an almost mutually exclusive fashion throughout fetal thymus ontogeny. Blocking IL-2R beta, a signal transducing component of IL-2R, by administering a neutralizing mAb to IL-2R beta, resulted in the complete and selective disappearance of Thy-1+ skin dendritic epidermal cells. Development of any other T cell subsets was uncompromised. This indicated that IL-2 plays a crucial role in the development of fetal V gamma 5+ cells and their descendants (see, Tanaka, T. et al., *Int Immunol* 4(4):487-9, 1992). In addition, Schattemann G C et al., showed that PDGF-A is required for normal murine cardiovascular development using an in utero system. Several lines of evidence suggest that platelet-derived growth factor A chain (PDGF-A) is required for normal embryonic cardiovascular development. Introduction of anti-PDGF-A neutralizing antibodies into mouse deciduas in utero resulted in the selective disruption of PDGF-A ligand-receptor interactions in vivo for a period of 18-24 hr and allowed assessment of whether PDGF-A is required for cardiovascular development and when it is required (see, Schattemann G C et al., *Dev. Biol.* 176(1):133-42, 1996). These results, as well as others described in the art, provide evidence that neutralizing mAbs can elicit strong effects in utero. Similarly, data showing the efficacy of neutralizing IL-20 or IL-22 (IL-TIF) with monoclonal antibodies in vivo in disease models to reduce or eliminate the skin phenotype found in IL-20 and IL-22 (IL-TIF) transgenic pups which over express IL-20 and IL-22 (IL-TIF) respectively can be shown. These transgenic mice are born with a "shiny" skin appearance, due at least in part to a thickening of the epidermis as described herein. The IL-20 TG pups expressing fairly low levels of the transgenic cytokine can recover and do survive to breed, but the IL-TIF TG mice die shortly after birth, generally before 5 days of age.

For pharmaceutical use, the IL-TIF are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, the hematopoietic IL-TIF may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of IL-TIF is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The IL-TIF can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

The IL-TIF can also be used ex vivo, such as in autologous marrow culture or liver cultures. For example, briefly, bone marrow is removed from a patient prior to chemotherapy and treated with IL-TIF, optionally in combination with one or more other cytokines. The treated marrow is then returned to the patient after chemotherapy to speed the recovery of the marrow. In addition, the IL-TIF can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with IL-TIF, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy. Such ex vivo uses are especially desirable in the instance that systemic administration is not tolerated by a patient. Thus the present invention to provide methods for stimulating the production of platelets and neutrophils in mammals including humans. The invention provides methods for stimulating platelet and neutrophil production in a mammal, ex vivo tissue sample, or cell cultures. The methods comprise administering to a mammal, ex vivo tissue sample, or cell culture a therapeutically effective amount of a hematopoietic protein selected from the group consisting of (a) proteins comprising the sequence of amino acids of SEQ ID NO:3 from amino acid residue 22 to amino acid residue 167; (b) allelic variants of (a); and (d) species homologs of (a) or (b), wherein the protein stimulates proliferation or differentiation of myeloid or lymphoid precursors, or the production of platelets, in combination with a pharmaceutically acceptable vehicle.

Moreover, the increase of platelets and neutrophils is desirable at a wound site not only in patients with blood diseases or undergoing chemotherapy as described above, but under normal conditions. A polypeptide such as IL-TIF, that increases platelet levels in vivo, can be used in topological formulations including gels, meshes, poultices, liquids, and the like to aid in the healing of common cuts, burns, lacerations, abrasions, and the like. Moreover, such applications can be applied in any instance where the healing of skin, muscle, or the like is desired, even internally, such as after surgery.

The IL-TIF are also valuable tools for the in vitro study of the differentiation and development of hematopoietic cells, such as for elucidating the mechanisms of cell differentiation and for determining the lineages of mature cells, and may also find utility as proliferative agents in cell culture.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42-46, 1988). Markers for mesenchymal stem cells have not been well identified (Owen et al., *J. of Cell Sci.* 87:731-738, 1987), so identification is usually made at the progenitor and mature cell stages. Il-TIF may be useful for studies to isolate mesenchymal stem cells and myocyte or other progenitor cells, both in vivo and ex vivo.

Assays measuring differentiation include, for example, measuring cell markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses,* 161-171, 1989; all incorporated herein by reference). Alternatively, IL-TIF polypeptide itself can serve as an additional cell-surface or secreted marker associated with stage-specific expression of a tissue. As such, direct measurement of IL-TIF polypeptide, or its loss of expression in a tissue as it differentiates, can serve as a marker for differentiation of tissues. Antibodies of the present can hence be used diagnostically as markers for cancer and inflammatory diseases as discussed herein.

Similarly, direct measurement of IL-TIF polypeptide, or its loss of expression in a tissue can be determined in a tissue or cells as they undergo tumor progression. Increases in invasiveness and motility of cells, or the gain or loss of expression of IL-TIF in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to IL-TIF expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, IL-TIF gain or loss of expression may serve as a diagnostic for prostate and other cancers. Hence antibodies of the present can hence be used diagnostically as markers for cancer and inflammatory diseases as discussed herein.

Moreover, the activity and effect of IL-TIF on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing IL-TIF, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., IL-TIF, on the ability of the tumor to recruit vasculature and undergo metastasis can thus be assessed. In addition, aside from using adenovirus, the implanted cells can be transiently transfected with IL-TIF. Use of stable IL-TIF transfectants as well as use of induceable promoters to activate IL-TIF expression in vivo are known in the art and can be used in this system to assess IL-TIF induction of metastasis. Moreover, purified IL-TIF or IL-TIF conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

The IL-TIF gene is present on a human chromosome, chromosome 12, and can therefore be used to determine whether a chromosome 12 aberration or if a mutation has occurred. Based on annotation of a fragment of human genomic DNA containing a part of IL-TIF genomic DNA (Genbank Accession No. AC007458), IL-TIF is located at the 12q15 region of chromosome 12. Detectable chromosomal aberrations at the IL-TIF gene locus include, but are not limited to, aneuploidy, gene copy number changes, loss of heterozygosity (LOH), translocations, insertions, deletions, restriction site changes and rearrangements. Such aberrations can be detected using IL-TIF polynucleotides by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

IL-TIF is located at the 12q15 region of chromosome 12. Another T-cell expressed cytokine, interferon-gamma (IFN-γ) maps near this locus (12q14), suggesting that the 12q14-15 locus is an important region for T-cell expressed cytokines. Moreover, mutations in IFN-γ are associated with immunodeficiency (See, e.g., Tzoneva, M. et al., *Clin. Genet.* 33:454-456, 1988). Mutations in IL-TIF, are likely to cause human disease as well, such as immunodeficiency, autoimmune disease, lymphoid cell cancers, or other immune dysfunction. Moreover, there are several genes that map to the IL-TIF locus that are associated with human disease states, such as cancer. 12q13-q15 region is involved in a variety of malignant and benign solid tumors (including salivary adenomas and uterine leiomyomas), with 12q15 as a common break point. Moreover, the high mobility group protein isoform I-C (HMGIC) maps to 12q15 and is involved in benign lipomas and other tumors. As IL-TIF maps to 12q15 as well, there can be an association between loss of IL-TIF function and tumor formation or progression. Moreover, translocations in 12q13-15 are prevalent in soft tissue tumors, multiple lipomatosis and malignant mixoid liposarcoma. IL-TIF polynucleotide probes can be used to detect abnormalities or genotypes associated with these cancer susceptibility markers. Because there is abundant evidence for cancer resulting from mutations in the 12q15 region, and IL-TIF also maps to this chromosomal locus, mutations in IL-TIF may also be directly involved in or associated with cancers, such as lymphoid cell cancers or other tumors.

A diagnostic could assist physicians in determining the type of disease and appropriate associated therapy, or assistance in genetic counseling. As such, the inventive anti-IL-TIF antibodies, polynucleotides, and polypeptides can be used for the detection of IL-TIF polypeptide, mRNA or anti-IL-TIF antibodies, thus serving as markers and be directly used for detecting or genetic diseases or cancers, as described herein, using methods known in the art and described herein. Further, IL-TIF polynucleotide probes can be used to detect abnormalities or genotypes associated with chromosome 12q15 deletions and translocations associated with human diseases, such as multiple lipomatosis and malignant mixoid liposarcoma (above), or other translocations involved with malignant progression of tumors or other 12q15 mutations, which are expected to be involved in chromosome rearrangements in malignancy; or in other cancers. Similarly, IL-TIF polynucleotide probes can be used to detect abnormalities or genotypes associated with chromosome 12q15 trisomy and chromosome loss associated with human diseases or spontaneous abortion. Moreover, amongst other genetic loci, those for Scapuloperoneal spinal muscular atrophy (12g13.3-q15), mucopolysaccaridosis (12q14), pseudo-vitamin D deficiency Rickets as a result of mutation in Cytochrome CYP27B1 (12q14) and others, all manifest themselves in human disease states as well as map to this region of the human genome. See the Online Mendellian Inheritance of Man (OMIM™, National Center for Biotechnology Information, National Library of Medicine. Bethesda, MD) gene map, and references therein, for this region of chromosome 3 on a publicly available WWW server. All of these serve as possible candidate genes for an inheritable disease which show linkage to the same chromosomal region as the IL-TIF gene. Thus, IL-TIF polynucleotide probes can be used to detect abnormalities or genotypes associated with these defects.

As discussed above, defects in the IL-TIF gene itself may result in a heritable human disease state. Molecules of the present invention, such as the polypeptides, antagonists, agonists, polynucleotides and antibodies of the present invention would aid in the detection, diagnosis prevention, and treatment associated with a IL-TIF genetic defect. In addition, IL-TIF polynucleotide probes can be used to detect allelic differences between diseased or non-diseased individuals at the IL-TIF chromosomal locus. As such, the IL-TIF sequences and antibodies can be used as diagnostics in forensic DNA profiling. Antibodies or binding polypeptides of the present invention can be used to antagonize or inhibit aberrant activities or overexpression of IL-TIF related to genetic disease resulting in IL-TIF abnormalities.

In general, the diagnostic methods used in genetic linkage analysis, to detect a genetic abnormality or aberration in a patient, are known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mice engineered to express the IL-TIF gene, referred to as "transgenic mice," and mice that exhibit a complete absence of IL-TIF gene function, referred to as "knockout mice," may also be generated (Snouwaert et al., *Science* 257:1083, 1992; Lowell et al., *Nature* 366:740-42, 1993; Capecchi, M. R., *Science* 244: 1288-1292, 1989; Palmiter, R. D. et al. *Annu Rev Genet.* 20: 465-499, 1986). For example, transgenic mice that over-express IL-TIF, either ubiquitously or under a tissue-specific or tissue-restricted promoter can be used to ask whether over-expression causes a phenotype. For example, over-expression of a wild-type IL-TIF polypeptide, polypeptide fragment or a mutant thereof may alter normal cellular processes, resulting in a phenotype that identifies a tissue in which IL-TIF expression is functionally relevant and may indicate a therapeutic target for the IL-TIF, its agonists or antagonists. For example, a preferred transgenic mouse to engineer is one that over-expresses the mature IL-TIF polypeptide (amino acid residues 23 (Pro) to 167 (Ile) of SEQ ID NO:3). Moreover, such over-expression may result in a phenotype that shows similarity with human diseases. Similarly, knockout IL-TIF mice can be used to determine where IL-TIF is absolutely required in vivo. The phenotype of knockout mice is predictive of the in vivo effects of that a IL-TIF antagonist, such as those described herein, may have. The human or mouse IL-TIF cDNA can be used to generate knockout mice. These mice may be employed to study the IL-TIF gene and the protein encoded thereby in an in vivo system, and can be used as in vivo models for corresponding human diseases, e.g., inflammatory diseases. In addition such mice can be used to test the inhibitory and anti-inflammatory effects of antagonistic molecules of the present invention. Moreover, transgenic mice expression of IL-TIF antisense polynucleotides or ribozymes directed against IL-TIF, described herein, can be used analogously to transgenic mice described above. Studies may be carried out by administration of purified IL-TIF protein, as well.

Moreover, as described herein, over expression of IL-TIF in transgenic mice showed epidermal thickening and immune cell involvement indicative of a psoriatic phenotype, and in addition injection of IL-TIF into normal mice showed epidermal thickening and immune cell involvement indicative of a psoriatic phenotype which was ablated by the soluble receptor antagonist zcytor16. Such in vivo data further suggests that the pro-inflammatory IL-TIF is involved in psoriasis. As such, antagonists to IL-TIF activity, such as the anti-human-IL-TIF monoclonal antibodies of the present invention, as well as soluble receptors and antibodies thereto, are useful in therapeutic treatment of inflammatory diseases, particularly as antagonists to IL-TIF in the treatment of psoriasis. Moreover, antagonists to IL-TIF activity, such as the anti-human-IL-TIF monoclonal antibodies of the present invention, as well as soluble receptors and antibodies thereto, are useful in therapeutic treatment of other inflammatory diseases for example as antagonists to IL-TIF in the treatment of atopic dermatitis, IBD, colitis, Endotoxemia, arthritis, rheumatoid arthritis, and psoriatic arthritis, adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease For pharmaceutical use, the antibodies and binding polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a IL-TIF protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of IL-TIF is an amount sufficient to produce a clinically significant change in hematopoietic or immune function.

The present invention also contemplates chemically modified Anti-IL-TIF antibody and binding polypeptide compositions, in which a Anti-IL-TIF antibody and binding polypeptide is linked with a polymer. Illustrative Anti-IL-TIF antibodies and binding polypeptides are soluble polypeptides that lack a functional transmembrane domain, such as a polypeptide consisting of amino acid residues 22 to 231, or 28 to 231 of SEQ ID NO:2. Typically, the polymer is water soluble so that the Anti-IL-TIF antibody and binding polypeptide conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce Anti-IL-TIF antibody and binding polypeptide conjugates.

Anti-IL-TIF antibody and binding polypeptide conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A Anti-IL-TIF antibody or binding polypeptide conjugate can also comprise a mixture of such water-soluble polymers.

One example of a Anti-IL-TIF antibody or binding polypeptide conjugate comprises a Anti-IL-TIF antibody or binding polypeptide moiety and a polyalkyl oxide moiety attached to the N-terminus of the Anti-IL-TIF antibody or binding polypeptide moiety. PEG is one suitable polyalkyl oxide. As an illustration, Anti-IL-TIF antibody or binding polypeptide can be modified with PEG, a process known as "PEGylation." PEGylation of Anti-IL-TIF antibody or binding polypeptide can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, Anti-IL-TIF antibody or binding polypeptide conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a Anti-IL-TIF antibody or binding polypeptide polypeptide. An example of an activated PEG ester is PEG esterified to N-hydroxysuccinimide. As used herein, the term "acylation" includes the following types of linkages between Anti-IL-TIF antibody or binding polypeptide and a water soluble polymer: amide, carbamate, urethane, and the like. Methods for preparing PEGylated Anti-IL-TIF antibody or binding polypeptide by acylation will typically comprise the steps of (a) reacting a Anti-IL-TIF antibody or binding polypeptide polypeptide with PEG (such as a reactive ester of an aldehyde derivative of PEG) under conditions whereby one or more PEG groups attach to Anti-IL-TIF antibody or binding polypeptide, and (b) obtaining the reaction product(s). Generally, the optimal reaction conditions for acylation reactions will be determined based upon known parameters and desired results. For example, the larger the ratio of PEG:Anti-IL-TIF antibody or binding polypeptide, the greater the percentage of polyPEGylated Anti-IL-TIF antibody or binding polypeptide product.

The product of PEGylation by acylation is typically a polyPEGylated Anti-IL-TIF antibody or binding polypeptide product, wherein the lysine ε-amino groups are PEGylated via an acyl linking group. An example of a connecting linkage is an amide. Typically, the resulting Anti-IL-TIF antibody or binding polypeptide will be at least 95% mono-, di-, or tri-pegylated, although some species with higher degrees of PEGylation may be formed depending upon the reaction conditions. PEGylated species can be separated from unconjugated Anti-IL-TIF antibody or binding polypeptide polypeptides using standard purification methods, such as dialysis, ultrafiltration, ion exchange chromatography, affinity chromatography, and the like.

PEGylation by alkylation generally involves reacting a terminal aldehyde derivative of PEG with Anti-IL-TIF antibody or binding polypeptide in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of Anti-IL-TIF antibody or binding polypeptide monopolymer conjugates.

Reductive alkylation to produce a substantially homogenous population of monopolymer Anti-IL-TIF antibody or binding polypeptide conjugate molecule can comprise the steps of: (a) reacting a Anti-IL-TIF antibody or binding polypeptide with a reactive PEG under reductive alkylation conditions at a pH suitable to permit selective modification of the α-amino group at the amino terminus of the Anti-IL-TIF antibody or binding polypeptide, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer Anti-IL-TIF antibody or binding polypeptide conjugates, the reductive alkylation reaction conditions are those that permit the selective attachment of the water-soluble polymer moiety to the N-terminus of Anti-IL-TIF antibody or binding polypeptide. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:Anti-IL-TIF antibody or binding polypeptide need not be as large because more reactive groups are available. Typically, the pH will fall within the range of 3 to 9, or 3 to 6. This method can be employed for making anti-IL-TIF antibody or binding polypeptide-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to Anti-IL-TIF antibody or binding polypeptide will generally be in the range of 1:1 to 100:1. Typically, the molar ratio of water-soluble polymer to Anti-IL-TIF antibody or binding polypeptide will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)). This method can be employed for making anti-IL-TIF antibody or binding polypeptide-comprising homodimeric, heterodimeric or multimeric soluble receptor conjugates.

A pharmaceutical composition comprising Anti-IL-TIF antibodies or binding partners (or Anti-IL-TIF antibody fragments, antibody fusions, humanized antibodies and the like) can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in *Drug Delivery*," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Anti-IL-TIF neutralizing antibodies and binding partners with IL-TIF binding activity can be encapsulated within liposomes using standard techniques of protein microencapsulation (see, for example, Anderson et al., *Infect. Immun* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified Anti-IL-TIF antibody or binding partner, for example anti-Anti-IL-TIF antibodies linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington Pharmaceutical Sciences*, 19$^{th}$ Edition (Mack Publishing Company 1995), and by Ranade and Hollinger, *Drug Delivery Systems* (CRC Press 1996).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

The invention is further illustrated by the following non-limiting examples.

EXAMPLES

Example 1

Identification and Cloning IL-TIF

IL-TIF polynucleotide was obtained by PCR from tissue based on Northern Analysis (Example 2, below) and by further PCR using oligonucleotides ZC25,840 (SEQ ID NO:5) and ZC25,841 (SEQ ID NO:6) in a PCR using human mixed lymphocyte reaction (MLR) cDNA. Thermocycler conditions were as described in Example 2 below. The resulting 1082 bb full length sequence is disclosed in SEQ ID NO:1 and the corresponding amino acid sequence is shown in SEQ ID NO:2 and SEQ ID NO:3. The full length novel cytokine was designated IL-TIF.

Example 2

IL-TIF Tissue Distribution

Northerns were performed using Human Multiple Tissue Blots (MTN1, MTN2 and MTN3) from Clontech (Palo Alto, Calif.) to determine the tissue distribution of human IL-TIF. A 237 bp cDNA probe was obtained using the PCR. Oligonucleotides ZC25,838 (SEQ ID NO:7) and ZC25,839 (SEQ ID NO:8) were used as primers. Marathon cDNA, synthesized in-house using Marathon cDNA Kit (Clontech) and protocol, was used as a template. The following human tissue specific cDNAs were also used: lymph node, bone marrow, CD4+, CD8+, spleen, and MLR, along with human genomic DNA (Clontech). Thermocycler conditions were as follows: one cycle at 94° C. for 2 min.; 35 cycles of 94° C. for 15 sec., 62° C. for 20 sec., and 72° C. for 30 sec.; one cycle at 72° C. for 7 min.; followed by a 4° C. hold. The correct predicted band size (237 bp) was observed on a 4% agarose gel in CD4+ and MLR reactions, along with the genomic DNA reaction. A band was excised and purified using a Gel Extraction Kit (Qiagen, Chatsworth, Calif.) according to manufacturer's instructions. The cDNA was radioactively labeled using a Rediprime II DNA labeling kit (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution. Hybridization took place overnight at 55° C., using $2 \times 10^6$ cpm/ml labeled probe. The blots were then washed in 2×SSC and 0.1% SDS at room temperature, then with 2×SSC and 0.1% SDS at 65° C., followed by a wash in 0.1×SSC and 0.1% SDS at 65° C. The blots were exposed 5 days to Biomax MS film (Kodak, Rochester, N.Y.). No transcript signals were observed on the MTN blots after development.

A RNA Master Dot Blot (Clontech) that contained RNAs from various tissues that were normalized to 8 housekeeping genes was also probed and hybridized as described above. A signal was observed in genomic DNA. While a faint signal in lymph node and very faint signals in fetal liver, skeletal muscle, and placenta were observed it was inconclusive whether these signals were significantly above background.

Example 3

Identification of Cells Expressing IL-TIF Using RT-PCR

Specific human cell types were isolated and screened for IL-TIF expression by RT-PCR. B-cells were isolated from fresh human tonsils by mechanical disruption through 100 µm nylon cell strainers (Becton Dickinson Biosciences, Franklin Lakes, N.J.). The B-cell suspensions were enriched for CD19+ B-cells by positive selection with VarioMACS VS+magnetic column and CD19 microbeads (Miltenyi Biotec, Auburn, Calif.) as per manufacturer's instructions. T-cells were isolated from human apheresed blood samples. CD3+ T-cells were purified by CD3 microbead VarioMACS positive selection and monocytes were purified by VarioMACS negative selection columns (Miltenyi) as per manufacturer's instructions. Samples from each population were stained and analyzed by fluorescent antibody cell sorting (FACS) (Bectin Dickinson, San Jose, Calif.) analysis to determine the percent enrichment and resulting yields. CD19+ B-cells were approximately 96% purified, CD3+ T-cells were approximately 95% purified, and monocytes were approximately 96% purified.

RNA was prepared, using a standard method in the art, from all three cell types that were either resting or activated. RNA was isolated from resting cells directly from the column preparations above. The CD19+ and CD3+ cells were activated by culturing at 500,000 cells/ml in RPMI+10% FBS containing PMA 5 ng/ml (Calbiochem, La Jolla, Calif.) and Ionomycin 0.5 ug/ml (Calbiochem) for 4 and 24 hours. The monocytes were activated by culturing in RPMI+10% FBS containing LPS 10 ng/ml (Sigma St. Louis Mo.) and rhIFN-g 10 ng/ml (R&D, Minneapolis, Minn.) for 24 hours. Cells were harvested and washed in PBS. RNA was prepared from the cell pellets using RNeasy Midiprep™ Kit (Qiagen, Valencia, Calif.) as per manufacturer's instructions and first strand cDNA synthesis was generated with Superscript II™ Kit (GIBCO BRL, Grand Island, N.Y.) as per manufacturers protocol.

Oligos ZC25,838 (SEQ ID NO:7) and ZC25,840 (SEQ ID NO:5) were used in a PCR reaction to screen the above described samples for a 473 bp fragment corresponding to IL-TIF message. PCR amplification was performed with Taq Polymerase (BRL Grand Island N.Y.), and reaction conditions as follows: 35 cycles of 94° C. for 15 sec., 62° C. for 20 sec., 72° C. for 30 sec.; 1 cycle at 72° C. for 7 min.; and 4° C. soak. 5 ul of each 50 µl reaction volume was run on a 0.9% agarose 0.5XTBE gel to identify resultant products. Table 5 below describes the results. PCR products were scored as (−) for no product, (+) for expected PCR product visible, (++) increased presence of PCR product and (+++) being the strongest signal.

TABLE 5

Cells expressing IL-TIF using RT-PCR

| cDNA Source | Activation | PCR Product |
| --- | --- | --- |
| CD3+ cells | 0 hr resting | + |
|  | 4-hr activated | +++ |
| CD19+ cells | 4 hr activated | ++ |
|  | 24 hr activated | + |
| Monocytes | 24 hr activated | − |

These results indicated that IL-TIF message is present in resting CD3+ T-cells and increases with mitogenic activation. It also appears to be expressed by 4-hr activated human CD19+ B-cells and reduced in expression in 24 hr activated B-cells. There was no apparent message in activated monocytes.

Example 4

Identification of hIL-TIF Message in an Activated T-Cell Library

A. The vector for CD3+ Selected Library Construction

The vector for CD3+ selected library construction was pZP7NX. The pZP7NX vector was previously constructed as follows: The coding region for the DHFR selective marker in vector pZP7 was removed by DNA digestion with NcoI and PstI restriction enzymes (Boehringer Mannheim). The digested DNA was run on 1% agarose gel, cut out and gel purified using the Qiagen Gel Extraction Kit (Qiagen) as per manufacturer's instructions. A DNA fragment representing the coding region of Zeocin selective marker was amplified by PCR method with primers ZC13,946 (SEQ ID NO:9) and ZC13,945 (SEQ ID NO:10), and pZeoSV2(+) as a template. There are additional PstI and BclI restriction sites in primer ZC13,946 (SEQ ID NO:9), and additional NcoI and SfuI sites in primer ZC13,945 (SEQ ID NO:10). The PCR fragment was cut with PstI and NcoI restriction enzymes and cloned into pZP7 vector prepared by cleaving with the same two enzymes and subsequent gel purification. This vector was named pZP7Z. Then the Zeocin coding region was removed by DNA digestion of vector pZP7Z with BclI and SfuI restriction enzymes. The digested DNA was run on 1% agarose gel, cut out and gel purified, and then ligated with a DNA fragment of Neomycin coding region cut from pZem228 vector with the same restriction enzymes (BclI and SfuI).

This new vector was named pZP7N, in which the coding region for DHFR selective marker was replaced by the coding region for a Neomycin selective marker from vector pZem228. A stuffer fragment including an Xho1 site was added to pZP7N to create a vector suitable for high efficiency directional cloning of cDNA; this new vector was called pZP7NX. To prepare the vector for cDNA, 20 μg of pZP7NX was digested with 20 units of EcoR1 (Life Technologies Gaithersberg, Md.) and 20 units of Xho1 (Boehringer Mannheim Indianapolis, Ind.) for 5 hours at 37° C., then 68° C. for 15 minutes. The digest was then run on a 0.8% low melt agarose 1×TAE gel to separate the stuffer from the vector. The vector band was excised and digested with "beta-Agarase" (New England Biolabs, Beverly, Mass.) following the manufacturer's recommendations. After ethanol precipitation the digested vector was resuspended in water to 45 ng/ml in preparation for ligation of CD3+ selected cDNA library described below.

B. Preparation of Primary Human Activated Cd3+ Selected Cell cDNA Library

Approximately $1.5 \times 10^8$ primary human CD3+ selected cells stimulated in ionomycin/PMA were isolated by centrifugation after culturing at 37° C. for 13 hours. Total RNA was isolated from the cell pellet using the "RNeasy Midi" kit from Qiagen, Inc. (Valencia, Calif.). mRNA was isolated from 225 micrograms of total RNA using the "MPG mRNA purification kit" from CPG Inc. (Lincoln Park, N.J.). 3.4 micrograms of mRNA was isolated and converted to double stranded cDNA using the following procedure.

First strand cDNA from stimulated human CD3+ selected cells was synthesized as follows. Nine μl Oligo d(T)-selected poly(A) CD3+ RNA at a concentration of 0.34 μg/μl and 1.0 μl of 1 μg/μl first strand primer ZC18,698 (SEQ ID NO:11) containing an Xho1 restriction site were mixed and heated at 65° C. for 4 minutes and cooled by chilling on ice. First strand cDNA synthesis was initiated by the addition of 9 μl of first strand buffer (5× SUPERSCRIPT® buffer; Life Technologies), 4 μl of 100 mM dithiothreitol and 2 μl of a deoxynucleotide triphosphate solution containing 10 mM each of dATP, dGTP, dTTP and 5-methyl-dCTP (Pharmacia Biotech Inc.) to the RNA-primer mixture. The reaction mixture was incubated at 45° C. for 4 minutes followed by the addition of 8 μl of 200 U/μl SuperscriptII®, RNase H-reverse transcriptase (Life Technologies). The reaction was incubated at 45° C. for 45 minutes followed by an incubation ramp of 1° C. every 2 minutes to 50° C. where the reaction was held for 10 minutes. To denature any secondary structure and allow for additional extension of the cDNA the reaction was then heated to 70° C. for 2 minutes then dropped to 55° C. for 4 minutes after which 2 μl of SuperscriptII® RT was added and incubated an additional 15 minutes followed by a ramp up to 70° C. at 1 minute/1° C. Unincorporated nucleotides were removed from the cDNA by twice precipitating in the presence of 2 μg of glycogen carrier, 2.0 M ammonium acetate and 2.5 volume ethanol, followed by a 100 μl wash with 70% ethanol. The cDNA was resuspended in 98 μl water for use in second strand synthesis.

Second strand synthesis was performed on the first strand cDNA under conditions that promoted first strand priming of second strand synthesis resulting in DNA hairpin formation. The second strand reaction contained 98 μl of the first strand cDNA, 30 μl of 5× polymerase I buffer (100 mM Tris: HCl, pH 7.5, 500 mM KCl, 25 mM MgCl2, 50 mM (NH4)2SO4), 2 μl of 100 mM dithiothreitol, 6 μl of a solution containing 10 mM of each deoxynucleotide triphosphate, 5 μl of 5 mM b-NAD, 1 μl of 3 U/μl E. coli DNA ligase (New England Biolabs Inc.) and 4 μl of 10 U/μl E. coli DNA polymerase I (New England Biolabs Inc.). The reaction was assembled at room temperature and was incubated at room temperature for 2 minutes followed by the addition of 4 μl of 3.8 U/μl RNase H (Life Technologies). The reaction was incubated at 15° C. for two hours followed by a 15 minute incubation at room temperature. 10 μl of 1M TRIS pH7.4 was added to the reaction and extracted twice with phenol/chloroform and once with chloroform, the organic phases were then back extracted with 50 μl of TE (10 mM TRIS pH 7.4, 1 mM EDTA), pooled with the other aqueous and ethanol precipitated in the presence of 0.3 M sodium acetate. The pellet was washed with 100 μl 70% ethanol air dried and resuspended in 40 μl water.

The single-stranded DNA of the hairpin structure was cleaved using mung bean nuclease. The reaction mixture contained 40 μl of second strand cDNA, 5 μl of 10× mung bean nuclease buffer (Life technologies), 5 μl of mung bean nuclease (Pharmacia Biotech Corp.) diluted to 1 U/μl in 1× mung bean nuclease buffer. The reaction was incubated at 37° C. for 45 minutes. The reaction was terminated by the addition of 10 μl of 1 M Tris: HCl, pH 7.4 followed by sequential phenol/chloroform and chloroform extractions as described above. Following the extractions, the cDNA was ethanol precipitated in the presence of 0.3 M sodium acetate. The pellet was washed with 100 μl 70% ethanol air dried and resuspended in 38 μl water.

The resuspended cDNA was blunt-ended with T4 DNA polymerase. The cDNA, which was resuspended in 38 μl of water, was mixed with 12 μl 5×T4 DNA polymerase buffer (250 mM Tris:HCl, pH 8.0, 250 mM KCl, 25 mM MgCl2), 2 μl 0.1 M dithiothreitol, 6 μl of a solution containing 10 mM of each deoxynucleotide triphosphate and 2 μl of 1 U/μl T4 DNA polymerase (Boehringer Mannheim Corp.). After an incubation of 45 minutes at 15° C., the reaction was terminated by the addition of 30 μl TE followed by sequential phenol/chloroform and chloroform extractions and back extracted with 20 μl TE as described above. The DNA was ethanol precipitated in the presence of 2 μl Pellet Paint™ (Novagen) carrier and 0.3 M sodium acetate and was resuspended 11 μl of water.

Eco RI adapters were ligated onto the 5' ends of the cDNA described above to enable cloning into an expression vector. 11 μl of cDNA and 4 μl of 65 pmole/μl of Eco RI hemiphosphorylated adaptor (Pharmacia Biotech Corp) were mixed with 5 μl 5× ligase buffer (Life Technologies), 2 μl of 10 mM ATP and 3 μl of 1 U/μl T4 DNA ligase (Life Technologies), 1 μl 10× ligation buffer (Promega Corp), 9 μl water. The extra dilution with 1× buffer was to prevent the pellet paint from precipitating. The reaction was incubated 9 hours in a water bath temperature ramp from 10° C. to 22° C. over 9 hours, followed by 45 minutes at 25° C. The reaction was terminated by incubation at 68° C. for 15 minutes.

To facilitate the directional cloning of the cDNA into an expression vector, the cDNA was digested with XhoI, resulting in a cDNA having a 5' Eco RI cohesive end and a 3' XhoI cohesive end. The XhoI restriction site at the 3' end of the cDNA had been previously introduced using the ZC18698 primer. Restriction enzyme digestion was carried out in a reaction mixture containing 35 μl of the ligation mix described above, 6 μl of 10×H buffer (Boehringer Mannheim Corp.), 1 μl of 2 mg/ml BSA (Biolabs Corp.), 17 μl water and 1.0 μl of 40 U/μl XhoI (Boehringer Mannheim). Digestion was carried out at 37° C. for 1 hour. The reaction was terminated by incubation at 68° C. for 15 minutes followed by ethanol precipitation, washing drying as described above and resuspension in 30 μl water.

The resuspended cDNA was heated to 65° C. for 5 minutes and cooled on ice, 4 μl of 5× gel loading dye (Research Genetics Corp.) was added, the cDNA was loaded onto a 0.8% low melt agarose 1×TAE gel (SEA PLAQUE GTG™ low melt agarose; FMC Corp.) and electrophoresed. The contaminating adapters and cDNA below 0.6 Kb in length were excised from the gel. The electrodes were reversed, molten agarose was added to fill in the wells, the buffer was changed and the cDNA was electrophoresed until concentrated near the lane origin. The area of the gel containing the concentrated cDNA was excised and placed in a microfuge tube, and the agarose was melted by heating to 65° C. for 15 minutes. Following equilibration of the sample to 45° C., 2 µl of 1 U/µl Beta-agarase I (Biolabs, Inc.) was added, and the mixture was incubated for 90 min. at 45° C. to digest the agarose. After incubation, 1 tenth volume of 3 M Na acetate was added to the sample, and the mixture was incubated on ice for 15 minutes. The sample was centrifuged at 14,000×g for 15 minutes at room temperature to remove undigested agarose, the cDNA was ethanol precipitated, washed in 70% ethanol, air-dried and resuspended in 40 µl water.

To determine the optimum ratio of cDNA to vector several ligations were assembled and electroporated. Briefly, 2 µl of 5×T4 ligase buffer (Life Technologies), 1 µl of 10 mM ATP, 1 µl pZP7NX digested with EcoR1-Xho1, 1 ll T4 DNA ligase diluted to 0.25 u/µl (Life Technologies) water to 10 µl and 0.5, 1, 2 or 3 µl of cDNA were mixed in 4 separate ligations, incubated at 22° C. for 4 hours, 68° C. for 20 minutes, sodium acetate-ethanol precipitated, washed, dried and resuspended in 10 ll. A single microliter of each ligation was electroporated into 40 µl DH10b ElectroMax™ electrocompetent bacteria (Life Technologies) using a 0.1 cm cuvette (Biorad) and a Genepulser, pulse controllerä (Biorad) set to 2.5 KV, 251F, 200 ohms. These cells were immediately resuspended in 1 ml. SOC broth (Manniatis, et al. supra.) followed by 50011 of 50% glycerol-SOC as a preservative. These "glycerol stocks" were frozen in several aliquots at −70° C. An aliquot of each was thawed and plated serially on LB-agar plates supplemented with ampicillin at 100 µg/µl. Colony numbers indicated that the optimum ratio of CD3+ cDNA to pZP7NX vector was 1 µl to 45 ng; such a ligation yielded 4.5 million primary clones.

C. PCR Identification of IL-TIF Message in Activated T-Cell Library

PCR was performed using oligos ZC25,838 (SEQ ID NO:7) and ZC25,840 (SEQ ID NO:5) to screen the above library for presence of a 473 bp product corresponding to IL-TIF clones. PCR amplification was performed with Taq Polymerase (BRL Grand Island N.Y.), and conditions as follows: 30 cycles of 94° C. for 15 sec., 62° C. 20 sec., 72° C. 30 sec.; 1 cycle at 72° C. for 7 min.; and a 4° C. soak. 5 µl of each 50 µl reaction volume was run on a 0.9% agarose 0.5×TBE gel to identify resultant products. Table 6 below describes the results. PCR products were scored as (−) for no product, (+) for expected PCR product visible, (++) increased presence of PCR product and (+++) being the strongest signal.

TABLE 6

Identification of IL-TIF message in activated T-Cell Library

| Template | PCR Product |
| --- | --- |
| 1 ng Activated Library | + |
| 10 ng Activated Library | ++ |
| 100 ng Activated Library | +++ |
| 100 ng Vector Control | − |
| No Template Control | − |

These results indicate the presence of a IL-TIF cDNA clone and therefore message in activated CD3+ T-cells.

Example 5

Southern Blot Analysis

Southern blots were performed using EVO Mammalian Group/EcoRI Southern Blots (Quantum Biotechnologies, Inc., Montreal, Canada) to determine the presence of orthologous IL-TIF sequences. A IL-TIF probe was generated by labeling 25 ng of IL-TIF fragment, as described in Example 2, using Prime-It II Random Primer labeling kit (Stratagene, La Jolla, Calif.). Hybridization was performed using Expresshyb (Clontech) with $5 \times 10^5$ cpm/ml probe and conditions of 65° C. overnight. Stringency washes were performed with 0.2×SSC, 0.1% SDS at 45° C. The blot was exposed overnight at −80° C. to X-ray film and analyzed.

Results showed a strong approximately 1 kb band in the human genomic DNA sample with weaker bands present at approximately 7 and 20 kb for murine genomic DNA demonstrating the presence of a putative murine homolog for IL-TIF.

The mouse cDNA sequence was cloned using standard methods and is shown in SEQ ID NO:37, and corresponding polypeptides sequence shown in SEQ ID NO:38.

Example 6

Chromosomal Assignment and Placement of IL-TIF

IL-TIF was mapped to chromosome 12 using the commercially available version of the "Stanford G3 Radiation Hybrid Mapping Panel" (Research Genetics, Inc., Huntsville, AL). The "Stanford G3 RH Panel" contains DNA from each of 83 radiation hybrid clones of the whole human genome, plus two control DNAs (the RM donor and the A3 recipient). A publicly available WWW server allows chromosomal localization of markers and genes.

For the mapping of IL-TIF with the "Stanford G3 RH Panel", 20 µl reactions were set up in a 96-well microtiter plate compatible for PCR (Stratagene, La Jolla, Calif.) and used in a "RoboCycler Gradient 96" thermal cycler (Stratagene). Each of the 85 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC 26,414 (SEQ ID NO:12), 1 antisense primer, ZC 26,415 (SEQ ID NO:13), 2 µl "RediLoad" (Research Genetics, Inc., Huntsville, Ala.), 0.4 µl 50× Advantage KlenTaq Polymerase Mix (Clontech Laboratories, Inc.), 25 ng of DNA from an individual hybrid clone or control and distilled water for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 66° C. and 1 minute AND 15 seconds extension at 72° C., followed by a final 1 cycle extension of 7 minutes at 72° C. The reactions were separated by electrophoresis on a 2% agarose gel (EM Science, Gibbstown, N.J.) and visualized by staining with ethidium bromide.

The results showed linkage of IL-TIF to the chromosome 12 marker SHGC-17533 with a LOD score of >12 and at a distance of 0 cR_10000 from the marker. The use of surrounding genes and markers positions IL-TIF in the 12q14-q24.3 chromosomal region.

Example 7

Construct for Generating CEE-Tagged IL-TIF

Oligonucleotides were designed to generate a PCR fragment containing the Kozak sequence and the coding region for IL-TIF, without its stop codon. These oligonucleotides were designed with a KpnI site at the 5' end and a BamHI site at the 3' end to facilitate cloning into pHZ200-CEE, our standard vector for mammalian expression of C-terminal Glu-Glu tagged (SEQ ID NO:14) proteins. The pHZ200 vector contains an MT-1 promoter.

PCR reactions were carried out using Turbo Pfu polymerase (Stratagene) to amplify a IL-TIF cDNA fragment. About 20 ng human IL-TIF polynucleotide template (SEQ ID NO:1), and oligonucleotides ZC28590 (SEQ ID NO:16) and ZC28580 (SEQ ID NO:17) were used in the PCR reaction. PCR reaction conditions were as follows: 95° C. for 5 minutes; 30 cycles of 95° C. for 60 seconds, 55° C. for 60 seconds, and 72° C. for 60 seconds; and 72° C. for 10 minutes; followed by a 4° C. hold. PCR products were separated by agarose gel electrophoresis and purified using a QiaQuick™ (Qiagen) gel extraction kit. The isolated, approximately 600 bp, DNA fragment was digested with KpnI and BamHI (Boerhinger-Mannheim), gel purified as above and ligated into pHZ200-CEE that was previously digested with KpnI and BamHI.

About one microliter of the ligation reaction was electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies were picked and screened by PCR using oligonucleotides ZC28,590 (SEQ ID NO:16) and ZC28,580 (SEQ ID NO:17), with PCR conditions as described above. Clones containing inserts were then sequenced to confirm error-free IL-TIF inserts. Maxipreps of the correct pHZ200-IL-TIF-CEE construct, as verified by sequence analysis, were performed.

Example 8

Transfection And Expression of IL-TIF-CEE Polypeptides

BHK 570 cells (ATCC No. CRL-10314), were plated at about $1 \times 10^6$ cells/100 mm culture dish in 6.4 ml of serum free (SF) DMEM media (DMEM, Gibco/BRL High Glucose) (Gibco BRL, Gaithersburg, Md.). The cells were transfected with an expression plasmid containing IL-TIF-CEE described above (Example 7), using Lipofectin™ (Gibco BRL), in serum free (SF) DMEM according to manufacturer's instructions.

The cells were incubated at 37° C. for approximately five hours, then 10 ml of DMEM/10% fetal bovine serum (FBS) (Hyclone, Logan, Utah) was added. The plates were incubated at 37° C., 5% $CO_2$, overnight and the DMEM/10% FBS media was replaced with selection media (5% FBS/DMEM with 1 µM methotrexate (MTX)) the next day.

Approximately 7-10 days post-transfection, pools of cells or colonies were mechanically picked to 12-well plates in one ml of 5% FCS/DMEM with 5 µM MTX, then grown to confluence. Cells were then incubated in 5% FCS/DMEM with 10 µM MTX for at least 14 days. Conditioned media samples from positive expressing clonal colonies and pools were then tested for expression levels via SDS-PAGE and Western analysis. A high-expressing clonesor pools were picked and expanded for ample generation of conditioned media for purification of the IL-TIF-CEE expressed by the cells (Example 9).

Example 9

Purification of IL-TIF-CEE from BHK 570 Cells

Unless otherwise noted, all operations were carried out at 4° C. The following procedure was used for purifying IL-TIF polypeptide containing C-terminal GluGlu (EE) tags (SEQ ID NO:14). A Protease inhibitor solution was added to the concentrated conditioned media containing IL-TIF-CEE (Example 8) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim).

About 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated conditioned media was 0.2 micron sterile filtered, pH adjusted to 7.4, then loaded on the column overnight with about 1 ml/minute flow rate. The column was washed with 10 column volumes (CVs) of phosphate buffered saline (PBS, pH 7.4), then plug eluted with 200 ml of PBS (pH 6.0) containing 0.1 mg/ml EE peptide (Anaspec, San Jose, Calif.) at 5 ml/minute. The EE peptide used has the sequence EYMPME (SEQ ID NO:14). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate IL-TIF-CEE polypeptide from free EE peptide and any contaminating co-purifying proteins, the pooled concentrated fractions were subjected to size exclusion chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified IL-TIF-CEE polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the IL-TIF-CEE polypeptide was two major bands and two mionor bands. The protein concentration of the purified material was performed by BCA analysis (Pierce, Rockford, Ill.) and the protein was aliquoted, and stored at −80° C. according to standard procedures. In a Western blot analysis, all bands were immunoreactive with a rabbit anti-IL-TIF-peptide antibody (Example 16). The 4 bands likely represent different glycosylated forms of the IL-TIF polypeptide.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min at room temperature with 5 volumes of 20 mM ethanolamine in 200 mM TEA. The gel was then washed with 5 volumes of PBS containing 0.02% sodium azide and stored in this solution at 4° C.

Example 10

Generation of Non-Tagged IL-TIF Recombinant Adenovirus

The protein coding region of human IL-TIF (SEQ ID NO:1; SEQ ID NO:2) was amplified by PCR using primers that added FseI and AscI restriction sties at the 5' and 3' termini respectively. PCR primers ZC26665 (SEQ ID NO:20) and ZC26666 (SEQ ID NO:21) were used with pINCY template plasmid containing the full-length IL-TIF cDNA in a PCR reaction as follows: one cycle at 95° C. for 5 minutes; followed by 18 cycles at 95° C. for 0.5 min., 58° C. for 0.5 min, and 72° C. for 0.5 min.; followed by 72° C. for 7 min.; followed by a 4° C. soak. The PCR reaction product was loaded onto a 1.2% (low melt) SeaPlaque GTG (FMC, Rockland, Me.) gel in TAE buffer. The IL-TIF PCR product was excised from the gel and the gel slice melted at 70 μ° C., extracted twice with an equal volume of Tris buffered phenol, and EtOH precipitated.

The 540 bp IL-TIF PCR product was digested with FseI and AscI enzymes. The cDNA was isolated on a 1% low melt SeaPlaque GTG™ (FMC, Rockland, Me.) gel and was then excised from the gel and the gel slice melted at 70° C., extracted twice with an equal volume of Tris buffered phenol, and EtOH precipitated. The DNA was resuspended in 10 μl $H_2O$.

The IL-TIF cDNA was cloned into the FseI-AscI sites of a modified pAdTrack CMV (He, T-C. et al., *PNAS* 95:2509-2514, 1998). This construct contains the GFP marker gene. The CMV promoter driving GFP expression was replaced with the SV40 promoter and the SV40 polyadenylation signal was replaced with the human growth hormone polyadenylation signal. In addition, the native polylinker was replaced with FseI, EcoRV, and AscI sites. This modified form of pAdTrack CMV was named pZyTrack. Ligation was performed using the Fast-Link™ DNA ligation and screening kit (Epicentre Technologies, Madison, Wis.). Clones containing the IL-TIF insert were identified by standard mini prep analysis. The cloned IL-TIF cDNA was sequenced to verify no errors were introduced during PCR. In order to linearize the plasmid, approximately 5 μg of the pZyTrack IL-TIF plasmid was digested with PmeI. Approximately 1 μg of the linearized plasmid was cotransformed with 200 ng of supercoiled pAdEasy (He et al., supra.) into BJ5183 cells. The co-transformation was done using a Bio-Rad Gene Pulser at 2.5 kV, 200 ohms and 25 mFa. The entire co-transformation was plated on 4 LB plates containing 25 μg/ml kanamycin. The smallest colonies were picked and expanded in LB/kanamycin and recombinant adenovirus DNA identified by standard DNA miniprep procedures. Digestion of the recombinant adenovirus DNA with FseI-AscI confirmed the presence of IL-TIF. The recombinant adenovirus miniprep DNA was transformed into DH10B competent cells and DNA prepared using a Qiagen maxi prep kit as per kit instructions.

Transfection of 293a Cells with Recombinant DNA

Approximately 5 μg of recombinant adenoviral DNA was digested with PacI enzyme (New England Biolabs) for 3 hours at 37° C. in a reaction volume of 100 μl containing 20-30 U of PacI. The digested DNA was extracted twice with an equal volume of phenol/chloroform and precipitated with ethanol. The DNA pellet was resuspended in 5 μl distilled water. A T25 flask of QBI-293A cells (Quantum Biotechnologies, Inc. Montreal, Qc. Canada), inoculated the day before and grown to 60-70% confluence, were transfected with the PacI digested DNA. The PacI-digested DNA was diluted up to a total volume of 50 μl with sterile HBS (150 mM NaCl, 20 mM HEPES). In a separate tube, 25 μl DOTAP (Boehringer Mannheim, 1 mg/ml) was diluted to a total volume of 100 μl with HBS. The DNA was added to the DOTAP, mixed gently by pipeting up and down, and left at room temperature for 15 minutes. The media was removed from the 293A cells and washed with 5 ml serum-free MEMalpha (Gibco BRL) containing 1 mM Sodium Pyruvate (GibcoBRL), 0.1 mM MEM non-essential amino acids (GibcoBRL) and 25 mM HEPES buffer (GibcoBRL). 5 ml of serum-free MEM was added to the 293A cells and held at 37° C. The DNA/lipid mixture was added drop-wise to the T25 flask of 293A cells, mixed gently and incubated at 37° C. for 4 hours. After 4 hours the media containing the DNA/lipid mixture was aspirated off and replaced with 5 ml complete MEM containing 5% fetal bovine serum. The transfected cells were monitored for Green Fluorescent Protein (GFP) expression and formation of foci, i.e., viral plaques.

Seven days after transfection of 293A cells with the recombinant adenoviral DNA, the cells expressed the GFP protein and started to form foci. These foci are viral "plaques" and the crude viral lysate was collected by using a cell scraper to collect all of the 293A cells. The lysate was transferred to a 50 ml conical tube. To release most of the virus particles from the cells, three freeze/thaw cycles were done in a dry ice/ethanol bath and a 37° C. waterbath.

Amplification of Recombinant Adenovirus (rAdV)

The crude lysate was amplified (Primary (1°) amplification) to obtain a working "stock" of zsig45 rAdV lysate. Ten 10 cm plates of nearly confluent (80-90%) 293A cells were set up 20 hours previously, 200 ml of crude rAdV lysate added to each 10 cm plate and monitored for 48 to 72 hours looking for CPE under the white light microscope and expression of GFP under the fluorescent microscope. When all of the 293A cells showed CPE (Cytopathic Effect) this 1° stock lysate was collected and freeze/thaw cycles performed as described under Crude rAdV Lysate.

Secondary (2°) Amplification of zsig46 rAdV was obtained as follows: Twenty 15 cm tissue culture dishes of 293A cells were prepared so that the cells were 80-90% confluent. All but 20 mls of 5% MEM media was removed and each dish was inoculated with 300-500 ml 1° amplified rAdv lysate. After 48 hours the 293A cells were lysed from virus production and this lysate was collected into 250 ml polypropylene centrifuge bottles and the rAdV purified.

rAdV/cDNA Purification

NP-40 detergent was added to a final concentration of 0.5% to the bottles of crude lysate in order to lyse all cells. Bottles were placed on a rotating platform for 10 min. agitating as fast as possible without the bottles falling over. The debris was pelleted by centrifugation at 20,000×G for 15 minutes. The supernatant was transferred to 250 ml polycarbonate centrifuge bottles and 0.5 volumes of 20% PEG8000/2.5M NaCl solution added. The bottles were shaken overnight on ice. The bottles were centrifuged at 20,000×G for 15 minutes and supernatant discarded into a bleach solution. The white precipitate in two vertical lines along the wall of the bottle on either side of the spin mark is the precipitated virus/PEG. Using a sterile cell scraper, the precipitate from 2 bottles was resuspended in 2.5 ml PBS. The virus solution was placed in 2 ml microcentrifuge tubes and centrifuged at 14,000×G in the microfuge for 10 minutes to remove any additional cell debris. The supernatant from the 2 ml microcentrifuge tubes was transferred into a 15 ml polypropylene snapcap tube and adjusted to a density of 1.34 g/ml with cesium chloride (CsCl). The volume of the virus solution was estimated and 0.55 g/ml of CsCl added. The CsCl was dissolved and 1 ml of this solution weighed 1.34 g. The solution was transferred polycarbonate thick-walled centrifuge tubes 3.2 ml (Beckman) and spin at 80,000 rpm (348,000×G) for 3-4 hours at 25° C. in a Beckman Optima TLX microultracentrifuge with the TLA-100.4 rotor. The virus formed a white band. Using wide-bore pipette tips, the virus band was collected.

The virus from the gradient has a large amount of CsCl which must be removed before it can be used on cells. Pharmacia PD-10 columns prepacked with Sephadex G-25M (Pharmacia) were used to desalt the virus preparation. The column was equilibrated with 20 ml of PBS. The virus was loaded and allow it to run into the column. 5 ml of PBS was added to the column and fractions of 8-10 drops collected. The optical densities of 1:50 dilutions of each fraction was determined at 260 nm on a spectrophotometer. A clear absorbance peak was present between fractions 7-12. These fractions were pooled and the optical density (OD) of a 1:25 dilution determined A formula is used to convert OD into virus concentration: (OD at 260 nm)(25)($1.1\times10^{12}$)=virions/ml. The OD of a 1:25 dilution of the IL-TIF rAdV was 0.134, giving a virus concentration of $3.7\times10^{12}$ virions/ml.

To store the virus, glycerol was added to the purified virus to a final concentration of 15%, mixed gently but effectively, and stored in aliquots at −80° C.

Tissue Culture Infectious Dose at 50% CPE (TCID 50) Viral Titration Assay

A protocol developed by Quantum Biotechnologies, Inc. (Montreal, Qc. Canada) was followed to measure recombinant virus infectivity. Briefly, two 96-well tissue culture plates were seeded with $1\times10^4$ 293A cells per well in MEM containing 2% fetal bovine serum for each recombinant virus to be assayed. After 24 hours 10-fold dilutions of each virus from $1\times10^{-2}$ to $1\times10^{14}$ were made in MEM containing 2% fetal bovine serum. 100 µl of each dilution was placed in each of 20 wells. After 5 days at 37° C., wells were read either positive or negative for Cytopathic Effect (CPE) and a value for "Plaque Forming Units/ml" (PFU) is calculated.

$TCID_{50}$ formulation used was as per Quantum Biotechnologies, Inc., above. The titer (T) is determined from a plate where virus used is diluted from $10^{-2}$ to $10^{-14}$, and read 8 days after the infection. At each dilution a ratio (R) of positive wells for CPE per the total number of wells is determined.

To Calculate titer of the undiluted virus sample: the factor, "F"=1+d(S−0.5); where "S" is the sum of the ratios (R); and "d" is Log 10 of the dilution series, for example, "d" is equal to 1 for a ten-fold dilution series. The titer of the undiluted sample is $T=10^{(1+F)}=TCID_{50}$/ml. To convert $TCID_{50}$/ml to pfu/ml, 0.7 is subtracted from the exponent in the calculation for titer (T). The IL-TIF adenovirus had a titer of $2.8\times10^{11}$ pfu/ml.

Example 11

In vivo Affects of IL-TIF Polypeptide

Mice (female, C57B1, 8 weeks old; Charles River Labs, Kingston, N.Y.) were divided into three groups. On day 0, parental or IL-TIF adenovirus (Example 10) was administered to the first (n=8) and second (n=8) groups, respectively, via the tail vein, with each mouse receiving a dose of ~$1\times10^{11}$ particles in ~0.1 ml volume. The third group (n=8) received no treatment. On days 12, mice were weighed and blood was drawn from the mice. Samples were analyzed for complete blood count (CBC) and serum chemistry. Statistically significant elevations in neutrophil and platelet counts were detected in the blood samples from the IL-TIF adenovirus administered group relative to the parental adenovirus treated group. Also, at day 12 lymphocyte counts were significantly reduced from the IL-TIF adenovirus administered group relative to the parental adenovirus treated group, and they rebounded to normal levels by day 21. In addition, the IL-TIF adenovirus treated mice decreased in body weight, while parental adenovirus treated mice gained weight. The elevated platelet and neutrophil count, and the loss of body weight are still significant as compared to the control group. The liver chemistry test indicated the increased level of globulin and decreased level of albumin concentration, which is consistant with the observation of inflammatory response induced by TNF-a.

The results suggested that IL-TIF affects hematopoiesis, i.e., blood cell formation in vivo. As such, IL-TIF could have biological activities affecting different blood precursors, progenitors or stem cells, and a resulting increase or decrease of certain differentiated blood cells in a specific lineage. For instance, IL-TIF appeared to reduce lymphocytes, which is likely due to inhibition of the committed progenitor cells that give rise to lymphoid cells. This finding agrees with the inhibitory effects of IL-TIF on the proliferation and/or growth of myeloid stem cells (Example 23), supporting the notion that IL-TIF could play a role in anemia, infection, inflammation, and/or immune diseases by influencing blood cells involved in these process. Antagonists against IL-TIF, such as anti-IL-TIF antibodies, biding partners, or a soluble receptor antagonist could be used as therapeutic reagents in these diseases. It is also possible that IL-TIF directly affects the release and survival of platelets in peripheral blood or other vascularized tissues such as liver. That is, besides working through a hematopoisis loop (differentiation, proliferation of stem cells), IL-TIF might directly affect the release, stablization or depletion of platelets and neutrophils in peripheral blood or some target tissue and organs. IL-TIF also affected the number of granulocytes in the peripheral blood. Extramedullary sites of hematopoiesis (e.g. liver) are also targets for IL-TIF action.

Moreover, these experiments using IL-TIF adenovirus in mice suggested that IL-TIF over-expression increases the level of neutrophils and platelets in vivo. Although increasing neutrophils and platelets is desirable in certain therapeutic applications discussed herein, chronic elevation or increased reactivity of these cells could play a role in cardiovascular disease. Antagonists against IL-TIF, such as antibodies or its soluble receptor, could be used as therapeutic reagents in these diseases. Although this may appear contradictory to the finding seen in K562 cells (Example 12), it is not uncommon to observe diverse activities of a particular protein in vitro versus in vivo. It is conceivable that there are other factors (such as cytokines and modifier genes) involved in the responses to IL-TIF in the whole animal system. Nevertheless, these data strongly support the involvement of IL-TIF in hematopoiesis. Thus, IL-TIF and its receptors are suitable reagents/targets for the diagnosis and treatment in variety of disorders, such as inflammation, immune disorders, infection, anemia, hematopoietic and other cancers, and the like.

Example 12

The IL-TIF Polypeptide Inhibits the Growth of K-562 Cells in A Cytotoxicity Assay The K-562 cell line (CRL-243, ATCC) has attained widespread use as a highly sensitive in vitro target for cytotoxicity assays. K-562 blasts are multipotential, hematopoietic malignant cells that spontaneously differentiate into recognizable progenitors of the erythrocytic, granulocytic and monocytic series (Lozzio, B B et al., Proc. Soc. Exp. Biol. Med. 166: 546-550, 1981).

K562 cells were plated at 5,000 cells/well in 96-well tissue culture clusters (Costar) in DMEM phenol-free growth medium (Life Technologies) supplemented with pyruvate and 10% serum (HyClone). Next day, human recombinant IL-TIF (Example 19), BSA control or retinoic acid (known to be cytotoxic to K562 cells) were added. Seventy-two hours later, the vital stain MTT (Sigma, St Louis, Mo.), a widely used indicator of mitochondrial activity and cell growth, was added to the cells at a final concentration of 0.5 mg/ml. MTT is converted to a purple formazan derivative by mitochondrial dehydrogenases. Four hours later, converted MTT was solubilized by adding an equal volume of acidic isopropanol (0.04N HCl in absolute isopropanol) to the wells. Absorbance was measured at 570 nm, with background subtraction at 650 nm. In this experimental setting, absorbance reflects cell viability. Results shown in Table 7 are expressed as % cytotoxicity.

TABLE 7

| Agent | Concentration | % Cytotoxicity |
| --- | --- | --- |
| BSA Control | 1 ug/ml | 1.3 |
| Retinoic acid | 100 uM | 62 |
| IL-TIF | 100 ng/ml | 16.2 |
| IL-TIF | 300 ng/ml | 32 |

The results indicated that IL-TIF may affect myeloid stem cells. Myeloid stem cells are daughter cells of the universal blood stem cells. They are progenitors of erythrocytes, monocytes (or migrated macrophages), neutrophil, basophil, and eosinophils. Since K-562 blasts differentiate into progenitors of the erythrocytic, granulocytic and monocytic series, they are considered a model for myeloid stem cells. Thus, the results demonstrated that IL-TIF has an inhibitory activity on the proliferation and/or growth of a promyelocytic tumor cell line. Thus IL-TIF could play a role in anemia, infection, inflammation, and/or immune diseases. In addition, an antagonist against IL-TIF, such as antibodies or a soluble receptor antagonist, could be used to block IL-TIF's activity on myeloid stem cells, or as therapeutic reagents in diseases such as anemia, infection, inflammation, and/or immune diseases. Moreover, as IL-TIF exhibits cytotoxicity on tumor cells, it can be used directly or in combination with other cytokines as an anti-tumor agent.

Example 13

Human Zcytor16 Tissue Distribution in Tissue Panels Using Northern Blot and PCR A. Human zcytor16 Tissue Distribution using Northern Blot and Dot Blot Commonly owned, human zcytor16 (SEQ ID NO:32, and SEQ ID NO:33) (WIPO Publication No. WO 01/40467) is a naturally-expressed soluble receptor antagonist of IL-TIF. Northern blot analysis was performed using Human Multiple Tissue Northern Blots I, II, III (Clontech) and an in house generated U-937 northern blot. U-937 is a human promonocytic blast cell line. The cDNA probe was generated using oligos ZC25,963 (SEQ ID NO:24) and ZC28,354 (SEQ ID NO:25). The PCR conditions were as follows: 94° for 1 minute; 30 cycles of 94°, 15 seconds; 60°, 30 seconds; 72°, 30 seconds and a final extension for 5 minutes at 72°. The 364 bp product was gel purified by gel electrophoresis on a 1% TBE gel and the band was excised with a razor blade. The cDNA was extracted from the agarose using the QIAquick Gel Extraction Kit (Qiagen). 94 ng of this fragment was radioactively labeled with $^{32}$P-dCTP using Rediprime II (Amersham), a random prime labeling system, according to the manufacturer's specifications. Unincorporated radioactivity was removed using a Nuc-Trap column (Stratagene) according to manufacturer's instructions. Blots were prehybridized at 65° for 3 hours in ExpressHyb (Clontech) solution. Blots were hybridized overnight at 65° in Expresshyb solution containing $1.0 \times 10^6$ cpm/ml of labeled probe, 0.1 mg/ml of salmon sperm DNA and 0.5 µg/ml of human cot-1 DNA. Blots were washed in 2×SSC, 0.1% SDS at room temperature with several solution changes then washed in 0.1×SSC. 0.1% SDS at 55° for 30 minutes twice. Transcripts of approximately 1.6 kb and 3.0 kb size were detected in spleen and placenta, but not other tissues examined. The same sized transcripts plus an additional approximate 1.2 kb transcript was detected in U-937 cell line.

B. Tissue Distribution in Tissue cDNA Panels Using PCR

A panel of cDNAs from human tissues was screened for zcytor16 expression using PCR. The panel was made in-house and contained 94 marathon cDNA and cDNA samples from various normal and cancerous human tissues and cell lines are shown in Table 8, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21195 (SEQ ID NO:26) and ZC21196 (SEQ ID NO:27) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:28) and 3' alpha tubulin specific oligo primer ZC17,574 (SEQ ID NO:29) or 3' G3PDH specific oligo primer ZC17,600 (SEQ ID NO:30); and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2-100 pg/µl of cDNA. The PCR reactions were set up using oligos ZC25,963 (SEQ ID NO:24) and ZC27,659 (SEQ ID NO:25), Advantage 2 DNA Polymerase Mix (Clontech) and Rediload dye (Research Genetics, Inc., Huntsville, Ala.). The amplification was carried out as follow: 1 cycle at 94° C. for 2 minutes, 30 cycles of 94° C. for 20 seconds, 58° C. for 30 seconds and 72° C. for 1 minute, followed by 1 cycle at 72° C. for 5 minutes. About 10 µl of the PCR reaction product was subjected to standard Agarose gel electrophoresis using a 2% agarose gel. The correct predicted DNA fragment size was not observed in any tissue or cell line. Subsequent experiments showing expression of zcytor16 indicated that the negative results from this panel were likely due to the primers used.

TABLE 8

| Tissue/Cell line | #samples |
| --- | --- |
| Adrenal gland | 1 |
| Bladder | 1 |
| Bone Marrow | 1 |
| Brain | 1 |
| Cervix | 1 |
| Colon | 1 |
| Fetal brain | 1 |
| Fetal heart | 1 |
| Fetal kidney | 1 |
| Fetal liver | 1 |
| Fetal lung | 1 |
| Fetal muscle | 1 |
| Fetal skin | 1 |
| Heart | 2 |
| K562 (ATCC # CCL-243) | 1 |
| Kidney | 1 |
| Liver | 1 |
| Lung | 1 |
| Lymph node | 1 |
| Melanoma | 1 |
| Pancreas | 1 |
| Pituitary | 1 |
| Placenta | 1 |
| Prostate | 1 |
| Rectum | 1 |
| Salivary Gland | 1 |
| Skeletal muscle | 1 |
| Small intestine | 1 |
| Spinal cord | 1 |
| Spleen | 1 |
| Stomach | 1 |
| Testis | 2 |
| Thymus | 1 |
| Thyroid | 1 |
| Trachea | 1 |
| Uterus | 1 |
| Esophagus tumor | 1 |
| Gastric tumor | 1 |
| Kidney tumor | 1 |
| Liver tumor | 1 |
| Lung tumor | 1 |
| Ovarian tumor | 1 |
| Rectal tumor | 1 |
| Uterus tumor | 1 |
| Bone marrow | 3 |
| Fetal brain | 3 |
| Islet | 2 |
| Prostate | 3 |
| RPMI #1788 (ATCC # CCL-156) | 2 |
| Testis | 4 |
| Thyroid | 2 |
| WI38 (ATCC # CCL-75) | 2 |
| ARIP (ATCC # CRL-1674—rat) | 1 |
| HaCat—human keratinocytes | 1 |
| HPV (ATCC # CRL-2221) | 1 |
| Adrenal gland | 1 |
| Prostate SM | 2 |
| CD3+ selected PBMC's Ionomycin + PMA stimulated | 1 |
| HPVS (ATCC # CRL-2221)—selected | 1 |
| Heart | 1 |
| Pituitary | 1 |
| Placenta | 2 |
| Salivary gland | 1 |
| HL60 (ATCC # CCL-240) | 3 |
| Platelet | 1 |
| HBL-100 | 1 |
| Renal mesangial | 1 |
| T-cell | 1 |
| Neutrophil | 1 |
| MPC | 1 |
| Hut-102 (ATCC # TIB-162) | 1 |
| Endothelial | 1 |
| HepG2 (ATCC # HB-8065) | 1 |
| Fibroblast | 1 |
| E. Histo | 1 |

An additional panel of cDNAs from human tissues was screened for zcytor16 expression using PCR. This panel was made in-house and contained 77 marathon cDNA and cDNA samples from various normal and cancerous human tissues and cell lines are shown in Table 9, below. Aside from the PCR reaction, the assay was carried out as per above. The PCR reactions were set up using oligos ZC25,963 (SEQ ID NO:24) and ZC25,964 (SEQ ID NO:31), Advantage 2 DNA Polymerase Mix (Clontech) and Rediload dye (Research Genetics, Inc., Huntsville, Ala.). The amplification was carried out as follow: 1 cycle at 94° C. for 1 minute, 38 cycles of 94° C. for 10 seconds, 60° C. for 30 seconds and 72° C. for 30 seconds, followed by 1 cycle at 72° C. for 5 minutes. The correct predicted DNA fragment size was observed in bone marrow, fetal heart, fetal kidney, fetal muscle, fetal skin, heart, mammary gland, placenta, salivary gland, skeletal muscle, small intestine, spinal cord, spleen, kidney, fetal brain, esophageal tumor, uterine tumor, stomach tumor, ovarian tumor, rectal tumor, lung tumor and RPMI-1788 (a B-lymphocyte cell line). Zcytor16 expression was not observed in the other tissues and cell lines tested in this panel. The expression pattern of zcytor16 shows expression in certain tissue-specific tumors especially, e.g., ovarian cancer, stomach cancer, uterine cancer, rectal cancer, lung cancer and esophageal cancer, where zcytor16 is not expressed in normal tissue, but is expressed in the tumor tissue. One of skill in the art would recognize that the natural ligand, IL-TIF, and receptor binding fragments of IL-TIF can be used as a diagnostic to detect cancer, or cancer tissue in a biopsy, tissue, or histologic sample, particularly e.g., ovarian cancer, stomach cancer, uterine cancer, rectal cancer, lung cancer and esophageal cancer tissue. Such diagnostic uses for the molecules are known in the art and described herein.

In addition, because the expression pattern of zcytor16, one of IL-TIF's receptors, shows expression in certain specific tissues as well as tissue-specific tumors, binding partners including the natural ligand, IL-TIF, can also be used as a diagnostic to detect specific tissues (normal or abnormal), cancer, or cancer tissue in a biopsy, tissue, or histologic sample, where IL-TIF receptors are expressed, and particularly e.g., ovarian cancer, stomach cancer, uterine cancer, rectal cancer, lung cancer and esophageal cancer tissue. IL-TIF can also be used to target other tissues wherein its receptors, e.g., zcytor16 and zcytor11 (Commonly owned U.S. Pat. No. 5,965,704) are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. Activated CD4+ cells and activated CD19+ cells showed zcytor16 expression, whereas the other cells tested, including resting CD4+ cells and resting CD19+ cells, did not.

TABLE 9

| Tissue | #samples |
| --- | --- |
| adrenal gland | 1 |
| bone marrow | 3 |
| cervix | 1 |

TABLE 9-continued

| Tissue | #samples |
| --- | --- |
| fetal brain | 3 |
| fetal kidney | 1 |
| fetal lung | 1 |
| heart | 2 |
| kidney | 2 |
| lung | 1 |
| mammary gland | 1 |
| ovary | 1 |
| pituitary | 2 |
| prostate | 3 |
| salivary gland | 2 |
| small intestine | 1 |
| spleen | 1 |
| stomach | 1 |
| testis | 5 |
| thymus | 1 |
| thyroid | 2 |
| trachea | 1 |
| esophageal tumor | 1 |
| liver tumor | 1 |
| rectal tumor | 1 |
| uterine tumor | 2 |
| HaCAT library | 1 |
| HPVS library | 1 |
| K562 | 1 |
| bladder | 1 |
| brain | 2 |
| colon | 1 |
| fetal heart | 2 |
| fetal liver | 2 |
| fetal skin | 1 |
| fetal muscle | 1 |
| liver | 1 |
| lymph node | 1 |
| melanoma | 1 |
| pancreas | 1 |
| placenta | 3 |
| rectum | 1 |
| skeletal muscle | 1 |
| spinal cord | 2 |
| uterus | 1 |
| adipocyte library | 1 |
| islet | 1 |
| prostate SMC | 1 |
| RPMI 1788 | 1 |
| WI38 | 1 |
| lung tumor | 1 |
| ovarian tumor | 1 |
| stomach tumor | 1 |
| CD3+ library | 1 |
| HPV library | 1 |
| MG63 library | 1 |

C. Tissue Distribution in Human Tissue and Cell Line RNA Panels Using RT-PCR

A panel of RNAs from human cell lines was screened for zcytor16 expression using RT-PCR. The panels were made in house and contained 84 RNAs from various normal and cancerous human tissues and cell lines as shown in Tables 10-13 below. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC25,963 (SEQ ID NO:24) and ZC25,964 (SEQ ID NO:31), Rediload dye and SUPERSCRIPT One Step RT-PCR System (Life Technologies, Gaithersburg, Md.). The amplification was carried out as follows: one cycle at 55° for 30 minutes followed by 40 cycles of 94°, 15 seconds; 59°, 30 seconds; 72°, 30 seconds; then ended with a final extension at 72° for 5 minutes. 8 to 10 μls of the PCR reaction product was subjected to standard Agarose gel electrophoresis using a 4% agarose gel. The correct predicted cDNA fragment size of 184 bps was observed in cell lines U-937, HL-60, ARPE-19, HaCat#1, HaCat#2, HaCat#3, and HaCat#4; bladder, cancerous breast, normal breast adjacent to a cancer, bronchus, colon, ulcerative colitis colon, duodenum, endometrium, esophagus, gastro-esophageal, heart left ventricle, heart ventricle, ileum, kidney, lung, lymph node, lymphoma, mammary adenoma, mammary gland, cancerous ovary, pancreas, parotid and skin, spleen lymphoma and small bowel. Zcytor16 expression was not observed in the other tissues and cell lines tested in this panel.

Zcytor16 is detectably expressed by PCR in normal tissues: such as, the digestive system, e.g., esophagus, gastro-esophageal, pancreas, duodenum, ileum, colon, small bowel; the female reproductive system, e.g., mammary gland, endometrium, breast (adjacent to cancerous tissues); and others systems, e.g., lymph nodes, skin, parotid, bladder, bronchus, heart ventricles, and kidney. Moreover, Zcytor16 is detectably expressed by PCR in several human tumors: such as tumors associated with female reproductive tissues e.g., mammary adenoma, ovary cancer, uterine cancer, other breast cancers; and other tissues such as lymphoma, stomach tumor, and lung tumor. The expression of zcytor16 is found in normal tissues of female reproductive organs, and in some tumors associated with these organs. As such, a ligand for zcytor16, such as IL-TIF, or a receptor-binding fragment thereof, can serve as a marker for these tumors wherein the zcytor16 may be over-expressed. Several cancers positive for zcytor16 are associated with ectodermal/epithelial origin (mammary adenoma, and other breast cancers). Hence, ligand for zcytor16, such as IL-TIF, or a receptor-binding fragment thereof, can serve as a marker for epithelial tissue, such as epithelial tissues in the digestive system and female reproductive organs (e.g., endometrial tissue, columnar epithelium), as well as cancers involving epithelial tissues. Moreover, in a preferred embodiment, IL-TIF, or a receptor-binding fragment thereof, can serve as a marker for certain tissue-specific tumors especially, e.g., ovarian cancer, stomach cancer, uterine cancer, rectal cancer, lung cancer and esophageal cancer, where it's receptor zcytor16 is not expressed in normal tissue, but is expressed in the tumor tissue. Use of polynucleotides, polypeptides, and antibodies of the present invention for diagnostic purposes are known in the art, and disclosed herein.

TABLE 10

| Tissue | #samples |
| --- | --- |
| adrenal gland | 6 |
| bladder | 3 |
| brain | 2 |
| brain meningioma | 1 |
| breast | 1 |
| cancerous breast | 4 |
| normal breast adjacent to cancer | 5 |
| bronchus | 3 |
| colon | 15 |
| cancerous colon | 1 |
| normal colon adjacent to cancer | 1 |
| ulcerative colitis colon | 1 |
| duodenum | 1 |
| endometrium | 5 |
| cancerous endometrium | 1 |
| gastric cancer | 1 |
| esophagus | 7 |
| gastro-esophageal | 1 |
| heart aorta | 1 |
| heart left ventricle | 4 |
| heart right ventricle | 2 |
| heart ventricle | 1 |
| ileum | 3 |
| kidney | 15 |
| cancerous kidney | 1 |

TABLE 11

| Tissue/Cell Line | #samples |
|---|---|
| 293 | 1 |
| C32 | 1 |
| HaCat#1 | 1 |
| HaCat#2 | 1 |
| HaCat#3 | 1 |
| HaCat#4 | 1 |
| WI-38 | 1 |
| WI-38 + 2 um ionomycin #1 | 1 |
| WI-38 + 2 um ionomycin #2 | 1 |
| WI-38 + 5 um ionomycin#1 | 1 |
| WI-38 + 5 um ionomycin#2 | 1 |
| Caco-2, | 1 |
| Caco-2, differentiated | 1 |
| DLD-1 | 1 |
| HRE | 1 |
| HRCE | 1 |
| MCF7 | 1 |
| PC-3 | 1 |
| TF-1 | 1 |
| 5637 | 1 |
| 143B | 1 |
| ME-180 | 1 |
| prostate epithelia | 1 |
| U-2 OS | 1 |
| T-47D | 1 |
| Mg-63 | 1 |
| Raji | 1 |
| U-373 MG | 1 |
| A-172 | 1 |
| CRL-1964 | 1 |
| CRL-1964 + butryic acid | 1 |
| HUVEC | 1 |
| SK-Hep-1 | 1 |
| SK-Lu-1 | 1 |
| Sk-MEL-2 | 1 |
| K562 | 1 |
| BeWo | 1 |
| FHS74.Int | 1 |
| HL-60 | 1 |
| Malme 3M | 1 |
| FHC | 1 |
| HREC | 1 |
| HBL-100 | 1 |
| Hs-294T | 1 |
| Molt4 | 1 |
| RPMI | 1 |
| U-937 | 1 |
| A-375 | 1 |
| HCT-15 | 1 |
| HT-29 | 1 |
| MRC-5 | 1 |
| RPT-1 | 1 |
| RPT-2 | 1 |
| WM-115 | 1 |
| A-431 | 1 |
| WERI-Rb-1 | 1 |
| HEL-92.1.7 | 1 |
| HuH-7 | 1 |
| MV-4-11 | 1 |
| U-138 | 1 |
| CCRF-CEM | 1 |
| Y-79 | 1 |
| A-549 | 1 |
| EL-4 | 1 |
| HeLa 229 | 1 |
| HUT 78 | 1 |
| NCI-H69 | 1 |
| SaOS2 | 1 |
| USMC | 1 |
| UASMC | 2 |
| AoSMC | 1 |
| UtSMC | 1 |
| HepG2 | 1 |
| HepG2-IL6 | 1 |
| NHEK#1 | 1 |
| NHEK#2 | 1 |
| NHEK#3 | 1 |
| NHEK#4 | 1 |
| ARPE-19 | 1 |
| G-361 | 1 |
| HISM | 1 |
| 3AsubE | 1 |
| INT407 | 1 |

TABLE 12

| Tissue | #samples |
|---|---|
| liver | 10 |
| lymph node | 1 |
| lymphoma | 4 |
| mammary adenoma | 1 |
| mammary gland | 3 |
| melinorioma | 1 |
| osteogenic sarcoma | 2 |
| pancreas | 4 |
| skin | 5 |
| sarcoma | 2 |
| lung | 13 |
| cancerous lung | 2 |
| normal lung adjacent to cancer | 1 |
| muscle | 3 |
| neuroblastoma | 1 |
| omentum | 2 |
| ovary | 6 |
| cancerous ovary | 2 |
| parotid | 7 |
| salivary gland | 4 |

TABLE 13

| Tissue | #samples |
|---|---|
| small bowel | 10 |
| spleen | 3 |
| spleen lymphoma | 1 |
| stomach | 13 |
| stomach cancer | 1 |
| uterus | 11 |
| uterine cancer | 1 |
| thyroid | 9 |

Example 14

Human zcytor11 Tissue Distribution in Tissue Panels Using Northern Blot and PCR

A. Human zcytor11 Tissue Distribution in Tissue Panels Using PCR

A panel of cDNAs from human tissues was screened for zcytor11 expression using PCR. Commonly owned, human zcytor11 (SEQ ID NO:18, and SEQ ID NO:19) (U.S. Pat. No. 5,965,704) is a receptor for IL-TIF. The panel was made in-house and contained 94 marathon cDNA and cDNA samples from various normal and cancerous human tissues and cell lines are shown in Table 9 above. Aside from the PCR reaction, the method used was as shown in Example 13. The PCR reactions were set up using oligos ZC14,666 (SEQ ID NO:22) and ZC14,742 (SEQ ID NO:23), Advantage 2 cDNA polymerase mix (Clontech, Palo Alto, Calif.), and Rediload dye (Research Genetics, Inc., Huntsville, Ala.). The amplification was carried out as follows: 1 cycle at 94° C. for 2 minutes, 40 cycles of 94° C. for 15 seconds, 51° C. for 30 seconds and 72° C. for 30 seconds, followed by 1 cycle at 72° C. for 7 minutes. The correct predicted DNA fragment size was observed in bladder, brain, cervix, colon, fetal brain, fetal heart, fetal kidney, fetal liver, fetal lung, fetal skin, heart, kidney, liver, lung, melanoma, ovary, pancreas, placenta, prostate, rectum, salivary gland, small intestine, testis, thymus, trachea, spinal cord, thyroid, lung tumor, ovarian tumor, rectal tumor, and stomach tumor. Zcytor11 expression was not observed in the other tissues and cell lines tested in this panel.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. All samples except activated CD8+ and Activated CD19+ showed expression of zcytor11.

B. Tissue Distribution of Zcytor11 in Human Cell Line and Tissue Panels Using RT-PCR A panel of RNAs from human cell lines was screened for zcytor11 expression using RT-PCR. The panels were made in house and contained 84 RNAs from various normal and cancerous human tissues and cell lines as shown in Tables 10-13 above. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC14,666 (SEQ ID NO:22) and ZC14,742 (SEQ ID NO:23), Rediload dye and SUPERSCRIPT One Step RT-PCR System (Life Technologies, Gaithersburg, Md.). The amplification was carried out as follows: one cycle at 50° for 30 minutes followed by 45 cycles of 94°, 15 seconds; 52°, 30 seconds; 72°, 30 seconds; then ended with a final extension at 72° for 7 minutes. 8 to 10 uls of the PCR reaction product was subjected to standard Agarose gel electrophoresis using a 4% agarose gel. The correct predicted cDNA fragment size was observed in adrenal gland, bladder, breast, bronchus, normal colon, colon cancer, duodenum, endometrium, esophagus, gastic cancer, gastro-esophageal cancer, heart ventricle, ileum, normal kidney, kidney cancer, liver, lung, lymph node, pancreas, parotid, skin, small bowel, stomach, thyroid, and uterus. Cell lines showing expression of zcytor11 were A-431, differentiated CaCO2, DLD-1, HBL-100, HCT-15, HepG2, HepG2+ IL6, HuH7, and NHEK #1-4. Zcytor11 expression was not observed in the other tissues and cell lines tested in this panel.

In addition, because the expression pattern of zcytor11, one of IL-TIF's receptors, shows expression in certain specific tissues, binding partners including the natural ligand, IL-TIF, can also be used as a diagnostic to detect specific tissues (normal or abnormal), cancer, or cancer tissue in a biopsy, tissue, or histologic sample, particularly in tissues where IL-TIF receptors are expressed. IL-TIF can also be used to target other tissues wherein its receptors, e.g., zcytor16 and zcytor11 are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

The expression patterns of zcytor11 (above) and zcytor16 (Example 13, and Example 15) indicated target tissues and cell types for the action of IL-TIF, and hence IL-TIF antagonists. The zcytor11 expression generally overlapped with zcytor16 expression in three physiologic systems: digestive system, female reproductive system, and immune system. Moreover, the expression pattern of the receptor (zcytor11) indicated that a IL-TIF antagonist such as zcytor16 would have therapeutic application for human disease in at least two areas: inflammation (e.g., IBD, Chron's disease, pancreatitis) and cancer (e.g., ovary, colon). That is, the polynucleotides, polypeptides and antibodies of the present invention can be used to antagonize the inflammatory, and other cytokine-induced effects of IL-TIF interaction with the cells expressing the zcytor11 receptor.

Moreover, the expression of zcytor11 appeared to be down-regulated or absent in an ulcerative colitis tissue, HepG2 liver cell line induced by IL-6, activated CD8+ T-cells and CD19+ B-cells. However, zcytor16 appeared to be upregulated in activated CD19+ B-cells (Example 12), while zcytor11 is downregulated in activated CD19+ cells, as compared to the resting CD19+ cells (above). The expression of zcytor11 and zcytor16 has a reciprocal correlation in this case. These RT-PCR experiments demonstrate that CD19+ peripheral blood cells, B lymphocytes, express receptors for IL-TIF, namely zcytor11 and zcytor16. Furthermore B cells display regulated expression of zcytor11 and zcytor16. B-lymphocytes activated with mitogens decrease expression of zcytor11 and increase expression of zcytor16. This represents feedback inhibition that would serve to dampen the activity of IL-TIF on B cells and other cells as well. Soluble zcytor16 would act as an antagonist to neutralize the effects of IL-TIF on B cells. This would be beneficial in diseases where B cells are the key players: Autoimmune diseases including systemic lupus erythmatosus (SLE), myasthenia gravis, immune complex disease, and B-cell cancers that are exacerbated by IL-TIF. Also autoimmune diseases where B cells contribute to the disease pathology would be targets for zcytor16 therapy: Multiple sclerosis, inflammatory bowel disease (IBD) and rheumatoid arthritis are examples. Zcytor16 therapy would be beneficial to dampen or inhibit B cells producing IgE in atopic diseases including asthma, allergy and atopic dermatitis where the production of IgE contributes to the pathogenesis of disease.

B cell malignancies may exhibit a loss of the "feedback inhibition" described above. Administration of zcytor16 would restore control of IL-TIF signaling and inhibit B cell tumor growth. The administration of zcytor16 following surgical resection or chemotherapy may be useful to treat minimal residual disease in patients with B cell malignancies. The loss of regulation may lead to sustained or increased expression of zcytor11. Thus creating a target for therapeutic monoclonal antibodies targeting zcytor11.

Example 15

Identification of Cells Expressing Zcytor16 Using In Situ Hybridization

Specific human tissues were isolated and screened for zcytor16 expression by in situ hybridization. Various human tissues prepared, sectioned and subjected to in situ hybridization included cartilage, colon, appendix, intestine, fetal liver, lung, lymph node, lymphoma, ovary, pancreas, placenta, prostate, skin, spleen, and thymus. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at The Laboratory of Experimental Pathology (LEP), NIEHS, Research Triangle Park, N.C.; web address http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 μg/ml) (Boehringer Diagnostics, Indianapolis, Ind.) at 37° C. for 2 to 7 minutes. This step was followed by acetylation and re-hydration of the tissues.

One in situ probe was designed against the human zcytor16 sequence (nucleotide 1-693 of SEQ ID NO:32), and isolated from a plasmid containing SEQ ID NO:32 using standard methods. T3 RNA polymerase was used to generate an antisense probe. The probe was labeled with digoxigenin (Boehringer) using an In Vitro transcription System (Promega, Madison, Wis.) as per manufacturer's instruction.

In situ hybridization was performed with a digoxigenin-labeled zcytor16 probe (above). The probe was added to the slides at a concentration of 1 to 5 pmol/ml for 12 to 16 hours at 62.5° C. Slides were subsequently washed in 2×SSC and 0.1×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Signals were observed in several tissues tested: The lymph node, plasma cells and other mononuclear cells in peripheral tissues were strongly positive. Most cells in the lymphatic nodule were negative. In lymphoma samples, positive signals were seen in the mitotic and multinuclear cells. In spleen, positive signals were seen in scattered mononuclear cells at the periphery of follicles were positive. In thymus, positive signals were seen in scattered mononuclear cells in both cortex and medulla were positive. In fetal liver, a strong signal was observed in a mixed population of mononuclear cells in sinusoid spaces. A subset of hepatocytes might also have been positive. In the inflamed appendix, mononuclear cells in peyer's patch and infiltration sites were positive. In intestine, some plasma cells and ganglia nerve cells were positive. In normal lung, zcytor16 was expressed in alveolar epithelium and mononuclear cells in interstitial tissue and circulation. In the lung carcinoma tissue, a strong signal was observed in mostly plasma cells and some other mononuclear cells in peripheral of lymphatic aggregates. In ovary carcinoma, epithelium cells were strongly positive. Some interstitial cells, most likely the mononuclear cells, were also positive. There was no signal observed in the normal ovary. In both normal and pancreatitis pancreas samples, acinar cells and some mononuclear cells in the mesentery were positive. In the early term (8 weeks) placenta, signal was observed in trophoblasts. In skin, some mononuclear cells in the inflamed infiltrates in the superficial dermis were positive. Keratinocytes were also weakly positive. In prostate carcinoma, scatted mononuclear cells in interstitial tissues were positive. In articular cartilage, chondrocytes were positive. Other tissues tested including normal ovary and a colon adenocarcinoma were negative.

In summary, the in situ data was consistent with expression data described above for the zcytor16. Zcytor16 expression was observed predominately in mononuclear cells, and a subset of epithelium was also positive. These results confirmed the presence of zcytor16 expression in immune cells and point toward a role in inflammation, autoimmune disease, or other immune function, for example, in binding pro-inflammatory cytokines, including but not limited to IL-TIF. Moreover, detection of zcytor16 expression can be used for example as an marker for mononuclear cells in histologic samples.

Zcytor16 is expressed in mononuclear cells, including normal tissues (lymph nodes, spleen, thymus, pancreas and fetal liver, lung), and abnormal tissues (inflamed appendix, lung carcinoma, ovary carcinoma, pancreatitis, inflamed skin, and prostate carcinoma). It is notable that plasma cells in the lymph node, intestine, and lung carcinoma are positive for zcytor16. Plasma cells are immunologically activated lymphocytes responsible for antibody synthesis. In addition, IL-TIF, is expressed in activated T cells. In addition, the expression of zcytor16 is detected only in activated (but not in resting) CD4+ and CD19+ cells (Example 13). Thus, zcytor16 can be used as a marker for or as a target in isolating certain lymphocytes, such as mononuclear leucocytes and limited type of activated leucocytes, such as activated CD4+ and CD19+.

Furthermore, the presence of zcytor16 expression in activated immune cells such as activated CD4+ and CD19+ cells showed that zcytor16 may be involved in the body's immune defensive reactions against foreign invaders: such as microorganisms and cell debris, and could play a role in immune responses during inflammation and cancer formation.

Moreover, as discussed herein, epithelium form several tissues was positive for zcytor16 expression, such as hepatocytes (endoderm-derived epithelia), lung alveolar epithelium (endoderm-derived epithelia), and ovary carcinoma epithelium (mesoderm-derived epithelium). The epithelium expression of zcytor16 could be altered in inflammatory responses and/or cancerous states in liver and lung. Thus, ligand for zcytor16, such as IL-TIF, or a receptor-binding fragment thereof, could be used as marker to monitor changes in these tissues as a result of inflammation or cancer. Moreover, analysis of zcytor16 in situ expression showed that normal ovary epithelium is negative for zcytor16 expression, while it is strongly positive in ovary carcinoma epithelium providing further evidence that IL-TIF polypeptides, or a receptor-binding fragment thereof, can be used as a diagnostic marker and/or therapeutic target for the diagnosis and treatment of ovarian cancers, and ovary carcinoma, as described herein.

Zcytor16 was also detected in other tissues, such as acinar cells in pancreas (normal and pancreatitis tissues), trophoblasts in placenta (ectoderm-derived), chondrocytes in cartilage (mesoderm-derived), and ganglia cells in intestine (ectoderm-derived). As such, zcytor16 may be involved in differentiation and/or normal functions of corresponding cells in these organs. As such, potential utilities of zcytor16 include maintenance of normal metabolism and pregnancy, bone formation/homeostasis, and physiological function of intestine, and the like.

Example 16 huIL-TIF Anti-Peptide Antibodies

Polyclonal anti-peptide antibodies were prepared by immunizing two female New Zealand white rabbits with the peptide, huIL-TIF-1 (SEQ ID NO:34) or huIL-TIF-2 (SEQ ID NO:35) or huIL-TIF-3 (SEQ ID NO:36). The peptides were synthesized using an Applied Biosystems Model 431A peptide synthesizer (Applied Biosystems, Inc., Foster City, Calif.) according to manufacturer's instructions. The peptides huIL-TIF-1, huIL-TIF-2, and huIL-TIF-3 were then conjugated to the carrier protein maleimide-activated keyhole limpet hemocyanin (KLH) through cysteine residues (Pierce, Rockford, Ill.). The rabbits were each given an initial intraperitoneal (IP) injection of 200 µg of conjugated peptide in Complete Freund's Adjuvant (Pierce, Rockford, Ill.) followed by booster IP injections of 100 µg conjugated peptide in Incomplete Freund's Adjuvant every three weeks. Seven to ten days after the administration of the third booster injection, the animals were bled and the serum was collected. The rabbits were then boosted and bled every three weeks.

The huIL-TIF peptide-specific Rabbit seras were characterized by an ELISA titer check using 1 µg/ml of the peptide used to make the antibody as an antibody target. The 2 rabbit seras to the huIL-TIF-1 peptide (SEQ ID NO:34) have titer to their specific peptide at a dilution of 1:5 E6 (1:5,000,000).

The huIL-TIF-1 peptide-specific antibodies were affinity purified from the rabbit serum using an EPOXY-SEPHAROSE 6B peptide column (Pharmacia LKB) that was prepared using 10 mg of the respective peptides per gram EPOXY-SEPHAROSE 6B, followed by dialysis in PBS overnight. Peptide-specific huIL-TIF antibodies were characterized by an ELISA titer check using 1 µg/ml of the appropriate peptide as an antibody target. The huIL-TIF-1 peptide-specific antibodies have a lower limit of detection (LLD) of 500 pg/ml by ELISA on its appropriate antibody target. The huIL-TIF-1 peptide-specific antibodies recognized full-length recombinant protein (BV produced) by reducing Western Blot analysis.

Example 17

Construction of Human IL-TIF Transgenic Plasmids

Approximately 10 µg Zytrack vector containing the sequence confirmed human IL-TIF coding region was digested with FseI and AscI. The vector was then ethanol precipitated and the pellet was resuspended in TE. The released 540 bp human IL-TIF fragment was isolated by running the digested vector on a 1.2% SeaPlaque gel and excising the fragment. DNA was purified using the QiaQuick (Qiagen) gel extraction kit.

The human IL-TIF fragment was then ligated into pTG12-8, our standard transgenic vector, which was previously digested with FseI and AscI. The pTG12-8 plasmid, designed for expression of a gene of interest in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone poly A sequence.

About one microliter of the ligation reaction was electroporated into DH10B ElectroMax® competent cells (GIBCO BRL, Gaithersburg, Md.) according to manufacturer's direction, plated onto LB plates containing 100 µg/ml ampicillin, and incubated overnight at 37° C. Colonies were picked and grown in LB media containing 100 µg/ml ampicillin. Miniprep DNA was prepared from the picked clones and screened for the human IL-TIF insert by restriction digestion with FseI/AscI, and subsequent agarose gel electrophoresis. Maxipreps of the correct pTG12-8 human IL-TIF construct were performed.

A SaiI fragment containing 5' and 3' flanking sequences, the MT promoter, the rat insulin II intron, human IL-TIF cDNA and the human growth hormone poly A sequence was prepared and used for microinjection into fertilized murine oocytes.

A second transgenic construct was made by subcloning as described above, the FseI/AscI fragment containing the human IL-TIF cDNA, into a lymphoid-specific transgenic vector pKFO51. The pKFO51 transgenic vector is derived from p1026X (Iritani, B. M., et al., *EMBO J.* 16:7019-31, 1997) and contains the T cell-specific lck proximal promoter, the B/T cell-specific immunoglobulin Eµ heavy chain enhancer, a polylinker for the insertion of the desired clone, and a mutated hGH gene that encodes an inactive growth hormone protein (providing 3' introns and a polyadenylation signal).

Maxi-prep DNA was digested with NotI, and this fragment, containing the lck proximal promoter, immunoglobulin Eµ enhancer, human IL-TIF cDNA, and the mutated hGH gene was prepared to be used for microinjection into fertilized murine oocytes.

Construction of Mouse IL-TIF Transgenic Plasmids

Transgenic constructs were also made for mouse IL-TIF. Oligonucleotides were designed to generate a PCR fragment containing a consensus Kozak sequence and the exact mouse IL-TIF coding region. These oligonucleotides were designed with an FseI site at the 5' end and an AscI site at the 3' end to facilitate cloning into pKFO51, a lymphoid-specific transgenic vector containing the EuLCK promoter to drive expression of IL-TIF.

PCR reactions were carried out with 200 ng mouse IL-TIF template (SEQ ID NO:37) and oligonucleotides ZC37,125 (SEQ ID NO:39) and ZC37,126 (SEQ ID NO:40). A PCR reaction was performed using Advantage™ cDNA polymerase (Clontech) under the following conditions: 95° C. for 5 minutes; 15 cycles of 95° C. for 60 seconds, 60° C. for 60 seconds, and 72° C. for 90 seconds; and 72° C. for 7 minutes. PCR products were separated by agarose gel electrophoresis and purified using a QiaQuick (Qiagen) gel extraction kit. The isolated, 540 bp, DNA fragment was digested with FseI and AscI (Boerhinger-Mannheim), ethanol precipitated and cloned into pKFO51 as described above. A correct clone of pKFO51 mouse IL-TIF was verified by sequencing, and a maxiprep of this clone was performed and prepared as above for injection.

Example 18

Baculovirus Expression of IL-TIF-CEE

An expression vector, IL-TIF-CEE/pZBV32L, was prepared to express IL-TIF-CEE polypeptides in insect cells. IL-TIF-CEE/pZBV32L was designed to express a IL-TIF polypeptide with a C-terminal GLU-GLU tag (SEQ ID NO:14). This construct can be used to determine the N-terminal amino acid sequence of IL-TIF after the signal peptide has been cleaved off.

A. Construction of IL-TIF-CEE/pZBV32L

A 561 bp IL-TIF fragment containing BamHI and XbaI restriction sites on the 5' and 3' ends, respectively, was generated by PCR amplification from a plasmid containing IL-TIF cDNA using primers ZC28,348 (SEQ ID NO:41) and ZC28,345 (SEQ ID NO:42). The PCR reaction conditions were as follows: 1 cycle at 94° C. for 5 minutes; 35 cycles of 94° C. for 90 seconds, 60° C. for 120 seconds, and 72° C. for 180 seconds; 1 cycle at 72° C. for 10 min; followed by 4° C. soak. The fragment was visualized by gel electrophoresis (1% agarose). The band was excised and then extracted using a QIAquick™ Gel Extraction Kit (Qiagen, Cat. No. 28704). The cDNA was digested using BamHI and XbaI and then was ligated into the vector pZBV32L. The pZBV32L vector is a modification of the pFastBac 1™ (Life Technologies) expression vector, where the polyhedron promoter has been removed and replaced with the late activating Basic Protein Promoter, and the coding sequence for the Glu-Glu tag as well as a stop signal was inserted at the 3' end of the multiple cloning region. Approximately 68 nanograms of the restriction digested IL-TIF insert and about 100 ng of the corresponding pZBV32L vector were ligated overnight at 16° C. The ligation mix was diluted 10 fold in water and 1 fmol of the diluted ligation mix was transformed into ElectoMAX™ DH12s™ cells (Life Technologies, Cat. No. 18312-017) by electroporation at 400 Ohms, 2V and 25 µF in a 2 mm gap electroporation cuvette (BTX, Model No. 620). The transformed cells were diluted in 450 µl of SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) and 100 µl of the dilution were plated onto LB plates containing 100 µg/ml ampicillin. Clones were analyzed by PCR and two positive clones were selected to be outgrown and purified using a QIAprep® Spin Miniprep Kit (Qiagen, Cat. No. 27106). Two µl of each of the positive clones were transformed into 20 µl DH10Bac™ Max Efficiency® competent cells (GIBCO-BRL Cat. No. 10361-012) by heat shock for 45 seconds in a 42° C. heat block. The transformed DH10Bac™ cells were diluted in 980 µl SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) and 100 µl were plated onto Luria Agar plates containing 50 µg/ml kanamycin, 7 µg/ml gentamicin, 10 µg/ml tetracycline, 40 µg/mL IPTG and 200 µg/mL Bluo Gal. The plates were incubated for 48 hours at 37° C. A color selection was used to identify those cells having transposed viral DNA (referred to as a "bacmid"). Those colonies, which were white in color, were picked for analysis. Colonies were analyzed by PCR and positive colonies (containing desired bacmid) were selected for outgrowth and purified using a QIAprep® Spin Miniprep Kit (Qiagen, Cat. No. 27106). Clones were screened for the correct insert by amplifying DNA using primers to the transposable element in the bacmid via PCR using primers ZC447 (SEQ ID NO:43) and ZC976 (SEQ ID NO:44). The PCR reaction conditions were as follows: 1 cycle at 94° C. for 5 minutes; 30 cycles of 94° C. for 60 seconds, 50° C. for 90 seconds, and 72° C. for 180 seconds; 1 cycle at 72° C. for 10 min; followed by 4° C. soak. The PCR product was run on a 1% agarose gel to check the insert size. Those having the correct insert were used to transfect *Spodoptera Frugiperda* (Sf9) cells.

B. Transfection

Sf9 cells were seeded at 1×10$^6$ cells per well in a 6-well plate and allowed to attach for 1 hour at 27° C. Five microliters of bacmid DNA were diluted with 100 µl Sf-900 II SFM (Life Technologies). Twenty µl of Lipofectamine™ Reagent (Life Technologies, Cat. No. 18324-012) were diluted with 100 µl Sf-900 II SFM. The bacmid DNA and lipid solutions were gently mixed and incubated 30-45 minutes at room temperature. The media from one well of cells was aspirated, the cells were washed 1× with 2 µl fresh Sf-900 II SFM media. Eight hundred microliters of Sf-900 II SFM was added to the lipid-DNA mixture. The wash media was aspirated and the DNA-lipid mix added to the cells. The cells were incubated at 27° C. overnight. The DNA-lipid mix was aspirated and 2 µl of Sf-900 II media was added to each plate. The plates were incubated at 27° C., 90% humidity, for 96 hours after which the virus was harvested.

C. Amplification

Sf9 cells were seeded at 1×10$^6$ cells per well in a 6-well plate. 50 µl of virus from the transfection plate were placed in the well and the plate was incubated at 27° C., 90% humidity, for 96 hours after which the virus was harvested.

Sf9 cells were grown in 50 ml Sf-900 II SFM in a 125 ml shake flask to an approximate density of 1×10$^6$ cells/ml. They were then infected with 100 µl of the viral stock from the above plate and incubated at 27° C. for 3 days after which time the virus was harvested.

Example 19

Purification of IL-TIF-CEE from Sf9 Cells

The following procedure was used for purifying IL-TIF polypeptides containing C-terminal Glu-Glu (EE) tags (SEQ ID NO:14), that were expressed in baculovirus. Conditioned media from Sf9 cells expressing IL-TIF-CEE (Example 18) was filtered using a 0.22 µm Steriflip™ filter (Millipore) and one Complete™ protease inhibitor cocktail tablet (Boehringer) was added for every 50 mL of media. Total target protein concentrations of the concentrated conditioned media were determined via SDS-PAGE and Western blot analysis using an anti-EE antibody (produced in-house) followed by a secondary anti-mIg HRP conjugated antibody.

Batch purification was accomplished by adding 250 µl of Protein G Sepharose® 4 Fast Flow (Pharmacia) which was treated with anti-EE antibody (Protein G Sepharose/anti-EE beads), to 40 mLs of Sf9 conditioned media. To capture the IL-TIF-CEE, the media-bead mixture was rocked overnight at 4° C. The beads were spun out of the media at 1000 RPM for 10 minutes in a Beckman GS6R centrifuge. The beads were washed using the following scheme (centrifugation and aspiration steps were done after each wash): 1× with 1 mL cell lysis buffer (150 mM Sodium Chloride, 50 mM Tris pH 8.0, and 1% NP-40); 1× with 1 mL wash buffer (650 mM Sodium Chloride, 50 mM Tris pH 8.0, and 1% NP-40); 1× with 1 mL cell lysis buffer. The beads were then suspended in 500 µl cell lysis buffer and submitted for N-terminal sequencing.

Example 20

N-Terminal Amino Acid Sequence Analysis

Standard automated N-terminal polypeptide sequencing (Edman degradation) was performed using reagents from Applied Biosystems. N-terminal sequence analysis was performed on a Model 494 Protein Sequencer System (Applied Biosystems, Inc., Foster City, Calif.). Data analysis was performed with Model 610A Data Analysis System for Protein Sequencing, version 2.1a (Applied Biosystems).

A purified human IL-TIF-CEE sample was supplied as captured on Protein G Sepharose/anti-EE beads (Example 19). The beads were placed in reducing SDS PAGE sample buffer and on a boiling water bath before running on SDS PAGE, using a Novex SDS PAGE system (4-12% Bis-Tris MES NuPAGE; Invitrogen) as per manufacturer's instructions. The gel was electrotransferred to a Novex PVDF membrane (Invitrogen), and Coomassie blue stained (Sigma, St. Louis, Mo.) using standard methods. Corresponding anti-EE Western blots were performed to identify the IL-TIF band for N-terminal protein sequencing. The mouse anti-EE IgG HRP conjugated antibody used was produced in house.

N-terminal sequence analysis of the secreted IL-TIF polypeptide verified the predicted cleavage site of the signal sequence resulting in a mature start of the IL-TIF precursor sequence at 22 (Ala) as shown in SEQ ID NO:3.

Example 21

Construction of BaF3 Cells Expressing the CRF2-4 Receptor (BaF3/CRF2-4 Cells) and BaF3 Cells Expressing the CRF2-4 Receptor with the Zcytor11 Receptor (BaF3/CRF2-4/Zcytor11 Cells)

BaF3 cells expressing the full-length CFR2-4 receptor were constructed, using 30 µg of a CFR2-4 expression vector, described below. The BaF3 cells expressing the CFR2-4 receptor were designated as BaF3/CFR2-4. These cells were used as a control, and were further transfected with full-length zcytor11 receptor (SEQ ID NO:18 and SEQ ID NO:19) (U.S. Pat. No. 5,965,704) and used to construct a screen for IL-TIF activity as described below. This cell assay system can be used to assess IL-TIF activity and readily screen for the activity of IL-TIF variants.

A. Construction of BaF3 Cells Expressing the CRF2-4 Receptor

The full-length cDNA sequence of CRF2-4 (Genbank Accession No. Z17227) was isolated from a Daudi cell line cDNA library, and then cloned into an expression vector pZP7P using standard methods.

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, CRF2-4/pZP7P was prepared and purified using a Qiagen Maxi Prep kit (Qiagen) as per manufacturer's instructions. For electroporation, BaF3 cells were washed once in serum-free RPMI media and then resuspended in serum-free RPMI media at a cell density of $10^7$ cells/ml. One ml of resuspended BaF3 cells was mixed with 30 µg of the CRF2-4/pZP7P plasmid DNA and transferred to separate disposable electroporation chambers (GIBCO BRL). Following a 15-minute incubation at room temperature the cells were given two serial shocks (800 1Fad/300 V.; 1180 1Fad/300 V.) delivered by an electroporation apparatus (CELL-PORATOR™; GIBCO BRL). After a 5-minute recovery time, the electroporated cells were transferred to 50 ml of complete media and placed in an incubator for 15-24 hours (37° C., 5% $CO_2$). The cells were then spun down and resuspended in 50 ml of complete media containing 2 µg/ml puromycin in a T-162 flask to isolate the puromycin-resistant pool. Pools of the transfected BaF3 cells, hereinafter called BaF3/CRF2-4 cells, were assayed for signaling capability as described below. Moreover these cells were further transfected with zcytor11 receptor as described below.

B. Construction of BaF3 Cells Expressing CRF2-4 and Zcytor11 Receptors

BaF3/CRF2-4 cells expressing the full-length zcytor11 receptor were constructed as per Example 21A above, using 30 µg of an expression vector containing zcytor11 cDNA (SEQ ID NO:18). Following recovery, transfectants were selected using 200 µg/ml zeocin and 2 µg/ml puromycin. The BaF3/CRF2-4 cells expressing the zcytor11 receptor were designated as BaF3/CRF2-4/zcytor11 cells. These cells were used to screen for IL-TIF activity (Example 22).

Example 22

Screening for IL-TIF Activity Using BaF3/CRF2-4/Zcytor11 Cells Using an Alamar Blue Proliferation Assay A. Screening for IL-TIF Activity Using BaF3/CRF2-4/Zcytor11 Cells Using an Alamar Blue Proliferation Assay Purified IL-TIF-CEE (Example 9) was used to test for the presence of proliferation activity as described below BaF3/CRF2-4/zcytor11 cells were spun down and washed in the complete media, described in Example 21A above, but without mIL-3 (hereinafter referred to as "mIL-3 free media"). The cells were spun and washed 3 times to ensure the removal of the mIL-3 Cells were then counted in a hemacytometer. Cells were plated in a 96-well format at 5000 cells per well in a volume of 100 µl per well using the mIL-3 free media.

Proliferation of the BaF3/CRF2-4/zcytor11 cells was assessed using IL-TIF-CEE protein diluted with mIL-3 free media to 50, 10, 2, 1, 0.5, 0.25, 0.13, 0.06 ng/ml concentrations. 100 µl of the diluted protein was added to the BaF3/CRF2-4/zcytor11 cells. The total assay volume is 200 µl. The assay plates were incubated at 37° C., 5% $CO_2$ for 3 days at which time Alamar Blue (Accumed, Chicago, Ill.) was added at 20 µl/well. Plates were again incubated at 37° C., 5% $CO_2$ for 24 hours. Alamar Blue gives a fluourometric readout based on number of live cells, and is thus a direct measurement of cell proliferation in comparison to a negative control. Plates were again incubated at 37° C., 5% $CO_2$ for 24 hours. Plates were read on the Finax™ plate reader (Molecular Devices Sunnyvale, Calif.) using the SoftMax™ Pro program, at wavelengths 544 (Excitation) and 590 (Emmission). Results confirmed the dose-dependent proliferative response of the BaF3/CRF2-4/zcytor11 cells to IL-TIF-CEE. The response, as measured, was approximately 15-fold over background at the high end of 50 ng/ml down to a 2-fold induction at the low end of 0.06 ng/ml. The BaF3 wild type cells, and BaF3/CRF2-4 cells did not proliferate in response to IL-TIF-CEE, showing that IL-TIF is specific for the CRF2-4/zcytor11heterodimeric receptor.

Example 23

IL-TIF-Expressing Transgenic Mice

A. Generation of Transgenic Mice Expressing Mouse IL-TIF

DNA fragments from a transgenic vector containing 5' and 3' flanking sequences of the lymphoid specific EµLCK promoter, mouse IL-TIF (SEQ ID NO:37; polypeptide shown in SEQ ID NO:38), the rat insulin II intron, IL-TIF cDNA and the human growth hormone poly A sequence were prepared using standard methods, and used for microinjection into fertilized B6C3f1 (Taconic, Germantown, N.Y.) murine oocytes, using a standard microinjection protocol. See, Hogan, B. et al., *Manipulating the Mouse Embryo. A Laboratory Manual*, Cold Spring Harbor Laboratory Press, 1994.

Twenty-five mice transgenic for mouse IL-TIF with the lymphoid-specific EµLCK promoter were identified among 154 pups. Eleven of the transgenic pups died within hours of birth, 9 transgenic pups with a shiny appearance were necropsied the day of birth, and 2 grew to adulthood. Expression levels were low in one adult animal. Tissues from the necropsied pups were prepared and histologically examined as described below.

The shiny appearance of the neonate pups appeared to be associated with a stiffening of the skin, as if they were drying out, resulting in a reduction of proper nursing. Their movements became stiffened in general.

B. Genotypic and Expression Analysis from Transgenic Mice

From the mouse IL-TIF transgenic line driven by the EµLck promoter, described above, newborn pups were observed for abnormalities on day one (day of birth) and sacrificed for tissue collection. All pups were given a unique ear tag number, and those designated as having a shiny skin phenotype at the time of sacrifice were noted. Of the twelve pups, six were observed to have the shiny skin phenotype, with two designated as "severe" phenotypes. Severe phenotypes were defined as small pups with little mobility whose skin was especially shiny and very dry. Skin was collected from the left lateral side of each pup, and frozen in Tissue-Tek embedding medium.

Genotyping confirmed that shiny skin was a good indicator of transgenic status, although no expression data was collected. Frozen skin blocks were sectioned to 7 microns on a cryostat and stained to look for the presence of CD3, CD4, CD8, mouse macrophages, B-cells, CD80, and MHC class II. The staining protocol involved binding of commercially available antibodies to the tissue, detection with a peroxidase labeled secondary antibody, and DAB chromogen reaction to visualize staining.

Transgenic animals were found to be higher in MHC class II and CD80, which stain for antigen-presenting cells and dendritic cells respectively. The macrophage marker also detected more cells in the severe and non-severe transgenics than in the wild type animals, although the distribution of these cells was very localized in the high dermis. Animals classified as severe phenotypes had the most robust staining with all three of these markers, showing a dramatic increase in cell intensity and number when compared to the wild type. This variability may be due to a difference in expression level of IL-TIF in these transgenic founder pups. The MHC class II positive cells were located in the lower dermis arranged in loose open clusters, while the CD80 positive cells were predominantly below the dermis either in or just above the muscle/fat layer. These two cell populations do not appear to overlap. All other markers were of equivalent staining in all animals. Toluidine blue staining for mast cells revealed slight to no difference between wild type and transgenic animals.

C. Microscopic Evaluation of Tissues from Transgenic Mice: IL-TIF TG with Eulck Promoter has a Neonatal Lethal-Histology On the day of birth, pups from litters containing IL-TIF transgenics were humanely euthanized and the whole body immersion fixed in 10% buffered formalin. Six transgenic and two non-transgenic pups were submitted for further workup. Four of the six transgenics were noted to have shiny skin at the time of euthanasia. The fixed tissues were trimmed into 5 sections (longitudinal section of the head and cross sections of the upper and lower thorax and upper and lower abdomen). The tissues were embedded in paraffin, routinely processed, sectioned at 5 um (Jung 2065 Supercut microtome, Leica Microsystems, Wetzlar, Germany) and stained with H&E. The stained tissues were evaluated under a light microscope (Nikon Eclipse E600, Nikon Inc., Melville, N.Y.) by a board (ACVP) certified veterinary pathologist.

On microscopic examination, the epidermis of two of the transgenic pups was observed to be thicker than the epidermis of the other six mice including the controls. No other abnormalities were noted in the skin and other tissues of any of the mice. Representative areas of skin from corresponding regions of the thorax and abdomen were imaged with the 40× objective lens and with a CoolSnap digital camera (Roper Scientific, Inc., San Diego, Calif.) that was attached to the microscope. The thickness of the epidermis was then determined using histomorphometry software (Scion Image for Windows (NIH Image), Scion Corp., Frederick, Md., v. B4.0.2). The results, shown in Table 14, were as follows:

TABLE 14

| Genotype/phenotype | Average thoracic skin thickness (μm) | Average abdominal skin thickness (μm) |
| --- | --- | --- |
| Non-transgenic/normal | 5.2 | 5.4 |
| Transgenic/non-shiny | 5.0 | 6.7 |
| Transgenic/shiny | 8.2 | 7.4 |
| Transgenic/all | 7.1 | 7.1 |

There were insufficient numbers of mice to determine statistical significance; however, the transgenics, especially those with shiny skin, tended to have a thicker epidermis than the non-shiny transgenics and non-transgenic controls. The shiny transgenics may have a higher expression level of IL-TIF than the non-shiny transgenics; however, expression levels were not determined for these mice.

Example 24

In Vivo Affects of IL-TIF Polypeptide

A. Mice Infected with IL-TIF Adenovirus Show Induction of SAA

Mice (female, C57B1, 8 weeks old; Charles River Labs, Kingston, N.Y.) were divided into three groups. An adenovirus expressing an IL-TIF polypeptide (SEQ ID NO:3) was previously made using standard methods. On day 0, parental or IL-TIF adenovirus was administered to the first (n=8) and second (n=8) groups, respectively, via the tail vein, with each mouse receiving a dose of $\sim 1 \times 10^{11}$ particles in $\sim 0.1$ ml volume. The third group (n=8) received no treatment. On day 12, mice were weighed and blood was drawn from the mice. On day 20 of the study, mice were sacrificed, body weight was recorded, and blood and tissues were collected for analysis.

All blood samples were analyzed for complete blood count (CBC) and serum chemistry. At both day 12 and 20, statistically significant elevations in neutrophil and platelet counts were detected in the blood samples from the IL-TIF adenovirus administered group relative to the parental adenovirus treated group. Also, lymphocyte counts were significantly reduced from the IL-TIF adenovirus administered group relative to the parental adenovirus treated group at day 12, but at day 20 the opposite effect was observed. In addition, the IL-TIF adenovirus treated mice decreased in body weight, while parental adenovirus treated mice gained weight. Glucose was significantly reduced at both time points in the serum samples from the IL-TIF adenovirus administered group relative to the parental adenovirus treated group. Serum albumin was also significantly reduced at both time points. Blood urea nitrogen levels were significantly reduced at day 20. Serum globulin levels were significantly increased the IL-TIF adenovirus administered group relative to the parental adenovirus treated group at both time points. Microscopically, one observed histomorphological change attributed to IL-TIF was tubular regeneration in the kidney. While not uncommon in mice, there was an increased incidence and severity in this group of animals. Nephropathy is characterized as multifocal areas of basophilia of cortical tubular epithelial cells.

An additional experiment, identical in design to the one described above, was carried out in order to verify results and collect additional samples. In this study, body weight was recorded every three days, blood was collected from the mice 3 days following adenovirus injection, and mice were sacrificed for blood and tissue collection on day 10 (n=4 per group) and day 20 (n=4 per group). Elevated neutrophil and platelet counts were again detected in blood samples from the IL-TIF adenovirus administered group relative to the parental adenovirus treated group. This effect was evident for neutrophils by day 3, but platelet count was not significantly different until day 10. Also, lymphocyte counts were significantly reduced from the IL-TIF adenovirus administered group relative to the parental adenovirus treated group at 3 and 10, but they were not elevated on day 20 as in the previous study. Again, mice given IL-TIF adenovirus lost weight over the course of the study, while control virus treated and untreated mice gained weight. Serum chemistry parameters were consistent with the previous study. Histological findings of tubular regeneration in the kidney associated with IL-TIF adenovirus treatment were also confirmed in this study. This was consistent with the additional finding of moderate proteinurea in mice given IL-TIF adenovirus (day 20).

The results suggested that IL-TIF affects hematopoiesis, i.e., blood cell formation in vivo. As such, IL-TIF could have biological activities effecting different blood stem cells, thus resulting in an increase or decrease of certain differentiated blood cells in a specific lineage. For instance, IL-TIF appears to reduce lymphocytes, which is likely due to inhibition of the committed progenitor cells that give rise to lymphoid cells, supporting the notion that IL-TIF could play a role in anemia, infection, inflammation, and/or immune diseases by influencing blood cells involved in these processes. Antagonists against IL-TIF, such as antibodies or its soluble receptor zcytor16, could be used as therapeutic reagents in these diseases.

Moreover, these experiments using IL-TIF adenovirus in mice suggest that IL-TIF over-expression increases the level of neutrophils and platelets in vivo. It is conceivable that there are other factors (such as cytokines and modifier genes) involved in the responses to IL-TIF in the whole animal system. Nevertheless, these data strongly support the involvement of IL-TIF in hematopoiesis. Thus, IL-TIF, anti-IL-TIF antibodies, and its receptors, such as zcytor16 and soluble zcytor11/CRF2-4, are suitable reagents/targets for the diagnosis and treatment in variety of disorders, such as inflammation, immune disorders, infection, anemia, hematopoietic and other cancers, and the like.

Association of IL-TIF expression with weight loss, appearance of acute phase protein SAA, and metabolic perturbations evidenced by decreased serum glucose, albumin and urea nitrogen suggest that IL-TIF is a cytokine which acts early in certain inflammatory responses. Mice given IL-TIF adenovirus may represent a state of chronic inflammation, such as that observed in IBD, ulcerative colitis, arthritis, psoriasis, asthma, and the like. Certain detrimental inflammatory processes might be inhibited by use of an antagonist to IL-TIF, such as anti-IL-TIF antibodies, and its receptors, such as zcytor16 and soluble zcytor11/CRF2-4, and the like.

B. IL-TIF is a Pro-Inflammatory Cytokine: Serum Level of SAA in Adeno-IL-TIF Mice:

An ELISA was performed to determine the level of SAA in IL-TIF-Adeno mice, using a Mouse SAA Immunoassay Kit and protocol (Biosource International, California, USA). Diluted standards and unknowns were plated along with HRP-anti-mouse SAA into assay plates pre-coated with anti-mouse SAA antibody. Plates were incubated for one hour at 37 degrees C. and then washed according to kit instructions. Plates were developed for 15 minutes at room temperature using TMB and stopped with 2M $H_2SO_4$. The absorbance at 450 nm was read using a Spectromax 190 (Molecular Devices, California, USA). The resulting data was analyzed using Softmax Pro (Molecular Devices, California, USA) and Excel (Microsoft Corp., Washington, USA).

Mice infected with IL-TIF-Adenovirus had highly elevated levels of mSAA, over 10-fold, relative to the Parental-Adenovirus control.

C. Flow Cytometry Analysis of IL-TIF-Adenovirus Infected Mice

To analyze the effects of IL-TIF expression in vivo by adenovirus, we isolated peripheral blood, spleen, and bone marrow from IL-TIF-adenovirus infected C57BL/6 mice, at day 10 and day 20 after infection. Approximately 100 μl of blood was collected in heparinized tubes, then depleted of red blood cells by hypotonic lysis (cells were lysed in 4.5 ml $dH_2O$ for ~5 seconds before adding 1.5 ml 3.6% NaCl). Spleens were crushed between two frosted glass slides, and the cells released were passed over a Nytex membrane (cell strainer) and pelleted. Bone marrow was obtained by crushing one femur in a mortar and pestle and passing the cells over a cell strainer (Falcon). Cells were resuspended in FACS wash buffer (WB=HBSS/1% BSA/10 mM hepes), counted in trypan blue, and $1 \times 10^6$ viable cells of each type were aliquoted into 5 ml polystyrene tubes. Cells were washed and pelleted, then incubated for 20 min on ice with cocktails of fluorescently-labeled (FITC, PE, and CyChrome) monoclonal antibodies (PharMingen, San Diego, Calif.) recognizing various cell surface markers used to identify particular immune cell subsets. These markers include the following (listed in the groups of 3 we tested). For blood staining: CD3, Gr1, and B220; for spleen staining. CD62L, CD44, and CD3; CD21, CD23, and B220; IgD, IgM, and B220; CD11b, Gr1, and CD8; for bone marrow staining. CD11b, Gr1, CD3; IgD, IgM, and B220. Cells were washed with 1.5 ml WB and pelleted, then resuspended in 0.4 ml of WB and analyzed on a FACScan using CellQuest software (Becton Dickinson, Mountain View, Calif.).

We found that the fraction of neutrophils in the blood of IL-TIF-adeno-treated mice was elevated 4-13 fold at Day 10 and 2-3-fold at Day 20. At Day 10, this difference resulted in a concomitant decrease in the fraction of lymphocytes and monocytes in the blood. In the bone marrow, we found that the total number of B cells decreased ~1.5-fold while the percentage of mature recirculating B cells increased and the total number of immature B cells dropped slightly at Day 10. At Day 20, many of these differences were not apparent, though we did find a slight increase in the fraction of mature recirculating B cells. In the spleen, the total number of B cells decreased slightly (1.5-2-fold) on both days tested, while on Day 20, the fraction of marginal zone B cells (CD21+ CD23- B220+) increased by 2-fold and the number of follicular B cells (CD21+ CD23+ B220+) dropped 2-fold. Marginal zone B cells are considered to be the first line of defense against pathogens, as they are more sensitive to B cell mitogens (e.g. LPS) than the more common follicular B cells, and when they encounter their cognate antigen they differentiate very quickly into antibody-secreting cells. It is possible that IL-TIF either enhances the conversion of follicular to marginal zone B cells, or that it selectively depletes the less mature follicular cells. The changes in B cell numbers found in the bone marrow may reflect an enhanced differentiation of pre/pro and/or immature B cells, or an increased influx of recirculating B cells from the blood/spleen, and perhaps a coincident increase in export of immature B cells to the periphery. The actual number of mature BM B cells does not increase, so IL-TIF may not enhance their proliferation. Alternatively, IL-TIF may block differentiation of immature B cells and thereby increase the relative representation of mature B cells.

D. Zcytor16/Fc4 Neutralizes IL-TIF Activity In Vivo: SAA ELISA Showing SAA Expression Induced by IL-TIF is Inhibited by Zcytor16-Fc4 Injection:

To assess whether zcytor16 could inhibit the SAA induction by IL-TIF mice (female, C3H/HEJ, 8 weeks old; Jackson Labs, Bar Harbor, Me.) were divided into five groups of three animals each and treated by IP injection of proteins as shown in Table 15 below:

TABLE 15

| roup # | L-TIF | cytor16 |
|---|---|---|
| Group 1: | — | — |
| Group 2: | — | 100 μg |
| Group 3: | 3 μg | — |
| Group 4: | 3 μg | 20 μg |
| Group 5: | 3 μg | 100 μg |

The zcytor16 injections preceded the IL-TIF injection by 15 minutes. Both protein injections were given by the intraperitoneal route. A blood sample was taken from each mouse prior to treatment, then at 2 and 6 hours after treatment. Serum was prepared from each of the samples for measurement of SAA and IL-TIF.

An ELISA was performed as described previously to determine the level of SAA in mice treated with IL-TIF and a soluble receptor for IL-TIF, zcytor16-Fc4 described herein. Mice treated with 3 µg IL-TIF in conjunction with zcytor16-Fc4 at concentrations between 20-100 ug showed a reduction in the level of SAA induced by IL-TIF alone to background levels, demonstrating that zcytor16 inhibited the SAA induction activity of IL-TIF in vivo.

Example 25

Expression of IL-TIF in Inflammatory Bowel Disease Mouse Model

Inflammatory Bowel disease (IBD) is a multifactorial disease, divided into two types, ulcerative colitis (UC) and Crohn's Disease (CD). The etiology of these diseases is currently not known and clinical manifestations differ. UC is restricted to the colon, and symptoms include bloody diarrhea, weight loss and abdominal pain. Macroscopic features of UC include punctuated ulcers and a shortened colon. In contrast, Crohn's Disease can also affect other parts of the bowel. Symptoms include diarrhea (which is less often bloody than seen in UC), a low-grade fever and pain. Macroscopic features include fibrotic and stenotic bowel with strictures, deep ulcers, fissures and fistulas.

Several animal models are available that mimic these human diseases. Three commonly used models of colitis for new drug screening are the 2,4,6-trinitrobenzene sulphonic acid (TNBS) induced rat model, the mouse T-cell transfer model, and the dextran sodium sulfate, or DSS-induced mouse model. The DSS model was derived from a model by Dr. S. Murthy, using a disease activity index scoring system (S. N. S. Murthy, *Treatment of Dextran Sulfate Sodium-Induced Murine Colitis by Intracolonic Cyclosporin*, Digestive Diseases and Sciences, Vol. 38, No. 9 (September 1993), pp. 1722-1734).

In the present study, an acute colitis resulted when mice were fed DSS in their drinking water for 6 days. The animals exhibited weight loss and bloody diarrhea, mimicking the condition of UC patients. The mechanism of the DSS injury is not well characterized, but it is thought that it induces a nonspecific inflammatory immune response and mimics environmental effects on the bowel. It is possible that $H_{2}S$ is produced, which could be toxic to cells. In addition, changes in luminal bacterial flora occur. Activated monocytes, macrophages and mast cells have been demonstrated in the colon. Mediators for all three animal models include inflammatory prostaglandins, leukotriene metabolites and cytokines.

A. Method

Colitis was induced by DSS ingestion in Swiss Webster female mice from Charles River Laboratories. The mice were 10 and 11 weeks old at the start of the study. Mice were given 4% DSS in the drinking water for a period of 6 days (treated mice), or were given only normal drinking water (control mice). A Disease Activity Index clinical score (DAI) was used, which comprises a combination of measurements including stool quality, occult blood and weight loss. DAI was obtained daily for each mouse beginning one day after DSS treatment. After 6 days, DSS was removed from the drinking water of the treated mice. All mice were monitored by DAI clinical score until sacrifice at either 2, 7 or 10 days from the start of the study. On each of days 2 and 7, four DSS-treated mice and one control mouse were sacrificed. On day 10, four DSS-treated mice and two control mice were sacrificed. For all animals after sacrifice, the colon length was measured. Colon sections were fixed in 10% neutral buffered formalin for histologic analysis or frozen for mRNA extraction.

B. Histologic Scoring and Disease Activity Index (DAI) Scoring

Histologic index scores were obtained following the method in reference 1. Generally, the colon sections were scored blinded by a pathologist for crypt scores, hyperplastic epithelium, crypt distortion and inflammation.

Daily, each mouse was graded as to a clinical score based on weight loss, stool consistence and intestinal bleeding. Higher scores were assigned for increasing amounts of weight loss, diarrhea and bleeding. The daily score for each mouse was the mean grade obtained from the three results/observations.

C. Results

The colon lengths for DSS-treated mice were somewhat shorter on days 7 and 10 than non-treated controls, but the results may not have been significant (not checked by a statistical application). The clinical DAI scores reflected a rise in disease symptoms in the DSS-treated mice similar to that seen in past studies using this model. Occult blood was greatest on approximately days 4 and 5, while loose stools were more prevalent on days 6 and 7. Histopathology results show that disease scores were different from the controls on all sacrifice days, especially days 7 (peak) and 10. The histopathology screening scores were: controls=0.5, day 2 DSS-treated mice=8.8, day 7 DSS-treated mice=21, day 10 DSS-treated mice=18. Clinical and histopathology scores show that the DSS-treated mice had significant colon disease relative to the non-treated controls. The frozen tissue samples were used later for mRNA determinations as described below.

D. Tissue Expression of IL-TIF RNA in Murine IBD Colon Samples using RT-PCR:

To determine the relative expression of mouse IL-TIF RNA (SEQ ID NO:37) in an inflammatory bowel disease model, the distal colons of DSS-treated mice were collected and snap frozen in liquid nitrogen. In this experiment mice were treated with DSS and samples were taken on days 2, 7 and 10 post-treatment. Samples from normal untreated mice were collected as well. RNA was then isolated from the samples using the standard RNeasy Midiprep™ Kit (Qiagen, Valencia, Calif.) as per manufacturer's instructions.

The RT-PCR reactions used the 'Superscript One-Step RT-PCR System with Platinum Taq.' (Life Technologies, Gaithersburg, Md.) Each 25 µl reaction consisted of the following: 12.5 µl of 2× Reaction Buffer, 0.5 µl (20 pmol/µl) ZC39,289 (SEQ ID NO:45), 0.5 µl (20 pmol/µl) ZC39,290 (SEQ ID NO:46), 0.4 µl RT/Taq polymerase mix, 10 ul RNase-free water, 1.0 µl total RNA (100 ng/µl). The amplification was carried out as follows: one cycle at 50° for 30 minutes followed by 35 cycles of 94°, 30 seconds; 58°, 30 seconds; 72°, 60 seconds; then ended with a final extension at 72° for 7 minutes. 8 to 10 µl of the PCR reaction product was subjected to standard agarose gel electrophoresis using a 2% agarose gel. The correct predicted cDNA fragment size was observed as follows: There was a faint band in both day 2 samples. Two of three day 7 samples generated a strong band while the third day 7 sample generated a very strong band. The three day 10 samples generated a strong band. Finally, the two 'normal' control samples didn't generate any band. These results suggest that there may be an upregulation of IL-TIF in certain types of inflammatory responses in the colon, including those associated with IBD, UC, and CD. The data is summarized in Table 16 below where Relative Expression was scored as follows: 0=No band, 1=faint band, 2=strong band, 3=very strong band.

TABLE 16

| Tissue | Relative Expression (0-3) |
| --- | --- |
| Normal Colon | 0 |
| Normal Colon | 0 |
| Day 2 Post Treatment | 1 |
| Day 2 Post Treatment | 1 |
| Day 7 Post Treatment | 3 |
| Day 7 Post Treatment | 2 |
| Day 7 Post Treatment | 2 |
| Day 10 Post Treatment | 2 |
| Day 10 Post Treatment | 2 |
| Day 10 Post Treatment | 2 |

Example 26

Construct for Generating Hzcytor11/hCRF2-4 Heterodimer

A cell line expressing a secreted Hzcytor11/hCRF2-4 heterodimer was constructed. In this construct, the extracellular domain of hzcytor11 (SEQ ID NO:47) was fused to the heavy chain of IgG gamma1 (Fc4) (SEQ ID NO:64) with a Glu-Glu tag (SEQ ID NO:60) at the C-terminus, while the extracellular domain of CRF2-4 (SEQ ID NO:48) was fused to Fc4 with a His tag (SEQ ID NO:61) at the C-terminus. For both of the hzcytor11 and hCRF2-4 arms of the heterodimer, a Gly-Ser spacer of 8 amino acids (SEQ ID NO:49) was engineered between the extracellular portion of the receptor and the n-terminus of Fc4. In addition, a thrombin cleavage site was engineered between the Fc4 domain and the c-terminal tag to enable possible proteolytic removal of the tag.

For construction of the hzcytor11/Fc4-CEE portion of the heterodimer, the extracellular portion of hzcytor11 was PCRed from a vector containing human zcytor11 fused of Fc4 (hzcytor11/IgG) with oligos ZC39335 (SEQ ID NO:50) and ZC39434 (SEQ ID NO:51) with EcoRI and BamHI restriction sites engineered at the 5' and 3' ends, respectively, under conditions as follows: 25 cycles of 94° C. for 60 sec., 57° C. for 60 sec., and 72° C. for 120 sec.; and 72° C. for 7 min. PCR products were purified using QIAquick PCR Purification Kit (Qiagen), digested with EcoRI and BamHI (Boerhinger-Mannheim), separated by gel electrophoresis and purified using a QIAquick gel extraction kit (Qiagen). The hzcytor11 EcoRI/BamHI fragment was ligated into pZP-9 hzcytor7/Fc4-TCS-CEE that had been digested with EcoRI and BamHI. This vector has the extracellular portion of hzcytor7 (U.S. Pat. No. 5,945,511) fused to Fc4 (SEQ ID NO:64) with a CEE tag (SEQ ID NO:59), and digesting with EcoRI and BamHI removes the extracellular portion of hzcytor7 and allows substitution of hzcytor11. Minipreps of the resulting ligation were screened for an EcoRI/BamHI insert of the correct size and positive minipreps were sequenced to confirm accuracy of the PCR reaction. The polypeptide sequence of the hzcytor11/Fc4-CEE fusion polypeptide is shown in SEQ ID NO:62.

For construction of the hCRF2-4/Fc4-cHIS portion of the heterodimer, the extracellular portion of hCRF2-4 was PCRed from pZP-9 CRF with oligos ZC39,319 (SEQ ID NO:52) and ZC39,325 (SEQ ID NO:53) under conditions as follows: 30 cycles of 94° C. for 60 sec., 57° C. for 60 sec., and 72° C. for 120 sec; and 72° C. for 7 min. PCR product were purified as described above and then digested with EcoRI and BamHI. Because the PCR product had an internal EcoRI site two bands were obtained upon digestion; a 0.101 kB EcoRI/EcoRI fragment and a 0.574 kB EcoRI/BamHI fragment. The 0.574 EcoRI/BamHI fragment was ligated into vector pHZ-1DR1/Fc4-TCS-cHIS that had been digested with EcoRI and BamHI. This vector has the extracellular portion of hDR-1 fused to Fc4 with a C-HIS tag (SEQ ID NO:61), and digesting with EcoRI and BamHI removes the extracellular portion of hDR-1 and allows substitution of hCRF2-4. Minipreps of the resulting ligation were screened for an EcoRI/BamHI insert of the correct size, and positive minipreps, were EcoRI digested and band purified for further construction. The 0.101 kB EcoRI/EcoRI fragment was ligated into the EcoRI digested minipreps and clones were screened for proper orientation of insertion by KpnI/NdeI restriction digestion. Clones with the correct size insertion were submitted for DNA sequencing to confirm the accuracy of the PCR reaction. The polypeptide sequence of the hzcytor11/Fc4-CEE fusion polypeptide is shown in SEQ ID NO:62.

About 16 µg each of the hzcytor11/Fc4-cEE and hCRF2-4/Fc-4-cHIS were co-transfected into BHK-570 (ATCC No. CRL-10314) cells using Lipofectamine (Gibco/BRL), as per manufacturer's instructions. The transfected cells were selected for 10 days in DMEM+5% FBS (Gibco/BRL) containing 1 µM methotrexate (MTX) (Sigma, St. Louis, Mo.) and 0.5 mg/ml G418 (Gibco/BRL) for 10 days. The resulting pool of transfectants was selected again in 10 µM MTX and 0.5 mg./ml G418 for 10 days.

Example 27

Purification of Zcytor11/CRF2-4 Heterodimer Receptor

Conditioned culture media zcytor11/CRF2-4 heterodimer was filtered through 0.2 µm filter and 0.02% (w/v) Sodium Azide was added. The conditioned media was directly loaded a Poros Protein A 50 Column at 10-20 ml/min Following load the column was washed with PBS and the bound protein eluted with 0.1M Glycine pH 3.0. The eluted fractions containing protein were adjusted to pH 7.2 and Concentrated to <80 ml using YM30 Stirred Cell Membrane (Millipore).

The 80 ml eluate from the Protein A column was loaded onto a 318 ml Superdex 200 HiLoad 26/60 Column (Pharmacia). The column was eluted with PBS pH 7.2 at 3 ml/min. Protein containing fractions were pooled to eliminate aggregates. The Superdex 200 pool was adjusted to 0.5M NaCl, 10 mM Imidazole using solid NaCl and Imidazole and the pH was adjusted to 7.5 with NaOH. The adjusted protein solution was loaded onto a 200 ml NiNTA column (Qiagen) at 2 CV/hr. The bound protein was eluted, following PBS wash of the column, with five concentration steps of Imidazole: 40 mM, 100 mM, 150 mM, 250 mM, 500 mM. The fractions eluted at each step of imidizole were pooled and analyzed by N-terminal sequencing. Pools containing heterodimer, determined by sequencing were pooled and concentrated to 50 ml using a YM30 Stirred Cell Membrane (Millipore). The 50 ml eluate from the NiNTA column was loaded onto a 318 ml Superdex 200 HiLoad 26/60 Column (Pharmacia). The column was eluted with PBS pH 7.2 at 3 ml/min. Protein containing fractions were pooled to eliminate aggregates, as determined by SEC MALS analysis.

Purified proteins were analyzed by N-terminal sequencing, amino acid analysis, and SEC-MALS. Binding affinities and biological activities were determined.

Example 28

Comparison of Zcytor16-Fc4 Activity with CRF2-4/Zcytor11-Fc4 Activity Using BaF3/CRF2-4/Zcytor11 Cells in an Alamar Blue Proliferation Assay BaF3/CRF2-4/zcytor11 cells described herein were spun down and washed in PBS 2 times to ensure the removal of the mIL-3, and then spun a third time and re-suspended in the complete media (RPMI 1640, 10% FBS, 1% GlutaMAX, 1% Sodium Pyruvate), but without mIL-3 (hereinafter referred to as "mIL-3 free media"). Cells were then counted in a hemocytometer. Cells were plated in a 96-well format at 5000 cells per well in a volume of 100 µl per well using the mIL-3 free media.

IL-TIF protein (SEQ ID NO:3) was diluted to 200 pg/ml in mIL-3 free media. Zcytor16-Fc4 fusion protein (described herein) was diluted to 1 µg/ml in the mIL-3 free/IL-TIF media on the top row of the plate, and then diluted serially 1:2 down the remaining 7 rows on the 96-well plate, leaving a volume of 100 µl in each well. This was then added to the 100 µl of cells, for a final IL-TIF concentration of 100 pg/ml in all wells, and final Zcytor16-Fc4 concentrations of approximately 1, 0.5, 0.25, 0.125, 0.063, 0.31, 0.016, and 0.008 µg/ml in a total assay volume of 200 µl. CRF2-4/zcytor11-Fc4 was diluted to 8 µg/ml in the mIL-3 free/IL-TIF media on the top row of the plate, and then diluted serially 1:2 down the remaining 7 rows on the 96-well plate, leaving a volume of 100 µl in each well. This was then added to the 100 µl of cells, for a final IL-TIF concentration of 100 pg/ml in all wells, and final CRF2-4/zcytor11-Fc4 concentrations of approximately 8, 4, 2, 1, 0.05, 0.25, 0.125 and 0.063 µg/ml, in a total assay volume of 200 The assay plates were incubated at 37° C., 5% $CO_2$ for 4 days at which time Alamar Blue (Accumed, Chicago, Ill.) was added at 200 µl/well. Plates were again incubated at 37° C., 5% $CO_2$ for 16 hours. Alamar Blue gives a fluourometric readout based on number of live cells, and is thus a direct measurement of cell proliferation in comparison to a negative control. Plates were read on the Wallac Victor 2 1420 Multilabel Counter (Wallac, Turku, Finland) at wavelengths 530 (Excitation) and 590 (Emmssion). Results showed a strong dose-dependant inhibition of the proliferative effect of IL-TIF on BaF3/CRF2-4/zcytor11 cells by Zcytor16-Fc4. CRF2-4/zcytor11-Fc4 showed a much weaker inhibition of IL-TIF. IL-TIF alone stimulated the cells 13-fold over background. Zcytor16 completely inhibited that proliferation at concentrations from 0.025-1 µg/ml, and partially inhibited proliferation at all the remaining concentrations down to 8 ng/ml. CRF2-4/zcytor11-Fc4 was only able to completely inhibit proliferation at the highest concentration of 8 µg/ml, it partially inhibited proliferation at 0.125-4 µg/ml, and inhibition was barely detectable at the lowest concentration of 63 ng/ml.

Example 29

Zcytor16 Decreases IL-6 and SAA Levels in Mouse Collagen Induced Arthritis (CIA) Model A. Mouse Collagen Induced Arthritis (CIA) Model Ten week old male DBA/1J mice (Jackson Labs) were divided into 3 groups of 13 mice/group. On day-21, animals were given a subcutaneous injection of 50-100 µl of 1 mg/ml chick Type II collagen formulated in Complete Freund's Adjuvant (prepared by Chondrex, Redmond, Wash.), and three weeks later on Day 0 they were given a 100 µl (25 µg) injection of LPS from E. coli 0111:B4, prepared as 250 µg/ml from a lyophilized aliquot (Sigma, St. Louis, Mo.). Zcytor16 was administered as an intraperitoneal injection 3 times a week for 4 weeks, from Day 0 to Day 25. The first two groups received either 100 or 10 µg of zcytor16 per animal per dose, and the third group received the vehicle control, PBS (Life Technologies, Rockville, Md.). Animals began to show symptoms of arthritis following the LPS injection, with most animals developing inflammation within 2-3 weeks. The extent of disease was evaluated in each paw by using a caliper to measure paw thickness, and by assigning a clinical score (0-3) to each paw: 0=Normal, 0.5=Toe(s) inflamed, 1=Mild paw inflammation, 2=Moderate paw inflammation, and 3=Severe paw inflammation as detailed below.

Monitoring Disease:

Animals can begin to show signs of paw inflammation soon after the second collagen injection, and some animals may even begin to have signs of toe inflammation prior to the second collagen injection. Most animals develop arthritis within 2-3 weeks of the boost injection, but some may require a longer period of time. Incidence of disease in this model is typically 95-100%, and 0-2 non-responders (determined after 6 weeks of observation) are typically seen in a study using 40 animals. Note that as inflammation begins, a common transient occurrence of variable low-grade paw or toe inflammation can occur. For this reason, an animal is not considered to have established disease until marked, persistent paw swelling has developed.

All animals were observed daily to assess the status of the disease in their paws, which was done by assigning a qualitative clinical score to each of the paws. Every day, each animal has its 4 paws scored according to its state of clinical disease. To determine the clinical score, the paw can be thought of as having 3 zones, the toes, the paw itself (manus or pes), and the wrist or ankle joint. The extent and severity of the inflammation relative to these zones was noted including observation all the toes for any joint swelling, torn nails, or redness, notation of any evidence of edema or redness in any of the paws, and notation any loss of fine anatomic demarcation of tendons or bones, and evaluation the wrist or ankle for any edema or redness, and notation if the inflammation extends proximally up the leg. A paw a score of 1, 2, or 3 was based first on the overall impression of severity, and second on how many zones were involved. The scale used for clinical scoring is shown below.

Clinical Score:

0=Normal 0.5=One or more toes involved, but only the toes are inflamed

1=mild inflammation involving the paw (1 zone), and may include a toe or toes

2=moderate inflammation in the paw & may include some of the toes and/or the wrist/ankle (2 zones)

3=severe inflammation in the paw, wrist/ankle, and some or all of the toes (3 zones)

Established disease is defined as a qualitative score of paw inflammation ranking 2 or more, that persists overnight (two days in a row). Once established disease is present, the date is recorded and designated as that animal's first day with "established disease".

Blood was collected throughout the experiment to monitor serum levels of anti-collagen antibodies. Animals were euthanized on Day 21, and blood was collected for serum and for CBC's. From each animal, one affected paw was collected in 10% NBF for histology and one was frozen in liquid nitrogen and stored at ~80° C. for mRNA analysis. Also, ½ spleen, ½ thymus, ½ mesenteric lymph node, one liver lobe and the left kidney were collected in RNAlater for RNA analysis, and ½ spleen, ½ thymus, ½ mesenteric lymph node, the remaining liver, and the right kidney were collected in 10% NBF for histology. Serum was collected and frozen at −80° C. for immunoglobulin and cytokine assays.

No statistically significant differences were found between the groups when the paw scores and measurements data were analyzed, although there was a suggestion that one treatment group receiving zcytor16 may have had a delay in the onset and progression of paw inflammation. There were no significant differences between the groups for changes in body weight, CBC parameters, or anti-collagen antibody levels. These early results indicate that zcytor16 does not adversely effect body weight, red or white blood cells, or antibody production, but may be able to reduce inflammation. Further investigations into dosing, mechanism of action, and efficacy are under way.

B. Anti-Collagen ELISA Data in Mouse CIA Model

Serum samples were collected on days 0, 7, 14, 21 and 28 relative to date of LPS challenge (day 0) from the murine model of collagen induced arthritis (Example 29A above). The serum samples were screened by ELISA for anti-collagen antibody titers. There were no statistically significant effects of zcytor16 treatment in 100 μg or 10 μg treatment groups on levels of anti-collagen antibodies compared with PBS controls. Below is a description of anti-collagen ELISA methods and materials.

Reagents used for anti-collagen ELISAs were Maxisorp 96-well microtiter plates (NUNC, Rochester, N.Y.), chick type-II collagen (Chondrex, Redmond, Wash.), Super Block (Pierce, Rockford, Ill.), horseradish peroxidase (HRP)-conjugated goat anti-mouse IgG+A+M (H+ L) (Zymed, South San Francisco, Calif.) and o-phenylenediamine dihydrochloride substrate (Pierce, Rockford, Ill.). Buffers used in all assays were ELISA B diluent buffer (PBS+0.1% BSA+0.05% Tween (Sigma, St. Louis, Mo.)), ELISA C wash buffer (PBS+0.05% Tween) and NovoD developing buffer (0.063M sodium citrate, 0.037M citric acid), $H_2O_2$ (Sigma) and 1N $H_2SO_4$ (VWR, Tukwilla, Wash.).

Approximately 100 μL of peripheral blood was collected by retro-orbital bleed into serum separator tubes (Becton Dickinson). Serum was collected by centrifugation (2-3 min, 16,000×g, 4-6° C.) and stored at −20° C. until analyzed. To determine anti-collagen Ig antibody levels, NUNC plates were coated with 10 μg/mL chick type-II collagen (Chondrex, Redmond Wash.) and incubated overnight at 4° C. Plates were washed with ELISA C, blocked (5 minutes, room temperature) with Super Block (Pierce, Rockford, Ill.), and washed with ELISA C. Diluted serum samples (diluted in ELISA B 5-fold from 1:5000 to 1:625,000) were added to ELISA plates in triplicate and the plates were incubated overnight at 4° C. After incubation, the plates were washed with ELISA C, and peroxidase-labeled goat anti-mouse Ig Fc (Zymed, 1:2000 in ELISA B) was added. The plates were incubated (room temperature, 90 minutes), rinsed again using ELISA C, and HRP activity was developed using o-phenylenediamine dihydrochloride substrate (10 mL NovoD+1 tablet OPD+10 μL $H_2O_2$, Pierce). The reaction was stopped with 1N $H_2SO_4$. Relative optical density measurements of serum samples at 1:25,000 dilution were taken at 490 nm using a Spectra MAX 190, and data were analyzed using SoftMax Pro software (Molecular Devices Corporation, Palo Alto, Calif.).

C. IL-6 and SAA Analysis in Mouse CIA Model

Day 0 serum samples were harvested from CIA mice (Example 29A above) 4 hr post administration of 25 μg LPS intraperitoneally. Samples were screened for IL-6 and serum amyloid A (SAA) concentrations by commercial ELISA kits purchased for Biosource International (Camarillo, Calif.) as per manufacturer's instructions.

The IL-6 levels were 9651+/−1563 pg/ml, 10,865+/−1478 pg/ml and 15,006+/−2,099 pg/ml in the mice groups subjected to 100 μg zcytor16, 10 μg zcytor16 and PBS control, respectively. The IL-6 concentration in the group of CIA mice exposed to the 100 μg dose of zcytor16 was significantly lower compared to PBS control mice with p=0351. Statistical significance was calculated using Fisher's PLSD with a significance level of 5% (ABACUS Concepts, INC, Berkeley, Calif.).

In addition, SAA concentrations were 381+/−40 μg/ml, 348+/−37 μg/ml and 490+/−50 μg/ml in the mice groups subjected to 100 μg zcytor16, 10 μg zcytor16 and PBS control groups, respectively. The SAA concentration in the group of CIA mice exposed to the 10 μg dose of zcytor16 was significantly lower compared with PBS control mice with p=0.0257. Statistical significance was calculated using Fisher's PLSD with a significance level of 5% (ABACUS Concepts, INC, Berkeley, Calif.).

Example 30

Expression of IL-TIF Receptor, Zcytor11, in the DSS Mouse Model

Quantitative RT-PCR was performed to measure expression levels of mouse zcytor11 in the colons of mice with DSS-induced IBD (Example 25). RNA was isolated from normal mouse colon and from the distal colons of DSS-treated mice from treatment days 2, 7 and 10. RT-PCR was performed using Applied Biosystems 7700 TaqMan instrument and protocols. Briefly, "Primer Express" software was used to designed primers against the mouse zcytor11 sequence (ZC39776 (SEQ ID NO:54) and ZC39777 (SEQ ID NO:55)) and a FAM/TAMRA labeled TaqMan probe (ZC38752 (SEQ ID NO:56)) according to Applied Biosystems guidelines. 25 ng of RNA was added to each reaction, along with PE/Applied Biosystems TaqMan EZ RT-PCR Core Reagents and the above mentioned primers and probe. RT-PCR reactions were run in duplicate under the following conditions: 50° C. for 2 minutes, 60° C. for 30 minutes, 95° C. for 5 minutes, 40 cycles of 94° C. for 20 seconds and 60° C. for 1 minute. Expression values were compared to a standard curve of known numbers of molecules of a synthetic mouse zcytor11 RNA transcript, and expression is reported as absolute number of molecules of mouse zcytor11 per reaction. Preliminary data suggests that mouse zcytor11 expression may be slightly down-regulated in the distal colons of day 7 and day 10 mice with DSS-induced IBD when compared to expression levels in normal mouse colon.

Example 31

IL-TIF and Proinflammatory Iindicators in Mild Endotoxemia Model: LPS-Induced Endotoxemia Mouse Model A. LPS-Induced Endotoxemia Mouse Model: Assessment Proinflammatory Cytokines and Body Temperature in the LPS-Induced Endotoxemia Mouse Model An in vivo experiment was designed to examine the effect of zcytor16 in a mouse LPS model of mild endotoxemia. To initially assess the model, we measured proinflammatory cytokines and body temperature to collect reference data for the model.

Briefly, six month Balb/c (CRL) female mice were injected with 25 μg LPS (Sigma) in sterile PBS intraperitoneally (IP). Serum samples were collected at 0, 1, 4, 8, 16, 24, 48 and 72 hr from groups of 8 mice for each time point. Serum samples were assayed for inflammatory cytokine levels. IL-1b, IL-6, TNFa, IL-10 and serum amyloid A protein (SAA) levels were measured using commercial ELISA kits purchased from Biosource International (Camarillo, Calif.).

TNFa levels peaked to 4000 pg/ml and IL-10 levels were 341 pg/ml at 1 hr post LPS injection. At 4 hr post LPS injection, IL-6, IL-1b and IL-10 were 6,100 pg/ml, 299 pg/ml and 229 pg/ml, respectively. The SAA levels in serum were 0.405 mg/ml by 4 hr post LPS injection. SAA concentrations in serum continued to increase to 3.9 mg/ml by 24 hr post LPS, however SAA levels greater than 1 to 2 mg/ml in serum are difficult to measure accurately or reproducibly with the existing ELISA kit due to interactions between SAA and other serum components. These results indicated that proinflammatory cytokines, in addition to IL-TIF (Example 31B), were indeed produced in this model. Thus the following criteria were established as biological markers for the LPS model of mild endotoxemia: TNFa serum levels 1 hr post LPS, IL-6 serum levels 4 hr post LPS and SAA serum levels 4 and 8 hr post LPS.

Body temperatures in a separate group of animals were monitored by surgically implanted telemetry devices over the course of the 72 hr experiment. Body temperatures in mice dropped maximally by 2° C. from 37.07° C. to 34.98° C. 30 minutes after LPS injection.

Injection of 100 ug zcytor16-Fc fusion protein 30 minutes prior to the LPS injection significantly reduced about 50% of the SAA induction at 4 hr and 8 hr time point, while 10 ug zcytor16-Fc did not have significant effect. There is no significant change to the TNF-alpha and IL-6 level. Zcytor16-Fc injection reduced neutrophil count in circulation at 1 hr time point. It showed the administration of zcytor16-Fc can neutralize zcyto18 activity in terms of SAA induction.

B. Detection of Il-Tif Activity in Mouse Serum from Lps-Induced Endotoxemia Mouse Model Using BaF3/CRF2-4/Zcytor11 Cells in an Alamar Blue Proliferation Assay BaF3/CRF2-4/zcytor11 cells, described herein, were spun down and washed in PBS 2 times to ensure the removal of the mIL-3, and then spun a third time and re-suspended in the complete media (RPMI 1640, 10% FBS, 1% GlutaMAX, 1% Sodium Pyruvate), but without mIL-3 (hereinafter referred to as "mIL-3 free media"). Cells were then counted in a hemocytometer. Cells were plated in a 96-well format at 5000 cells per well in a volume of 100 μl per well using the mIL-3 free media.

Serum from the LPS-induced endotoxemia mice from the experiment described in Example 31A above, was diluted to 2% in mIL-3 free media on the top row of the plate and then diluted serially 1:2 down the remaining 7 rows on the 96-well plate, leaving a volume of 100 μl in each well. This was then added to the 100 μl of cells, for final serum concentrations of 1%, 0.5%, 0.25%, 0.125%, 0.063%, 0.031%, 0.016%, and 0.018% in a total assay volume of 200 μl. The assay plates were incubated at 37° C., 5% $CO_2$ for 4 days at which time Alamar Blue (Accumed, Chicago, Ill.) was added at 20 μl/well. Plates were again incubated at 37° C., 5% $CO_2$ for 16 hours. Alamar Blue gives a fluourometric readout based on number of live cells, and is thus a direct measurement of cell proliferation in comparison to a negative control. Plates were read on the Wallac Victor 2 1420 Multilabel Counter (Wallac, Turku, Finland) at wavelengths 530 (Excitation) and 590 (Emmssion).

Results showed no significant proliferation above background levels in the 0 hour, 1 hour, 8 hour, and 16 hour time points. Serum samples from the 4 hour time point showed 4-fold to greater than 10-fold increases in proliferation above background, indicating the presence of IL-TIF in those samples.

C. LPS-Induced Endotoxemia Mouse Model: Experiment to Assess Effects of Zcytor16

The ability of zcytor16 treatment to effect proinflammatory indicators induced with a single 25 μg LPS dose IP in mice was tested. All samples were analyzed for SAA, IL-TIF and circulating neutrophil counts. Subsets from each group were analyzed for particular cytokine levels (1 hour samples were screened for TNF alpha, 4 hour samples were analyzed for IL-6) Animals were sacrificed at indicated time points in Table 17 below and whole blood and serum were collected and aliquoted for analysis.

72 B1/6 female mice (CRL) were given a single IP dose of zcytor16 as described in Table 17, below. Control mice were C57B1/6 (CRL).

30 minutes later, they received another IP injection of 25 μg LPS (Sigma) in 100 μl, to initiate an endotoxemia cascade. Mice in each group were sacrificed at corresponding time points as indicated in Table 17, 50 μl whole blood were collected to measure total numbers of circulating neutrophils and the rest were spun for serum and aliquoted for various assays described herein.

TABLE 17

| Group | No | Treatment | LPS | Sacrifice | Samples |
|---|---|---|---|---|---|
| | 8 | 100 μg zcytor16 IP | 25 μg IP 30 min post tx | 1 hour | Serum aliquots Blood for CBC |
| | 8 | 10 μg zcytor16 IP | 25 μg IP 30 min post tx | 1 hour | Serum aliquots Blood for CBC |
| | 8 | 200 μl PBS IP | 25 μg IP 30 min post tx | 1 hour | Serum aliquots Blood for CBC |
| | 8 | 100 μg zcytor16 IP | 25 ug IP 30 min post tx | 4 hours | Serum aliquots Blood for CBC |
| | 8 | 10 μg zcytor16 IP | 25 μg IP 30 min post tx | 4 hours | Serum aliquots Blood for CBC |
| F | 8 | 200 μl PBS IP | 25 μg IP 30 min post tx | 4 hours | Serum aliquots Blood for CBC |
| G | 8 | 100 μg zcytor16 IP | 25 μg IP 30 min post tx | 8 hours | Serum aliquots Blood for CBC |
| H | 8 | 10 μg zcytor16 IP | 25 μg IP 30 min post tx | 8 hours | Serum aliquots Blood for CBC |
| J | 8 | 200 μl PBS IP | 25 μg IP 30 min post tx | 8 hours | Serum aliquots Blood for CBC |
| K | 5 | controls | none | Pre LPS | Serum aliquots Blood for CBC |

D. Zcytor16/Fc4 Neutralizes SAA Induction In Vivo: SAA ELISA Showing SAA Expression Induced by LPS in LPS-Induced Endotoxemia Mouse Model is Inhibited by zcytor16-Fc4 Injection:

To assess whether zcytor16 could inhibit the SAA induction in the LPS-induced endotoxemia mouse model, mice were injected with Zcytor16, 30 minutes prior to LPS injection, as shown in Table 17 in Example 31C above.

An ELISA to determine SAA levels in the 4 hour and 8 hour samples was performed using the Mouse SAA Immunoassay Kit (BioSource International, California) following the manufacturer's directions. At the 4 hour time point, mice treated with 100 μg or 10 μg of Zcytor16 showed a dose-dependant, statistically significant reduction in SAA levels relative to the PBS injected mice. At the 8 hour time point, mice treated with 100m, continued to show a statistically significant reduction in SAA levels relative to the PBS injected mice. This indicates that the presence of Zcytor16 is able to inhibit the induction of SAA by LPS in vivo.

Example 32

Baculovirus Expression of FlagTBXzCytor16

An expression vector, pzBV37L:egtNF(tbx)sCytor16, was designed and prepared to express FlagTBXzCytor16 polypeptides in insect cells.

Expression of FlagTBXzCytor16

An expression vector, pzBV37L:egtNF(tbx)sCytor16 was designed to express zCytor16 polypeptide with an upstream 6 amino acid thrombin cleavage site and an n-terminal Flag epitope tag upstream of the enzyme cleavage site. This construct can be used to express a flag tagged zCytor16 with an enzyme processing site directly upstream of the soluble receptor sequence, after the signal peptide has been cleaved off.

A. Construction of pzBV37LegtNF(tbx)sCytor16

A 698 bp, FlagTBXzCytor16 sequence fragment containing Bspe1 and Xba1 restriction sites on the 5' and 3' ends, respectively, was generated by two rounds of PCR amplification from a zCytor16 cDNA containing template. Primers ZC40,940 (SEQ ID NO:57) and ZC40,943 (SEQ ID NO:58) were used in the first round and primers ZC40942 (SEQ ID NO:59) and ZC40,943 (SEQ ID NO:58) in the second round. For the first round of PCR, reaction conditions were as follows: utilized the Expand High Fidelity PCR System (Boerhinger Mannheim) for a 100 ul vol. reaction. 1 cycle at 94° C. for 2 minutes; 35 cycles of 94° C. for 15 seconds, 50° C. for 30 seconds, and 72° C. for 60 seconds; 1 cycle at 72° C. for 5 min; followed by 4° C. soak. 5 ul of the first round reaction mix was visualized by gel electrophoresis (1% NuSieve agarose). Once the presence of a correct size PCR product was confirmed, the second round of PCR was set up using 1 ul of the first round reaction as template. Conditions of the second reaction were the same as the first. 5 ul of the second round PCR was visualized by gel electrophoresis (1% NuSieve agarose). The remainder of the reaction mix was purified via Qiagen PCR purification kit as per manufacturers instructions and eluted in 30 ul water. The cDNA was digested in a 35 ul vol. using Bspe1 and Xba1 (New England Biolabs, Beverly, Mass.) in appropriate buffer conditions at 37 degrees C. The digested PCR product band was run through a 1% agarose TAE gel, excised and extracted using a QIAquick™ Gel Extraction Kit (Qiagen, Cat. No. 28704) and eluted in 30 ul of water. The digested FlagTBXzCytor16 PCR was ligated into the MCS of vector pZBV37L at the Bspe1 and Xba1 sites. The pZBV37L vector is a modification of the pFastBac1™ (Life Technologies) expression vector, where the polyhedron promoter has been removed and replaced with the late activating Basic Protein Promoter and the EGT leader signal sequence upstream of the MCS. 5 ul of the restriction enzyme digested FlagTBXzCytor16 PCR fragment and apx. 50 ng of the corresponding pZBV37L vector were ligated overnight at 16° C. in a 20 ul vol. in appropriate buffer conditions. 5 ul of the ligation mix was transformed into 50 ul of ElectoMAX™ DH12s™ cells (Life Technologies, Cat. No. 18312-017) by electroporation at 400 Ohms, 2V and 25 µF in a 2 mm gap electroporation cuvette (BTX, Model No. 620). The transformed cells were diluted in 350 µl of SOC media (2% Bacto Tryptone, 0.5% Bacto Yeast Extract, 10 ml 1M NaCl, 1.5 mM KCl, 10 mM $MgCl_2$, 10 mM $MgSO_4$ and 20 mM glucose) outgrown for 1 hr at 37 degrees C. and 50 µl of the dilution were plated onto LB plates containing 100 µg/ml ampicillin. Clones were analyzed by PCR and positive clones were selected, plated and submitted for sequencing. Once proper sequence was confirmed, 25 ngs of positive clone DNA was transformed into 100 µl DH10Bac™ Max Efficiency® competent cells (GIBCO-BRL Cat. No. 10361-012) by heat shock for 45 seconds in a 42° C. heat block. The transformed DH10Bac™ cells were diluted in 900 µl SOC media (2% Bacto Tryptone, 0.5% Bacto Yeast Extract, 10 ml 1M NaCl, 1.5 mM KCl, 10 mM $MgCl_2$, 10 mM $MgSO_4$ and 20 mM glucose) outgrown for 1 hr at 37 degrees C. and 100 µl were plated onto Luria Agar plates containing 50 µg/ml kanamycin, 7 µg/ml gentamicin, 10 µg/ml tetracycline, 40 µg/mL IPTG and 200 µg/mL Bluo Gal. The plates were incubated for 48 hours at 37° C. A color selection was used to identify those cells having transposed viral DNA (referred to as a "bacmid"). Those colonies, which were white in color, were picked for analysis. Colonies were analyzed by PCR and positive colonies (containing desired bacmid) were selected for outgrow. Clones were screened for the correct M.W. insert by amplifying DNA using primers to the transposable element in the bacmid via PCR using primers ZC447 (SEQ ID NO:34) and ZC976 (SEQ ID NO:7). The PCR reaction conditions were as follows: 1 cycle at 94° C. for 2 minutes; 25 cycles of 94° C. for 10 seconds, 50° C. for 30 seconds, and 72° C. for 120 seconds; 1 cycle at 72° C. for 5 min; followed by 4° C. soak. The PCR product was run on a 1% agarose gel to check the insert size. Those having the correct size insert were outgrown and the bacmid DNA isolated and purified. This bacmid DNA was used to transfect *Spodoptera Frugiperda* (Sf9) cells.

B. Transfection

Sf9 cells were seeded at $1 \times 10^6$ cells per well in a 6-well plate and allowed to attach for 1 hour at 27° C. Approximately five µg. of bacmid DNA were diluted with 100 µl Sf-900 II SFM (Life Technologies). Twenty µl of Lipofectamine™ Reagent (Life Technologies, Cat. No. 18324-012) were diluted with 100 µSf-900 II SFM. The bacmid DNA and lipid solutions were gently mixed and incubated 45 minutes at room temperature. Eight hundred microliters of Sf-900 II SFM was added to the lipid-DNA mixture. The media was aspirated from the well and the 1 ml of DNA-lipid mix added to the cells. The cells were incubated at 27° C. overnight. The DNA-lipid mix was aspirated and 2 ml of Sf-900 II media was added to each plate. The plates were incubated at 27° C., 90% humidity, for approximately 7 days after which the virus was harvested.

C. Amplification

Sf9 cells were seeded at $1 \times 10^6$ cells per well in a 6-well plate in 2 mls SF-900II. 500 µl of virus from the transfection plate were placed in the well and the plate was incubated at 27° C., 90% humidity, for 96 hours after which the virus was harvested (primary amplification).

A second round of amplification proceeded as follows: Sf9 cells were seeded at $1 \times 10^6$ cells per well in a 6-well plate in 2 mls SF-900II. 100 µl of virus from the primary amplification plate were placed in the well and the plate was incubated at 27° C., 90% humidity, for 144 hours after which the virus was harvested (Secondary amplification).

An additional round of amplification was performed ($3^{rd}$ round amp.) Sf9 cells were grown in 50 ml Sf-900 II SFM in a 250 ml shake flask to an approximate density of $1 \times 10^6$ cells/ml. They were then infected with 1 ml of the viral stock from the above plate and incubated at 27° C. for 4 days after which time the virus was harvested.

This viral stock was titered by a growth inhibition curve and the titer culture that indicated a MOI of 1 was allowed to proceed for a total of 48 hrs. The supernatant was analyzed via Western blot using a primary monoclonal antibody specific for the n-terminal Flag epitope and a HRP conjugated Gt anti Mu secondary antibody. Results indicated a band of apx. 30 kDa. Supernatant was also provided for activity analysis.

A large viral stock was then generated by the following method: Sf9 cells were grown in 1L Sf-900 II SFM in a 2800 ml shake flask to an approximate density of $1 \times 10^6$ cells/ml. They were then infected with 5 mls of the viral stock from the $3^{rd}$ round amp. and incubated at 27° C. for 96 hrs after which time the virus was harvested.

Larger scale infections were completed to provide material for downstream purification.

Example 33

In Vivo Effects of IL-TIF Polypeptide on Skin

A. IL-TIF-Induced Acanthosis

Mice (female, C3H/HEJ, 8 weeks old; Jackson Labs, Bar Harbor, Me.) were divided into three groups of six animals and one group of 4. Human BHK-produced IL-TIF was administered by constant infusion via mini-osmotic pumps, resulting in local and steady state serum concentrations proportional to the concentration of the IL-TIF contained in the pump. Alzet mini-osmotic pumps (model 2002; Alza corporation Palo Alto, Calif.) were loaded under sterile conditions with IL-TIF protein (A601F, 0.22 mL) diluted in phosphate buffered saline (pH 7.0) to a concentration within the pump of 2 mg/mL for group 1 mice, 0.2 mg/mL for group 2 mice, 0.02 mg/mL for group 3 mice, or 0 mg/mL (diluent only) for group 4 mice. Pumps were implanted subcutaneously in mice through a 1 cm incision in the dorsal skin, and the skin was closed with sterile wound closures. These pumps are designed to deliver their contents at a rate of 0.5 µl per hour over a period of 14 days. Using this nominal rate of infusion, dose levels were calculated to be 24 µg/day, 2.4 µg/day, 0.24 µg/day and 0 µg/day for groups 1-4, respectively.

At the end of the 14-day period, the mice were euthanized and an approximately 1 cm square sample of skin surrounding the pump area was collected from each mouse. The skin was fixed in 10% neutral buffered formalin. Formalin fixed samples of skin were embedded in paraffin, routinely processed, sectioned at 5 um and stained with hematoxylin and eosin. The tissues were microscopically examined in blinded fashion by an ACVP board certified veterinary pathologist. Histological changes were noted, and the severity of acanthosis (i.e. epidermal thickening) scored in a subjective manner using the following scoring system: O-normal, 1-minimal acanthosis, 2-mild acanthosis, 3-moderate acanthosis and 4-severe acanthosis. In addition, the skin of selected groups was imaged with a CoolSnap digital camera (Roper Scientific, Inc., San Diego, Calif.) and epidermal thickness measured using histomorphometry software (Scion Image for Windows, v. 4.02, Scion Corp., Frederick, Md.).

Administration of IL-TIF at 2.4, and 24 µg/day resulted in epidermal thickening as shown by the average acanthosis score (see s) consistently greater than observed in control group skin. Moreover, IL-TIF treated animals also had mononuclear cell infiltrates in the epidermis. These infiltrates were not observed in the vehicle treated controls.

Acanthosis scores of epidermal thickness and measurements of skin thickness (in generic units of pixels) by groups are shown in Table 18 below, as follows:

TABLE 18

| Group # | n= | Pump | Average Acanthosis | Measured Thickness |
|---|---|---|---|---|
| 1 | 6 | 24 µg IL-TIF/day | 3.0 | ND |
| 2 | 6 | 2.4 µg IL-TIF/day | 2.4 | 67.5 |
| 3 | 6 | 0.24 µg IL-TIF/day | 2.2 | ND |
| 4 | 4 | PBS infusion | 1.8 | 45.6 |

B. Effect of Zcytor16 on IL-TIF-Induced Acanthosis

Mice (female, C3H/HEJ, 8 weeks old; Jackson Labs, Bar Harbor, Me.) were divided into eight groups of eight animals each. IL-TIF was administered by constant infusion via mini-osmotic pumps, as described in example 32a. Alzet mini-osmotic pumps (model 2001; Alza corporation Palo Alto, Calif.) were loaded under sterile conditions with IL-TIF protein (A#601F, 0.22 mL) diluted in phosphate buffered saline (pH 7.0) to a concentration within the pump of 0.22 mg/mL for group 1-2 mice, 0.45 mg/mL for group 3-4 mice, 0.9 mg/mL for group 5-6 mice, or 0 mg/mL (diluent only) for group 7-8 mice. These pumps are designed to deliver their contents at a rate of 0.5 µl per hour over a period of 14 days. Using this nominal rate of infusion, dose levels were calculated to be 10 µg/day in groups 1-2, 5 µg/day on groups 3-4, 2.5 µg/day in groups 5-6 and 0 µg/day for groups 7-8. For each pair of groups at a given dose level of IL-TIF, one of the groups was injected three times (days 1, 3, and 5) with 0.1 mg of human zcytor16 Fc protein (described herein) by the intraperitoneal route. The other group was injected in the same fashion with vehicle (PBS).

On day 8 of the study, mice were euthanized and an approximately 1 cm square sample of skin surrounding the pump area was collected from each mouse. The skin was fixed in 10% neutral buffered formalin. Formalin fixed samples of skin were embedded in paraffin, routinely processed, sectioned at 5 um and stained with hematoxylin and eosin. The tissues were microscopically examined in blinded fashion by an ACVP board certified veterinary pathologist. This study was scored in a different manner than the previous example. The number of layers in the epidermis, from stratum basalis to stratum granulosum, was determined Based on the results, the sections were scored as follows: O-normal (2-3 layers), 1-mild thickening (3-4 layers), 2-moderate thickening (4-6 layers) and 3-severe thickening (>6 layers).

Administration of IL-TIF at 2.5, 5, 10 µg/day resulted in epidermal thickening (see Table 19). Moreover, IL-TIF treated animals also had mononuclear cell infiltrates in the epidermis. These infiltrates were not observed in the vehicle treated controls. Concurrent administration of 100 µg zcytor16 (3 injections) decreased the amount of epidermal thickening in mice treated with 5 µg IL-TIF/day.

Acanthosis scores of epidermal thickness by groups are shown in Table 19, below, as follows:

TABLE 19

| Group # | n= | Pump | Injection | Average Acanthosis |
|---|---|---|---|---|
| 1 | 8 | 2.5 µg IL-TIF/day | 100 µL vehicle (3 injections) | 1.1 |
| 2 | 8 | 2.5 µg IL-TIF/day | 100 µg zcytor16 (3 injections) | 0.8 |
| 3 | 8 | 5 µg IL-TIF/day | 100 µLvehicle (3 injections) | 2.0 |
| 4 | 8 | 5 µg IL-TIF/day | 100 µg zcytor16 (3 injections) | 0.6 |

TABLE 19-continued

| Group # | n= | Pump | Injection | Average Acanthosis |
|---|---|---|---|---|
| 5 | 8 | 10 µg IL-TIF/day | 100 µL vehicle (3 injections) | 2.0 |
| 6 | 8 | 10 µg IL-TIF/day | 100 µg zcytor16 (3 injections) | 1.9 |
| 7 | 8 | Vehicle | 100 µL vehicle (3 injections) | 0.0 |
| 8 | 8 | Vehicle | 100 µg zcytor16 (3 injections) | 0.0 |

Epidermal thickening and immune infiltrates were also observed in human psoriatic skins. The skin phenotype observed in IL-TIF subcutaneous injection further indicated the potential role of IL-TIF in the pathogenesis of psoriasis. The fact that zcytor16-Fc can neutralize the IL-TIF induced skin phenotype suggests the potential use of other IL-TIF antagonists such as and anti-IL-TIF neutralizing antibody or soluble receptor for the treatment of psoriasis and other IL-TIF induced inflammatory diseases.

C. Effect of Anti-IL-TIF Antibodies on IL-TIF-Induced Acanthosis

The activity of an antibody to IL-TIF to inhibit the in vivo activity of IL-TIF is evaluated in a similar manner, using the histological endpoint of acanthosis caused by subcutaneous infusion of IL-TIF protein. In an example of this model C3H/HEJ mice are implanted with subcutaneous mini-osmotic pumps as described in examples 33(A) and 33(B) above. During the period of exposure to IL-TIF, the mice are treated by injection with the purified monoclonal antibody to IL-TIF or similarly injected with vehicle as control. At the end of the IL-TIF infusion period, skin would be sampled from the pump area for histological analysis. Similar to the zcytor16 soluble receptor IL-TIF antagonist, IL-TIF antagonist neutralizing antibodies of the present invention are expected to show reduction in epidermal thickening and immune cell infiltrates caused by IL-TIF, and hence be useful as IL-TIF antagonists as a therapeutic for psoriasis and other IL-TIF induced inflammatory disease.

Example 34

IL-TIF is Upregulated in Human Psoriatic Skin Samples

A. RNA Samples:

Normal skin samples as well as skin from psoriasis patients were obtained. The latter included involved skin from stable plaque-type psoriasis and from adjacent uninvolved skin. RNA was isolated from human skin samples using conventional methods. The integrity and quality of RNA samples was tested on the Agilent 2100 Bioanalyzer (Agilent Technologies, Waldbronn Germany).

B. Primers and Probes for Quantitative RT-PCR-

Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-TIF expression were designed using the primer design software Primer Express™ (PE Applied Biosystems, Foster City, Calif.). Primers for human IL-TIF were designed spanning an intron-exon junction to eliminate amplification of genomic DNA. The forward primer, ZC 42459 (SEQ ID NO:65) and the reverse primer, ZC 42458 (SEQ ID NO:66) were used in a PCR reaction (below) at a 800 nM concentration to synthesize a 72 bp product. The corresponding IL-TIF probe, ZC 42460 (SEQ ID NO:67) was synthesized and labeled in house at ZymoGenetics. The IL-TIF probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

C. Real-Time Quantitative RT-PCR-

Relative levels of IL-TIF mRNA were determined by analyzing total RNA samples using the TaqMan EZ RT-PCR Core Reagents Kit (PE Applied Biosystems). Runoff IL-TIF transcript was made to generate a standard curve used for quantitation. The curve consisted of 10-fold serial dilutions ranging from 1e8 to 1e3 total copies of whole message for IL-TIF with each standard curve point analyzed in triplicate. The total RNA samples from skin were also analyzed in triplicate for human IL-TIF transcript levels and for levels of hGUS as an endogenous control. In a total volume of 25 µl, each RNA sample was subjected to TaqMan EZ RT-PCR reaction (PE Applied Biosystems) containing: approximately 25 ng of total RNA in DEPC treated water (Dnase/Rnase free); appropriate primers (approximately 800 nM ZC 42459 (SEQ ID NO:65) and ZC 42458 (SEQ ID NO:66); appropriate probe (approximately 100 nM ZC 42460 (SEQ ID NO:67); 1×TaqMan EZ Buffer; 3 mM Manganese acetate; 300 µM each d-CTP, d-ATP, and d-GTP and 600 µM of d-UTP; rTth DNA Polymerase (0.1 U/µl); and AmpErase UNG (0.01 U/µl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-TIF RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize the IL-TIF levels. Data are shown in Table 20 below.

TABLE 20

| Skin Sample | IL-TIF |
|---|---|
| Normal | 0 |
| Uninvolved | 0 |
| Involved | 1149 |

IL-TIF mRNA was undetectable in skin samples from normal patients or from uninvolved areas. In contrast, there was dramatic upregulation for IL-TIF message in involved skin from psoriasis patients. These data support a strong disease association for IL-TIF to human psoriasis.

Over expression of IL-TIF was shown in human psoriatic lesions, suggesting that IL-TIF is involved in human psoriasis. Moreover, as described herein, over expression of IL-TIF in transgenic mice showed epidermal thickening and immune cell involvement indicative of a psoriatic phenotype, and in addition injection of IL-TIF into normal mice showed epidermal thickening and immune cell involvement indicative of a psoriatic phenotype which was ablated by the soluble receptor antagonist zcytor16. Such in vivo data further suggests that the pro-inflammatory IL-TIF is involved in psoriasis. As such, antagonists to IL-TIF activity, such as the anti-human-IL-TIF monoclonal antibodies of the present invention, as well as soluble receptors and antibodies thereto, are useful in therapeutic treatment of inflammatory diseases, particularly as antagonists to IL-TIF in the treatment of psoriasis. Moreover, antagonists to IL-TIF activity, such as the anti-human-IL-TIF monoclonal antibodies of the present invention, as well as soluble receptors and antibodies thereto, are useful in therapeutic treatment of other inflammatory diseases for example as antagonists to IL-TIF in the treatment of atopic dermatitis, IBD, colitis, Endotoxemia, arthritis, rheumatoid arthritis, and psoriatic arthritis, adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

Example 35

Human IL-TIF Polyclonal Antibodies

Anti IL-TIF Polyclonal antibodies were prepared by immunizing 2 female New Zealand white rabbits with the purified mature recombinant human IL-TIF polypeptide (amino acid residues 22 (Ala) to 167 (Ile) of SEQ ID NO:3), produced from BHK cells (IL-TIF-BHK). The rabbits were each given an initial intraperitoneal (ip) injection of 200 µg of purified protein in Complete Freund's Adjuvant followed by booster IP injections of 100 µg peptide in Incomplete Freund's Adjuvant every three weeks. Seven to ten days after the administration of the second booster injection (3 total injections), the animals were bled and the serum was collected. The animals were then boosted and bled every three weeks.

The human IL-TIF-specific polyclonal antibodies were affinity purified from the immune rabbit serum using a CNBr-SEPHAROSE 4B protein column (Pharmacia LKB) that was prepared using 10 mg of the specific antigen purified recombinant protein human IL-TIF-BHK per gram of CNBr-SEPHAROSE, followed by 20× dialysis in PBS overnight. Human IL-TIF-specific antibodies were characterized by ELISA using 500 ng/ml of the purified recombinant protein human IL-TIF-BHK as antibody target. The lower limit of detection (LLD) of the rabbit anti-human IL-TIF affinity purified antibody is 280 pg/ml on its specific purified recombinant antigen human IL-TIF-BHK.

The human IL-TIF-specific polyclonal antibodies were characterized further for their ability to block the cell-proliferative activity ("neutralization assay") of purified recombinant human IL-TIF-BHK on BaF3/CRF2-4/zcytor11 cells (Example 22). A 50× molar excess of the human IL-TIF-specific polyclonal antibodies was sufficient to inhibit cell proliferation.

Example 36

Anti-Human IL-TIF Monoclonal Antibodies

Monoclonal antibodies were prepared by immunizing 4 female Sprague-Dawley Rats (Charles River Laboratories, Wilmington, Mass.), with the purified mature recombinant human IL-TIF polypeptide (amino acid residues 22 (Ala) to 167 (Ile) of SEQ ID NO:3), produced from BHK cells (IL-TIF-BHK). The rats were each given an initial intraperitoneal (IP) injection of 100 µg of the purified human recombinant IL-TIF protein in Complete Freund's Adjuvant (Pierce, Rockford, Ill.) followed by booster IP injections of 50 µg of the purified recombinant protein in Incomplete Freund's Adjuvant every two weeks. Seven to ten days after the administration of the third booster injection, the animals were bled and the serum was collected.

The human IL-TIF-specific rat sera samples were characterized by ELISA using 500 ng/ml biotinylated human IL-TIF-BHK and 500 ng/ml biotinylated mouse IL-TIF, biotinylated muIL-TIF-$E.\ coli$ (R+D Systems, Minneapolis, Minn.) antibody targets. Three rat serum samples had titer to the specific antibody target biotinylated human IL-TIF-BHK at a dilution of 1:1E5 and to the specific antibody target biotinylated muIL-TIF-$E.\ coli$ at a dilution of 1:1E4.

Splenocytes and lymphatic node cells were harvested from 2 high-titer rats and fused to SP2/0 (mouse) myeloma cells using PEG 1500 in two separate fusion procedures (4:1 fusion ratio, splenocytes to myeloma cells, "Antibodies A Laboratory Manual, E. Harlow and D. Lane, Cold Spring Harbor Press). Following 10 days growth post-fusion, specific antibody-producing hybridoma pools were identified by ELISA using the biotinylated recombinant protein human IL-TIF-BHK and the biotinylated recombinant protein muIL-TIF-$E.\ coli$ as separate antibody targets. Hybridoma pools positive in both ELISA protocols were analyzed further for their ability to block the cell-proliferative activity ("neutralization assay") of purified recombinant muIL-TIF-$E.\ coli$ on BaF3/CRF2-4/zcytor11 cells (Example 22).

Hybridoma pools yielding positive results by ELISA only or ELISA and the "neutralization assay" were cloned at least two times by limiting dilution.

Monoclonal antibodies purified from tissue culture media were characterized for their utility in an ELISA for the quantitative determination of recombinant and native human IL-TIF in mouse and human serum samples. The two antibodies selected resulted in a quantitative assay with a lower limit of detection of approximately 1 ng/ml recombinant huIL-TIF-$E.\ coli$ in 100% human serum.

Monoclonal antibodies purified from tissue culture media were characterized for their ability to block the cell-proliferative activity ("neutralization assay") of purified recombinant huIL-TIF-$E.coli$ or muIL-TIF-$E.coli$ on BaF3/CRF2-4/zcytor11 cells (Example 22). Six "neutralizing" monoclonal antibodies were identified in this manner. Hybridomas expressing the neutralizing monoclonal antibodies to human IL-TIF described above were deposited and received Mar. 5, 2003, with the American Type Tissue Culture Collection (ATCC; 10801 University Boulevard, Manassas, Va. 20110-2209) patent depository as original deposits under the Budapest Treaty and were given the following ATCC Accession Nos.: 266.16.1.4.4.1 (ATCC PTA-5035); 266.5.1.2.2.3 (ATCC PTA-5033); 267.17.1.1.4.1 (ATCC PTA-5038); 267.4.1.1.4.1 (ATCC PTA-5037); 266.12.6.1.3.2.1 (ATCC PTA-5034); 266.19.1.10.5.2 (ATCC PTA-5036).

Example 37

Immunohistochemical Analysis of IL-TIF Protein Expression In Vivo in Tissue Samples A. Summary Immunohistochemical (IHC) analysis of IL-TIF protein expression and localization was achieved using rat monoclonal antibody (Mab 266.19.1.10.5.2) raised against human IL-TIF-BHK (Example 36) in the following tissue samples: a Human multi-Normal Grid and Tumor Grid; Human pancreatitis, lung and renal disease samples; Human psoriasis skin samples; INC IL-TIF TG (expressed from the rat insulin promoter) and WT mouse pancreas; muIL-TIF-EuLCK TG and WT mouse skin sample; and DSS (WT and IL-TIF KO) mouse colon sample. Moreover the staining pattern of monoclonal antibody MAB 266.19.1.10.5.2 (rat anti-huIL-TIF-BHK) vs. polyclonal antibody (rabbit anti-human IL-TIF FL-BHK) (Example 35) was compared.

The rat anti-Human IL-TIF monoclonal antibodies MAb 266.16.1.4.4.1, and MAb 266.19.1.10.5.2 (Example 36) were tested were shown to stain the majority of BHK/human IL-TIF (>50%) but also some BHK/mouse IL-TIF cells (1-5%), and were used to investigate the tissue distribution and expression of IL-TIF in both human patient and animal model samples and used to compare the staining pattern with polyclonal rabbit antibody to confirm the results.

B. Materials and Methods

Formalin-fixed and paraffin-embedded cells and tissues from human sources and mouse animal models were sectioned at 5 µm. The cells included BHK cells expressing either human or mouse IL-TIF and wild type as positive control and negative control, respectively. The human tissues included a Multi-tissue control slide (NormalGrid™; Biomeda, Foster City, Calif.) with 50 sections of various normal human tissues (e.g., brain, pituitary gland, adrenal gland, breast, kidney, heart, stomach, small intestine, large intestine, fetal liver, liver, skin, pancreas, lung, tonsil, ovary, testis, prostate, uterus, placenta, thyroid and spleen); a Multi-tissue control slide (TumorGrid™; Biomeda, Foster City, Calif.) with 50 sections of various human tumors (e.g., lung adeno Ca., liver adeno Ca., kidney adeno Ca., colon adeno Ca., breast adeno Ca., thyroid adeno Ca., stomach adeno Ca., prostate adeno Ca., pancreas adeno Ca., ovary adeno Ca., lymphoma, melanoma, sarcoma ewings, sarcoma epithelioid, sarcoma MFH, sarcoma Rhabdo, carcinoid, undiff Ca., mesothelioma, teretoma and seminoma); lung carcinoma from CHTN (Cooperation Human Tissue Network, Cleveland, Ohio); normal pancreas, pancreas with chronic pancreatitis, lung with chronic perivascular inflammation, kidneys with either multifocal glomerulosclerosis, mesangioproliferative glomerulonephritis, or sclerotic glomeruli interstitial fibrosis from NDR1 (National Disease Research Interchange, Philadelphia, Pa.); and psoriatic skin samples from human. The mouse tissues included colons from inflammatory bowel disease animal model (DSS model disclosed herein, Swiss Webster female mice) and from zcyto10 WT and KO colitis animal model (DSS mice, wild type and zcyto10 knock out female mice) treated with either vehicle or 4% DSS in drinking water for 7 days; and skin samples from transgenic (TG) animal models including mIL-TIF-EuLCK TG and mIL-TIF-INS control and TG animals. One section per block/slide was stained with hematoxylin and eosin (H&E) for histologic examination and the subsequent section were immunohistochemically stained for IL-TIF protein expression and localization.

For immunohistochemistry, the cell and tissue sections were placed on ChemMate™ Capillary Gap Plus microscope slides (BioTek, Winooski, Vt.), dried at 60° C. oven for 60 minutes and dewaxed using standard conditions of 3×5 minutes in xylene, 4 minutes in 100% EtOH, 3 minutes in 100% EtOH, and 2 minutes in 95% EtOH. The tissue sections were then subjected to a 20-minute enzyme-induced epitope retrieval process at 37° C. with pepsin (NeoMarkers Fremont Calif.) followed by an avidin/biotin-blocking step done according to the manufacturers instructions (Zymed, South San Francisco, Calif.). TechMate 500™ Automated Immunostainer and Immunoperoxidase (IP) immunohistochemical protocol with avidin-biotin-complex detection system (Ventana Biotek Systems, Tucson, Ariz.) were employed for the staining The TechMate 500™ Automated Immunostainer employed the principle of capillary action and the IP protocol utilized a type of immunostaining referred to as a "sandwich" technique. The sections were preblocked with 5% normal goat serum (Vector, Burlingame Calif.) in PBS for 10 minutes followed by 1× buffer1 wash (Signet, Dedham Mass.) and then incubated with primary antibody against IL-TIF (MAB 266.19.1.10.5.2, rat anti-huIL-TIF-BHK (Example 36), PAS purified at 2.04 mg/ml) diluted at 1:800 for 30 minutes at room temperature followed by 5× buffer1 wash. The primary antibody was diluted in TechMate 500™ antibody dilution buffer (Ventana). Biotinylated goat anti-rat IgG (Vector) diluted at 1:200 plus 5% normal goat serum and 2.5% nonfat dry milk in PBS was used as the secondary-linking antibodies for 25 minutes at room temperature followed by 1× buffer1 wash and 1× Buffer2&3 wash (Signet). The tissues sections were then subjected to a 3×7 minutes 3% hydrogen peroxide (HP) blocking (Ventana) followed by 3× buffer2&3 wash Immunoperoxidase labeling was performed with a peroxides DAB kit (Ventana), incubating with avidin-biotin-complex (ABC) for 30 minutes followed by 5× buffer2&3 wash and diaminobenzidine (DAB) for 4×4 minutes followed by 2× buffer2&3 wash and 1× water wash (Signet, Cat. No. 2340). Tissues were then counter stained with methyl green (Dako, Cat.No. S1962) for 10 minutes followed by 2× buffer2&3 wash and 3× water wash. Control included non-immune primary sera using rat primary antibody isotype control (Zymed) to replace the primary antibody.

Immunostaining was observed using an Olympus BH-2 microscope and images were captured by CoolSNAP HQ digital camera (Roper Scientific, Tucson, Ariz.).

C. Results

Positive and negative control cell lines: MAB 266.19.1.10.5.2, the rat anti-huIL-TIF-BHK monoclonal antibody demonstrated positive staining on both human IL-TIF expressing BHK cells (+++) and murine IL-TIF expressing BHK cells (+), and no staining on the wild type BHK cells (−). All the positive and negative BHK cell lines stained with rat isotype negative control to replace the primary antibody showed no staining (−) which indicated that the antibody is specific to IL-TIF ligand. The antibody has cross immunoreactivity to both human and mouse IL-TIF.

Human tissues: Human multi-Normal Grid and Tumor Grid; pancreas, lung and renal disease samples; and human psoriasis skin samples were examined. These human tissues included 1). Brain, pituitary gland, adrenal gland, breast, kidney, heart, stomach, small intestine, large intestine, fetal liver, liver, skin, pancreas, lung, tonsil, ovary, uterus, testis, placenta, thyroid and spleen on the Multi-tissue control slides (NormalGrid™)/normal human tissues; 2). Lung adeno Ca., liver adeno Ca., kidney adeno Ca., thyroid adeno Ca., stomach adeno Ca., prostate adeno Ca., pancreas adeno Ca., ovary adeno Ca., lymphoma, melanoma, sarcoma ewings, sarcoma epithelioid, sarcoma MFH, sarcoma Rhabdo, carcinoid, undiff. Ca., mesothelioma, teratoma, and seminoma, on the Multi-tissue control slides (TumorGrid™)/human abnormal tissues/tumor; 3). Normal pancreas, pancreas with chronic pancreatitis, lung with chronic perivascular inflammation, lung Ca., kidney with multifocal glomerulosclerosis, kidney with mesangioproliferative glomerulonephritis, kidney with sclerotic glomeruli interstitial fibrosis from CHTN and/or NDR1; 4). Mouse tissues: INC IL-TIF TG and WT mouse pancreas were examined. Scattered cells throughout the islets in the INC IL-TIF TG pancreas demonstrated strong positive staining (+++) with Mab MAB 266.19.1.10.5.2 and WT pancreas showed no staining (−). Comparison of polyclonal and monoclonal antibodies. The anti-IL-TIF polyclonal antibody was shown to be sensitive but less specific, whereas monoclonal antibody MAB 266.19.1.10.5.2 is more specific but less sensitive. It showed positive staining on human IL-TIF expressing BHK cells (+++), on murine IL-TIF expressing BHK cells (+), in various human and mouse tissue samples (+), and in the islets of INC mIL-TIF TG mice (+++). A greater percentage of the islets of the transgenics (vs. wild-type) contained positive staining. The staining in the transgenic islets was generally distributed throughout the islet (+++) while staining in the wild-type islets was generally limited to the periphery of the islet (+). However, this antibody also showed non-specific staining on the WT BHK negative control cells (+). MAB 266.19.1.10.5.2 showed positive staining on human IL-TIF expressing BHK cells (+++), on murine IL-TIF expressing BHK cells (+), and in the islets of INC mIL-TIF TG mice (+++). The staining in the transgenic islets was generally distributed throughout the islet (+++) while the wild-type islets demonstrated negative staining (−).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A monoclonal antibody, or antigen binding fragment thereof, comprising the heavy and light chain variable regions of an antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1, (ATCC PTA-5037); and (e) the hybridoma clone 266.12.6.1.3.2.1 (ATCC PTA-5034); and (e) the hybridoma clone 266.19.1.10.5.2,(ATCC PTA-5036).

2. The antibody, or antigen binding fragment, of claim 1, wherein the antibody, or antigen binding fragment is linked to a therapeutic agent.

3. The antibody, or antigen binding fragment, of claim 2, wherein the therapeutic agent is selected from the group consisting of a radionuclide, enzyme, substrate, cofactor, fluorescent marker, chemiluminescent marker, peptide tag, magnetic particle, drug, and toxin.

4. The antibody, or antigen binding fragment of claim 1, wherein the antibody, or antigen binding fragment, specifically binds to the polypeptide of SEQ ID NO:2 or SEQ ID NO:3.

5. The antibody, or antigen binding fragment of claim 1, wherein the antibody, or antigen binding fragment is humanized.

6. The antibody, or antigen binding fragment, of claim 1, wherein the antibody is an antigen binding fragment.

7. The antibody of claim 6, wherein the fragment is selected from the group consisting of F(ab')2, F(ab)2, Fab', and Fab.

8. The antibody of claim 6, wherein the fragment is a synthetic or a genetically engineered polypeptide.

9. A monoclonal antibody, or antigen binding fragment thereof, comprising the heavy and light chain CDR1, CDR2, and CDR3 regions of an antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1 (ATCC PTA-5037); and (e) the hybridoma clone 266.12.6.1.3.2.1 (ATCC PTA-5034); and (e) the hybridoma clone 266.19.1.10.5.2 (ATCC PTA-5036).

10. The antibody, or antigen binding fragment, of claim 9, wherein the antibody, or antigen binding fragment is linked to a therapeutic agent.

11. The antibody, or antigen binding fragment, of claim 10, wherein the therapeutic agent is selected from the group consisting of a radionuclide, enzyme, substrate, cofactor, fluorescent marker, chemiluminescent marker, peptide tag, magnetic particle, drug, and toxin.

12. The antibody, or antigen binding fragment, of claim 9, wherein the antibody, or antigen binding fragment, specifically binds to the polypeptide of SEQ ID NO:2 or SEQ ID NO:3.

13. The antibody, or antigen binding fragment of claim 9, wherein the antibody, or antigen binding fragment is humanized.

14. The antibody, or antigen binding fragment, of claim 9, wherein the antibody is an antigen binding fragment.

15. The antibody of claim 14, wherein the fragment is selected from the group consisting of F(ab')2, F(ab)2, Fab', and Fab.

16. The antibody of claim 14, wherein the fragment is a synthetic or a genetically engineered polypeptide.

* * * * *

UNITED STATES PATENT AND TRADEMARK OFFICE
CERTIFICATE OF CORRECTION

PATENT NO. : 8,524,227 B2
APPLICATION NO. : 12/732116
DATED : September 3, 2013
INVENTOR(S) : Wenfeng Xu et al.

It is certified that error appears in the above-identified patent and that said Letters Patent is hereby corrected as shown below:

In the Claims:

At column 155, line 62 through column 156, line 63, please replace existing claim 1:

"A monoclonal antibody, or antigen binding fragment thereof, comprising the heavy and light chain variable regions of an antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1 (ATCC PTA-5037); and (e) the hybridoma clone 266.12.6.1.3.2.1 (ATCC PTA-5034); and (e) the hybridoma clone 266.19.1.10.5.2 (ATCC PTA-5036)."

with the following:

--A monoclonal antibody, or antigen binding fragment thereof, comprising the heavy and light chain variable regions of an antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1 (ATCC PTA-5037); and (e) the hybridoma clone 266.12.6.1.3.2.1 (ATCC PTA-5034); and (f) the hybridoma clone 266.19.1.10.5.2 (ATCC PTA-5036).--

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,524,227 B2  
APPLICATION NO. : 12/732116  
DATED : September 3, 2013  
INVENTOR(S) : Wenfeng Xu et al.

Page 1 of 1

It is certified that error appears in the above-identified patent and that said Letters Patent is hereby corrected as shown below:

In the Claims

At column 157, line 20 through column 158, line 3, please replace existing claim 9:

"A monoclonal antibody, or antigen binding fragment thereof, comprising the heavy and light chain CDR1, CDR2, and CDR3 regions of an antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1 (ATCC PTA-5037); and (e) the hybridoma clone 266.12.6.1.3.2.1 (ATCC PTA-5034); and (e) the hybridoma clone 266.19.1.10.5.2 (ATCC PTA-5036)."

with the following:

--A monoclonal antibody, or antigen binding fragment thereof, comprising the heavy and light chain CDR1, CDR2, and CDR3 regions of an antibody produced from a hybridoma selected from the group consisting of: (a) the hybridoma clone 266.16.1.4.4.1 (ATCC PTA-5035); (b) the hybridoma clone 266.5.1.2.2.3 (ATCC PTA-5033); (c) the hybridoma clone 267.17.1.1.4.1 (ATCC PTA-5038); (d) the hybridoma clone 267.4.1.1.4.1 (ATCC PTA-5037); and (e) the hybridoma clone 266.12.6.1.3.2.1 (ATCC PTA-5034); and (f) the hybridoma clone 266.19.1.10.5.2 (ATCC PTA-5036).--

Signed and Sealed this  
Twenty-fourth Day of June, 2014

Michelle K. Lee  
*Deputy Director of the United States Patent and Trademark Office*

SEQUENCE LISTING

```
<160> NUMBER OF SEQ ID NOS: 67

<210> SEQ ID NO 1
<211> LENGTH: 1116
<212> TYPE: DNA
<213> ORGANISM: Homo sapiens
<220> FEATURE:
<221> NAME/KEY: CDS
<222> LOCATION: (21)...(557)

<400> SEQUENCE: 1
tcgagttaga attgtctgca atg gcc gcc ctg cag aaa tct gtg agc tct ttc       53
                     Met Ala Ala Leu Gln Lys Ser Val Ser Ser Phe
                      1               5                  10 ctt atg ggg acc ctg gcc acc agc tgc ctc ctt ctc ttg gcc ctc ttg       101
Leu Met Gly Thr Leu Ala Thr Ser Cys Leu Leu Leu Leu Ala Leu Leu
             15                  20                  25 gta cag gga gga gca gct gcg ccc atc agc tcc cac tgc agg ctt gac       149
Val Gln Gly Gly Ala Ala Ala Pro Ile Ser Ser His Cys Arg Leu Asp
         30                  35                  40 aag tcc aac ttc cag cag ccc tat atc acc aac cgc acc ttc atg ctg       197
Lys Ser Asn Phe Gln Gln Pro Tyr Ile Thr Asn Arg Thr Phe Met Leu
     45                  50                  55 gct aag gag gct agc ttg gct gat aac aac aca gac gtt cgt ctc att       245
Ala Lys Glu Ala Ser Leu Ala Asp Asn Asn Thr Asp Val Arg Leu Ile
 60                  65                  70                  75 ggg gag aaa ctg ttc cac gga gtc agt atg agt gag cgc tgc tat ctg       293
Gly Glu Lys Leu Phe His Gly Val Ser Met Ser Glu Arg Cys Tyr Leu
                 80                  85                  90 atg aag cag gtg ctg aac ttc acc ctt gaa gaa gtg ctg ttc cct caa       341
Met Lys Gln Val Leu Asn Phe Thr Leu Glu Glu Val Leu Phe Pro Gln
             95                 100                 105 tct gat agg ttc cag cct tat atg cag gag gtg gtg ccc ttc ctg gcc       389
Ser Asp Arg Phe Gln Pro Tyr Met Gln Glu Val Val Pro Phe Leu Ala
        110                 115                 120 agg ctc agc aac agg cta agc aca tgt cat att gaa ggt gat gac ctg       437
Arg Leu Ser Asn Arg Leu Ser Thr Cys His Ile Glu Gly Asp Asp Leu
    125                 130                 135 cat atc cag agg aat gtg caa aag ctg aag gac aca gtg aaa aag ctt       485
His Ile Gln Arg Asn Val Gln Lys Leu Lys Asp Thr Val Lys Lys Leu
140                 145                 150                 155 gga gag agt gga gag atc aaa gca att gga gaa ctg gat ttg ctg ttt       533
Gly Glu Ser Gly Glu Ile Lys Ala Ile Gly Glu Leu Asp Leu Leu Phe
                160                 165                 170
```

```
atg tct ctg aga aat gcc tgc att tgaccagagc aaagctgaaa atgaataac      587
Met Ser Leu Arg Asn Ala Cys Ile
            175 taaccccctt tccctgctag aaataacaat tagatgcccc aaagcgattt ttttttaacca    647 aaaggaagat gggaagccaa actccatcat gatgggtgga ttccaaatga acccctgcgt     707 tagttacaaa ggaaaccaat gccacttttg tttataagac cagaaggtag actttctaag    767 catagatatt tattgataac atttcattgt aactggtgtt ctatacacag aaacaatttt    827 atttttaaaa taattgtctt tttccataaa aaagattact ttccattcct ttaggggaaa    887 aaaccctaa atagcttcat gtttccataa tcagtacttt atatttataa atgtatttat     947 tattattata agactgcatt ttatttatat cattttatta atatggattt atttatagaa    1007 acatcattcg atattgctac ttgagtgtaa ggctaatatt gatatttatg acaataatta    1067 tagagctata acatgtttat ttgacctcaa taaacacttg gatatccta                1116
```

<210> SEQ ID NO 2
<211> LENGTH: 179
<212> TYPE: PRT
<213> ORGANISM: Homo sapiens

<400> SEQUENCE: 2

```
Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 3
<211> LENGTH: 167
<212> TYPE: PRT
<213> ORGANISM: Homo sapiens

<400> SEQUENCE: 3

```
Met Gly Thr Leu Ala Thr Ser Cys Leu Leu Leu Ala Leu Leu Val
1               5                   10                  15

Gln Gly Gly Ala Ala Ala Pro Ile Ser Ser His Cys Arg Leu Asp Lys
            20                  25                  30

Ser Asn Phe Gln Gln Pro Tyr Ile Thr Asn Arg Thr Phe Met Leu Ala
```

```
                35                   40                  45
Lys Glu Ala Ser Leu Ala Asp Asn Asn Thr Asp Val Arg Leu Ile Gly
 50                  55                  60

Glu Lys Leu Phe His Gly Val Ser Met Ser Glu Arg Cys Tyr Leu Met
 65                  70                  75                  80

Lys Gln Val Leu Asn Phe Thr Leu Glu Glu Val Leu Phe Pro Gln Ser
                 85                  90                  95

Asp Arg Phe Gln Pro Tyr Met Gln Glu Val Val Pro Phe Leu Ala Arg
                100                 105                 110

Leu Ser Asn Arg Leu Ser Thr Cys His Ile Glu Gly Asp Asp Leu His
                115                 120                 125

Ile Gln Arg Asn Val Gln Lys Leu Lys Asp Thr Val Lys Lys Leu Gly
            130                 135                 140

Glu Ser Gly Glu Ile Lys Ala Ile Gly Glu Leu Asp Leu Leu Phe Met
145                 150                 155                 160

Ser Leu Arg Asn Ala Cys Ile
                165

<210> SEQ ID NO 4
<211> LENGTH: 501
<212> TYPE: DNA
<213> ORGANISM: Artificial Sequence
<220> FEATURE:
<223> OTHER INFORMATION: Degenerate polynucleotide of zcyto18
<220> FEATURE:
<221> NAME/KEY: misc_feature
<222> LOCATION: (1)...(501)
<223> OTHER INFORMATION: n = A,T,C or G

<400> SEQUENCE: 4
atgggnacny tngcnacnws ntgyytnytn ytnytngcny tnytngtnca rggnggngcn     60
gcngcnccna thwsnwsnca ytgymgnytn gayaarwsna ayttycarca rccntayath    120
acnaaymgna cnttyatgyt ngcnaargar gcnwsnytng cngayaayaa yacngaygtn    180
mgnytnathg gngaraaryt nttycayggn gtnwsnatgw sngarmgntg ytayytnatg    240
aarcargtny tnaayttyac nytngargar gtnytnttyc cncarwsnga ymgnttycar    300
ccntayatgc argargtngt nccnttyytn gcnmgnytnw snaaymgnyt nwsnacntgy    360
cayathgarg gngaygayyt ncayathcar mgnaaygtnc araarytnaa rgayacngtn    420
aaraarytng gngarwsngg ngarathaar gcnathggng arytngayyt nytnttyatg    480
wsnytnmgna aygcntgyat h                                              501

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer ZC25840

<400> SEQUENCE: 5
ctggatatgc aggtcatcac cttc                                            24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer ZC25841

<400> SEQUENCE: 6
```

```
tcgagttaga attgtctgca atgg                                           24

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer ZC25838

<400> SEQUENCE: 7
aggttctcct tccccagtca cca                                            23

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer ZC25839

<400> SEQUENCE: 8
tagcctcctt agccagcatg aag                                            23

<210> SEQ ID NO 9
<211> LENGTH: 40
<212> TYPE: DNA
<213> ORGANISM: Artificial Sequence
<220> FEATURE:
<223> OTHER INFORMATION: Oligonucleotide primer ZC13946

<400> SEQUENCE: 9
ccctgcagtg atcaacatgg ccaagttgac cagtgccgtt                          40

<210> SEQ ID NO 10
<211> LENGTH: 45
<212> TYPE: DNA
<213> ORGANISM: Artificial Sequence
<220> FEATURE:
<223> OTHER INFORMATION: Oligonucleotide primer ZC13945

<400> SEQUENCE: 10
gcccatggac tagtttcgaa aggtcgagtg tcagtcctgc tcctc                    45

<210> SEQ ID NO 11
<211> LENGTH: 34
<212> TYPE: DNA
<213> ORGANISM: Artificial Sequence
<220> FEATURE:
<223> OTHER INFORMATION: Oligonucleotide primer ZC18698

<400> SEQUENCE: 11
tttttttctc gagactttt tttttttttt tttt                                 34

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer ZC26414

<400> SEQUENCE: 12
agctgcctcc ttctcttg                                                  18

<210> SEQ ID NO 13
<211> LENGTH: 18
<212> TYPE: DNA
<213> ORGANISM: Artificial Sequence
<220> FEATURE:
```

<223> OTHER INFORMATION: Oligonucleotide primer ZC26415

<400> SEQUENCE: 13
tagggctgct ggaagttg                                                     18

<210> SEQ ID NO 14
<211> LENGTH: 6
<212> TYPE: PRT
<213> ORGANISM: Artificial Sequence
<220> FEATURE:
<223> OTHER INFORMATION: Glu-Glu (CEE) peptide Tag amino acid sequence

<400> SEQUENCE: 14

Glu Tyr Met Pro Met Glu
 1               5

<210> SEQ ID NO 15
<211> LENGTH: 8
<212> TYPE: PRT
<213> ORGANISM: Artificial Sequence
<220> FEATURE:
<223> OTHER INFORMATION: C-terminal FLAG peptide tag

<400> SEQUENCE: 15

Asp Tyr Lys Asp Asp Asp Asp Lys
 1               5

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide primer ZC28590

<400> SEQUENCE: 16
ttgggtacct ctgcaatggc cgccctgcag aaatct                                 36

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide primer ZC28580

<400> SEQUENCE: 17
ttgggatcca atgcaggcat ttctcagaga cat                                    33

<210> SEQ ID NO 18
<211> LENGTH: 2831
<212> TYPE: DNA
<213> ORGANISM: Homo sapiens
<220> FEATURE:
<221> NAME/KEY: CDS
<222> LOCATION: (34)...(1755)

<400> SEQUENCE: 18
tagaggccaa gggagggctc tgtgccagcc ccg atg agg acg ctg ctg acc atc        54
                                    Met Arg Thr Leu Leu Thr Ile
                                     1               5 ttg act gtg gga tcc ctg gct gct cac gcc cct gag gac ccc tcg gat        102
Leu Thr Val Gly Ser Leu Ala Ala His Ala Pro Glu Asp Pro Ser Asp
         10                  15                  20 ctg ctc cag cac gtg aaa ttc cag tcc agc aac ttt gaa aac atc ctg        150
Leu Leu Gln His Val Lys Phe Gln Ser Ser Asn Phe Glu Asn Ile Leu
     25                  30                  35 acg tgg gac agc ggg cca gag ggc acc cca gac acg gtc tac agc atc        198

-continued

| | | | | | | | | | | | | | | | |
|---|---|---|---|---|---|---|---|---|---|---|---|---|---|---|---|
| Thr | Trp | Asp | Ser | Gly | Pro | Glu | Gly | Thr | Pro | Asp | Thr | Val | Tyr | Ser | Ile |
| 40 | | | | | 45 | | | | 50 | | | | | | 55 |

```
gag tat aag acg tac gga gag agg gac tgg gtg gca aag aag ggc tgt    246
Glu Tyr Lys Thr Tyr Gly Glu Arg Asp Trp Val Ala Lys Lys Gly Cys
                60                  65                  70 cag cgg atc acc cgg aag tcc tgc aac ctg acg gtg gag acg ggc aac    294
Gln Arg Ile Thr Arg Lys Ser Cys Asn Leu Thr Val Glu Thr Gly Asn
            75                  80                  85 ctc acg gag ctc tac tat gcc agg gtc acc gct gtc agt gcg gga ggc    342
Leu Thr Glu Leu Tyr Tyr Ala Arg Val Thr Ala Val Ser Ala Gly Gly
        90                  95                 100 cgg tca gcc acc aag atg act gac agg ttc agc tct ctg cag cac act    390
Arg Ser Ala Thr Lys Met Thr Asp Arg Phe Ser Ser Leu Gln His Thr
    105                 110                 115 acc ctc aag cca cct gat gtg acc tgt atc tcc aaa gtg aga tcg att    438
Thr Leu Lys Pro Pro Asp Val Thr Cys Ile Ser Lys Val Arg Ser Ile
120                 125                 130                 135 cag atg att gtt cat cct acc ccc acg cca atc cgt gca ggc gat ggc    486
Gln Met Ile Val His Pro Thr Pro Thr Pro Ile Arg Ala Gly Asp Gly
            140                 145                 150 cac cgg cta acc ctg gaa gac atc ttc cat gac ctg ttc tac cac tta    534
His Arg Leu Thr Leu Glu Asp Ile Phe His Asp Leu Phe Tyr His Leu
        155                 160                 165 gag ctc cag gtc aac cgc acc tac caa atg cac ctt gga ggg aag cag    582
Glu Leu Gln Val Asn Arg Thr Tyr Gln Met His Leu Gly Gly Lys Gln
    170                 175                 180 aga gaa tat gag ttc ttc ggc ctg acc cct gac aca gag ttc ctt ggc    630
Arg Glu Tyr Glu Phe Phe Gly Leu Thr Pro Asp Thr Glu Phe Leu Gly
185                 190                 195 acc atc atg att tgc gtt ccc acc tgg gcc aag gag agt gcc ccc tac    678
Thr Ile Met Ile Cys Val Pro Thr Trp Ala Lys Glu Ser Ala Pro Tyr
200                 205                 210                 215 atg tgc cga gtg aag aca ctg cca gac cgg aca tgg acc tac tcc ttc    726
Met Cys Arg Val Lys Thr Leu Pro Asp Arg Thr Trp Thr Tyr Ser Phe
            220                 225                 230 tcc gga gcc ttc ctg ttc tcc atg ggc ttc ctc gtc gca gta ctc tgc    774
Ser Gly Ala Phe Leu Phe Ser Met Gly Phe Leu Val Ala Val Leu Cys
        235                 240                 245 tac ctg agc tac aga tat gtc acc aag ccg cct gca cct ccc aac tcc    822
Tyr Leu Ser Tyr Arg Tyr Val Thr Lys Pro Pro Ala Pro Pro Asn Ser
    250                 255                 260 ctg aac gtc cag cga gtc ctg act ttc cag ccg ctg cgc ttc atc cag    870
Leu Asn Val Gln Arg Val Leu Thr Phe Gln Pro Leu Arg Phe Ile Gln
265                 270                 275 gag cac gtc ctg atc cct gtc ttt gac ctc agc ggc ccc agc agt ctg    918
Glu His Val Leu Ile Pro Val Phe Asp Leu Ser Gly Pro Ser Ser Leu
280                 285                 290                 295 gcc cag cct gtc cag tac tcc cag atc agg gtg tct gga ccc agg gag    966
Ala Gln Pro Val Gln Tyr Ser Gln Ile Arg Val Ser Gly Pro Arg Glu
            300                 305                 310 ccc gca gga gct cca cag cgg cat agc ctg tcc gag atc acc tac tta   1014
Pro Ala Gly Ala Pro Gln Arg His Ser Leu Ser Glu Ile Thr Tyr Leu
        315                 320                 325 ggg cag cca gac atc tcc atc ctc cag ccc tcc aac gtg cca cct ccc   1062
Gly Gln Pro Asp Ile Ser Ile Leu Gln Pro Ser Asn Val Pro Pro Pro
    330                 335                 340 cag atc ctc tcc cca ctg tcc tat gcc cca aac gct gcc cct gag gtc   1110
Gln Ile Leu Ser Pro Leu Ser Tyr Ala Pro Asn Ala Ala Pro Glu Val
345                 350                 355 ggg ccc cca tcc tat gca cct cag gtg acc ccc gaa gct caa ttc cca   1158
```

```
Gly Pro Pro Ser Tyr Ala Pro Gln Val Thr Pro Glu Ala Gln Phe Pro
360                 365                 370                 375 ttc tac gcc cca cag gcc atc tct aag gtc cag cct tcc tcc tat gcc    1206
Phe Tyr Ala Pro Gln Ala Ile Ser Lys Val Gln Pro Ser Ser Tyr Ala
                380                 385                 390 cct caa gcc act ccg gac agc tgg cct ccc tcc tat ggg gta tgc atg    1254
Pro Gln Ala Thr Pro Asp Ser Trp Pro Pro Ser Tyr Gly Val Cys Met
                395                 400                 405 gaa ggt tct ggc aaa gac tcc ccc act ggg aca ctt tct agt cct aaa    1302
Glu Gly Ser Gly Lys Asp Ser Pro Thr Gly Thr Leu Ser Ser Pro Lys
            410                 415                 420 cac ctt agg cct aaa ggt cag ctt cag aaa gag cca cca gct gga agc    1350
His Leu Arg Pro Lys Gly Gln Leu Gln Lys Glu Pro Pro Ala Gly Ser
        425                 430                 435 tgc atg tta ggt ggc ctt tct ctg cag gag gtg acc tcc ttg gct atg    1398
Cys Met Leu Gly Gly Leu Ser Leu Gln Glu Val Thr Ser Leu Ala Met
440                 445                 450                 455 gag gaa tcc caa gaa gca aaa tca ttg cac cag ccc ctg ggg att tgc    1446
Glu Glu Ser Gln Glu Ala Lys Ser Leu His Gln Pro Leu Gly Ile Cys
                460                 465                 470 aca gac aga aca tct gac cca aat gtg cta cac agt ggg gag gaa ggg    1494
Thr Asp Arg Thr Ser Asp Pro Asn Val Leu His Ser Gly Glu Glu Gly
                475                 480                 485 aca cca cag tac cta aag ggc cag ctc ccc ctc ctc tcc tca gtc cag    1542
Thr Pro Gln Tyr Leu Lys Gly Gln Leu Pro Leu Leu Ser Ser Val Gln
            490                 495                 500 atc gag ggc cac ccc atg tcc ctc cct ttg caa cct cct tcc ggt cca    1590
Ile Glu Gly His Pro Met Ser Leu Pro Leu Gln Pro Pro Ser Gly Pro
505                 510                 515 tgt tcc ccc tcg gac caa ggt cca agt ccc tgg ggc ctg ctg gag tcc    1638
Cys Ser Pro Ser Asp Gln Gly Pro Ser Pro Trp Gly Leu Leu Glu Ser
520                 525                 530                 535 ctt gtg tgt ccc aag gat gaa gcc aag agc cca gcc cct gag acc tca    1686
Leu Val Cys Pro Lys Asp Glu Ala Lys Ser Pro Ala Pro Glu Thr Ser
                540                 545                 550 gac ctg gag cag ccc aca gaa ctg gat tct ctt ttc aga ggc ctg gcc    1734
Asp Leu Glu Gln Pro Thr Glu Leu Asp Ser Leu Phe Arg Gly Leu Ala
                555                 560                 565 ctg act gtg cag tgg gag tcc tgaggggaat gggaaaggct tggtgcttcc       1785
Leu Thr Val Gln Trp Glu Ser
            570 tccctgtccc tacccagtgt cacatccttg gctgtcaatc ccatgcctgc ccatgccaca  1845 cactctgcga tctggcctca gacgggtgcc cttgagagaa gcagagggag tggcatgcag  1905 ggcccctgcc atgggtgcgc tcctcaccgg aacaaagcag catgataagg actgcagcgg  1965 gggagctctg gggagcagct tgtgtagaca agcgcgtgct cgctgagccc tgcaaggcag  2025 aaatgacagt gcaaggagga aatgcaggga aactcccgag gtccagagcc ccacctccta  2085 acaccatgga ttcaaagtgc tcagggaatt gcctctcct tgccccattc ctggccagtt   2145 tcacaatcta gctcgacaga gcatgaggcc cctgcctctt ctgtcattgt tcaaaggtgg  2205 gaagagagcc tggaaaagaa ccaggcctgg aaaagaacca gaaggaggct gggcagaacc   2265 agaacaacct gcacttctgc caaggccagg ccagcagga cggcaggact ctagggaggg    2325 gtgtggcctg cagctcattc ccagccaggg caactgcctg acgttgcacg atttcagctt  2385 cattcctctg atagaacaaa gcgaaatgca ggtccaccag ggagggagac acacaagcct  2445 tttctgcagg caggagtttc agaccctatc ctgagaatgg ggtttgaaag gaaggtgagg  2505 gctgtggccc ctggacgggt acaataacac actgtactga tgtcacaact ttgcaagctc  2565
```

```
tgccttgggt tcagcccatc tgggctcaaa ttccagcctc accactcaca agctgtgtga    2625
cttcaaacaa atgaaatcag tgcccagaac ctcggtttcc tcatctgtaa tgtggggatc    2685
ataacaccta cctcatggag ttgtggtgaa gatgaaatga agtcatgtct ttaaagtgct    2745
taatagtgcc tggtacatgg gcagtgccca ataaacggta gctatttaaa aaaaaaaaa     2805 aaaaaaaaaa atagcggccg cctcga                                         2831

<210> SEQ ID NO 19
<211> LENGTH: 574
<212> TYPE: PRT
<213> ORGANISM: Homo sapiens

<400> SEQUENCE: 19

Met Arg Thr Leu Leu Thr Ile Leu Thr Val Gly Ser Leu Ala Ala His
  1               5                  10                  15

Ala Pro Glu Asp Pro Ser Asp Leu Leu Gln His Val Lys Phe Gln Ser
                 20                  25                  30

Ser Asn Phe Glu Asn Ile Leu Thr Trp Asp Ser Gly Pro Glu Gly Thr
             35                  40                  45

Pro Asp Thr Val Tyr Ser Ile Glu Tyr Lys Thr Tyr Gly Glu Arg Asp
         50                  55                  60

Trp Val Ala Lys Lys Gly Cys Gln Arg Ile Thr Arg Lys Ser Cys Asn
 65                  70                  75                  80

Leu Thr Val Glu Thr Gly Asn Leu Thr Glu Leu Tyr Tyr Ala Arg Val
                 85                  90                  95

Thr Ala Val Ser Ala Gly Gly Arg Ser Ala Thr Lys Met Thr Asp Arg
                100                 105                 110

Phe Ser Ser Leu Gln His Thr Thr Leu Lys Pro Pro Asp Val Thr Cys
            115                 120                 125

Ile Ser Lys Val Arg Ser Ile Gln Met Ile Val His Pro Thr Pro Thr
        130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
```

```
                    325                 330                 335
Pro Ser Asn Val Pro Pro Gln Ile Leu Ser Pro Leu Ser Tyr Ala
            340                 345                 350
Pro Asn Ala Ala Pro Glu Val Gly Pro Pro Ser Tyr Ala Pro Gln Val
        355                 360                 365
Thr Pro Glu Ala Gln Phe Pro Phe Tyr Ala Pro Gln Ala Ile Ser Lys
    370                 375                 380
Val Gln Pro Ser Ser Tyr Ala Pro Gln Ala Thr Pro Asp Ser Trp Pro
385                 390                 395                 400
Pro Ser Tyr Gly Val Cys Met Glu Gly Ser Gly Lys Asp Ser Pro Thr
                405                 410                 415
Gly Thr Leu Ser Ser Pro Lys His Leu Arg Pro Lys Gly Gln Leu Gln
            420                 425                 430
Lys Glu Pro Pro Ala Gly Ser Cys Met Leu Gly Gly Leu Ser Leu Gln
        435                 440                 445
Glu Val Thr Ser Leu Ala Met Glu Glu Ser Gln Glu Ala Lys Ser Leu
    450                 455                 460
His Gln Pro Leu Gly Ile Cys Thr Asp Arg Thr Ser Asp Pro Asn Val
465                 470                 475                 480
Leu His Ser Gly Glu Glu Gly Thr Pro Gln Tyr Leu Lys Gly Gln Leu
                485                 490                 495
Pro Leu Leu Ser Ser Val Gln Ile Glu Gly His Pro Met Ser Leu Pro
            500                 505                 510
Leu Gln Pro Pro Ser Gly Pro Cys Ser Pro Ser Asp Gln Gly Pro Ser
        515                 520                 525
Pro Trp Gly Leu Leu Glu Ser Leu Val Cys Pro Lys Asp Glu Ala Lys
    530                 535                 540
Ser Pro Ala Pro Glu Thr Ser Asp Leu Glu Gln Pro Thr Glu Leu Asp
545                 550                 555                 560
Ser Leu Phe Arg Gly Leu Ala Leu Thr Val Gln Trp Glu Ser
                565                 570

<210> SEQ ID NO 20
<211> LENGTH: 39
<212> TYPE: DNA
<213> ORGANISM: Artificial Sequence
<220> FEATURE:
<223> OTHER INFORMATION: Oligonucleotide primer ZC26665

<400> SEQUENCE: 20
cacacaggcc ggccaccatg gccgccctgc agaaatctg                          39

<210> SEQ ID NO 21
<211> LENGTH: 37
<212> TYPE: DNA
<213> ORGANISM: Artificial Sequence
<220> FEATURE:
<223> OTHER INFORMATION: Oligonucleotide primer ZC26666

<400> SEQUENCE: 21
cacacaggcg cgcctcaaat gcaggcattt ctcagag                            37

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide primer ZC14666

<400> SEQUENCE: 22
```

-continued agccaccaag atgactga                                              18

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide primer ZC14742

<400> SEQUENCE: 23
tgcatttggt aggtgcggtt ga                                         22

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide primer ZC25963

<400> SEQUENCE: 24
agtcaacgca tgagtctctg aag                                        23

<210> SEQ ID NO 25
<211> LENGTH: 23
<212> TYPE: DNA
<213> ORGANISM: Artificial Sequence
<220> FEATURE:
<223> OTHER INFORMATION: Oligonucleotide primer ZC28354

<400> SEQUENCE: 25
accaacaaag agccattgac ttg                                        23

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide primer ZC21195

<400> SEQUENCE: 26
gaggagacca taacccccga cag                                        23

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide primer ZC21196

<400> SEQUENCE: 27
catagctccc accacacgat ttt                                        23

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 28
caccagacat aatagctgac agact                                      25

<210> SEQ ID NO 29
<211> LENGTH: 21
<212> TYPE: DNA
<213> ORGANISM: Artificial Sequence -continued

```
<220> FEATURE:
<223> OTHER INFORMATION: Oligonucleotide primer ZC17574

<400> SEQUENCE: 29
ggtrttgctc agcatgcaca c                                              21

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide primer ZC17600

<400> SEQUENCE: 30
catgtaggcc atgaggtcca ccac                                           24

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer ZC25964

<400> SEQUENCE: 31
gttcttgagt accccaacag tct                                            23

<210> SEQ ID NO 32
<211> LENGTH: 2149
<212> TYPE: DNA
<213> ORGANISM: Homo sapiens
<220> FEATURE:
<221> NAME/KEY: CDS
<222> LOCATION: (1)...(693)

<400> SEQUENCE: 32 atg atg cct aaa cat tgc ttt cta ggc ttc ctc atc agt ttc ttc ctt     48
Met Met Pro Lys His Cys Phe Leu Gly Phe Leu Ile Ser Phe Phe Leu
 1               5                  10                  15 act ggt gta gca gga act cag tca acg cat gag tct ctg aag cct cag     96
Thr Gly Val Ala Gly Thr Gln Ser Thr His Glu Ser Leu Lys Pro Gln
            20                  25                  30 agg gta caa ttt cag tcc cga aat ttt cac aac att ttg caa tgg cag    144
Arg Val Gln Phe Gln Ser Arg Asn Phe His Asn Ile Leu Gln Trp Gln
        35                  40                  45 cct ggg agg gca ctt act ggc aac agc agt gtc tat ttt gtg cag tac    192
Pro Gly Arg Ala Leu Thr Gly Asn Ser Ser Val Tyr Phe Val Gln Tyr
    50                  55                  60 aaa ata tat gga cag aga caa tgg aaa aat aaa gaa gac tgt tgg ggt    240
Lys Ile Tyr Gly Gln Arg Gln Trp Lys Asn Lys Glu Asp Cys Trp Gly
65                  70                  75                  80 act caa gaa ctc tct tgt gac ctt acc agt gaa acc tca gac ata cag    288
Thr Gln Glu Leu Ser Cys Asp Leu Thr Ser Glu Thr Ser Asp Ile Gln
                85                  90                  95 gaa cct tat tac ggg agg gtg agg gcg gcc tcg gct ggg agc tac tca    336
Glu Pro Tyr Tyr Gly Arg Val Arg Ala Ala Ser Ala Gly Ser Tyr Ser
            100                 105                 110 gaa tgg agc atg acg ccg cgg ttc act ccc tgg tgg gaa aca aaa ata    384
Glu Trp Ser Met Thr Pro Arg Phe Thr Pro Trp Trp Glu Thr Lys Ile
        115                 120                 125 gat cct cca gtc atg aat ata acc caa gtc aat ggc tct ttg ttg gta    432
Asp Pro Pro Val Met Asn Ile Thr Gln Val Asn Gly Ser Leu Leu Val
    130                 135                 140 att ctc cat gct cca aat tta cca tat aga tac caa aag gaa aaa aat    480
Ile Leu His Ala Pro Asn Leu Pro Tyr Arg Tyr Gln Lys Glu Lys Asn
```

```
                         145                 150                 155                 160
gta tct ata gaa gat tac tat gaa cta cta tac cga gtt ttt ata att       528
Val Ser Ile Glu Asp Tyr Tyr Glu Leu Leu Tyr Arg Val Phe Ile Ile
                165                 170                 175 aac aat tca cta gaa aag gag caa aag gtt tat gaa ggg gct cac aga       576
Asn Asn Ser Leu Glu Lys Glu Gln Lys Val Tyr Glu Gly Ala His Arg
            180                 185                 190 gcg gtt gaa att gaa gct cta aca cca cac tcc agc tac tgt gta gtg       624
Ala Val Glu Ile Glu Ala Leu Thr Pro His Ser Ser Tyr Cys Val Val
        195                 200                 205 gct gaa ata tat cag ccc atg tta gac aga aga agt cag aga agt gaa       672
Ala Glu Ile Tyr Gln Pro Met Leu Asp Arg Arg Ser Gln Arg Ser Glu
    210                 215                 220 gag aga tgt gtg gaa att cca tgacttgtgg aatttggcat tcagcaatgt          723
Glu Arg Cys Val Glu Ile Pro
225                 230 ggaaattcta aagctccctg agaacaggat gactcgtgtt tgaaggatct tatttaaaat      783
tgttttgta ttttcttaaa gcaatattca ctgttacacc ttggggactt ctttgtttat       843
ccattctttt atcctttata tttcatttta aactatattt gaacgacatt ccccccgaaa      903
aattgaaatg taaagatgag gcagagaata aagtgttcta tgaaattcag aactttattt      963
ctgaatgtaa catccctaat aacaaccttc attcttctaa tacagcaaaa taaaaattta     1023
acaaccaagg aatagtattt aagaaaatgt tgaataatt tttttaaaat agcattacag      1083
actgaggcgg tcctgaagca atggttttc actctcttat tgagccaatt aaattgacat      1143
tgctttgaca atttaaaact tctataaagg tgaatatttt tcatacattt ctatttata      1203
tgaatatact ttttatatat ttattattat taaatatttc tacttaatga atcaaaattt     1263
tgttttaaag tctactttat gtaaataaga acaggttttg gggaaaaaaa tcttatgatt     1323
tctggattga tatctgaatt aaaactatca acaacaagga agtctactct gtacaattgt     1383
ccctcattta aaagatatat taagcttttc ttttctgttt gttttgttt tgtttagttt      1443
ttaatcctgt cttagaagaa cttatcttta ttctcaaaat taaatgtaat tttttagtg      1503
acaaagaaga aaggaaacct cattactcaa tccttctggc caagagtgtc ttgcttgtgg    1563
cgccttcctc atctctatat aggaggatcc catgaatgat ggtttattgg gaactgctgg    1623
ggtcgacccc atacagagaa ctcagcttga agctggaagc acacagtggg tagcaggaga    1683
aggaccggtg ttggtaggtg cctacagaga ctatagagct agacaaagcc ctccaaactg    1743
gcccctcctg ctcactgcct ctcctgagta gaaatctggt gacctaaggc tcagtgcggt    1803
caacagaaag ctgccttctt cacttgaggc taagtcttca tatatgttta aggttgtctt    1863
tctagtgagg agatacatat cagagaacat ttgtacaatt ccccatgaaa attgctccaa    1923
agttgataac aatatagtcg gtgcttctag ttatatgcaa gtactcagtg ataaatggat    1983
taaaaaatat tcagaaatgt attggggggt ggaggagaat aagaggcaga gcaagagcta    2043
gagaattggt ttccttgctt ccctgtatgc tcagaaaaca ttgatttgag catagacgca    2103
gagactgaaa aaaaaaaaat gctcgagcgg ccgccatatc cttggt                   2149
```

<210> SEQ ID NO 33
<211> LENGTH: 231
<212> TYPE: PRT
<213> ORGANISM: Homo sapiens

<400> SEQUENCE: 33

```
Met Met Pro Lys His Cys Phe Leu Gly Phe Leu Ile Ser Phe Phe Leu
1               5                   10                  15
```

```
Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 34
<211> LENGTH: 29
<212> TYPE: PRT
<213> ORGANISM: Artificial Sequence
<220> FEATURE:
<223> OTHER INFORMATION: Human zcyto18 peptide 1 (huzcyto18-1)

<400> SEQUENCE: 34

Lys Glu Ala Ser Leu Ala Asp Asn Asn Thr Asp Val Arg Leu Ile Gly
 1               5                  10                  15

Glu Lys Leu Phe His Gly Val Ser Met Ser Glu Arg Cys
            20                  25

<210> SEQ ID NO 35
<211> LENGTH: 21
<212> TYPE: PRT
<213> ORGANISM: Artificial Sequence
<220> FEATURE:
<223> OTHER INFORMATION: Human zcyto18 peptide 2 (huzcyto18-2)

<400> SEQUENCE: 35

Glu Glu Val Leu Phe Pro Gln Ser Asp Arg Phe Gln Pro Tyr Met Gln
 1               5                  10                  15

Glu Val Val Pro Cys
            20

<210> SEQ ID NO 36
<211> LENGTH: 24
<212> TYPE: PRT
<213> ORGANISM: Artificial Sequence
```

```
<220> FEATURE:
<223> OTHER INFORMATION: Human zcyto18 peptide 3 (huzcyto18-3)

<400> SEQUENCE: 36

Cys Asn Val Gln Lys Leu Lys Asp Thr Val Lys Lys Leu Gly Glu Ser
  1               5                  10                  15

Gly Glu Ile Lys Ala Ile Gly Glu
            20

<210> SEQ ID NO 37
<211> LENGTH: 778
<212> TYPE: DNA
<213> ORGANISM: mus musculus
<220> FEATURE:
<221> NAME/KEY: CDS
<222> LOCATION: (47)...(583)

<400> SEQUENCE: 37
```

| | | | | | |
|---|---|---|---|---|---|
| aggctctcct ctcacttatc aactgttgac acttgtgcga tcggtg atg gct gtc | | | | | 55 |
| | | | | Met Ala Val | |
| | | | | 1 | |

| ctg cag aaa tct atg agt ttt tcc ctt atg ggg act ttg gcc gcc agc | 103 |
|---|---|
| Leu Gln Lys Ser Met Ser Phe Ser Leu Met Gly Thr Leu Ala Ala Ser | |
| 5                  10                  15 | |

| tgc ctg ctt ctc att gcc ctg tgg gcc cag gag gca aat gcg ctg ccc | 151 |
|---|---|
| Cys Leu Leu Leu Ile Ala Leu Trp Ala Gln Glu Ala Asn Ala Leu Pro | |
| 20                  25                  30                  35 | |

| gtc aac acc cgg tgc aag ctt gag gtg tcc aac ttc cag cag ccg tac | 199 |
|---|---|
| Val Asn Thr Arg Cys Lys Leu Glu Val Ser Asn Phe Gln Gln Pro Tyr | |
|         40                  45                  50 | |

| atc gtc aac cgc acc ttt atg ctg gcc aag gag gcc agc ctt gca gat | 247 |
|---|---|
| Ile Val Asn Arg Thr Phe Met Leu Ala Lys Glu Ala Ser Leu Ala Asp | |
|         55                  60                  65 | |

| aac aac aca gat gtc cgg ctc atc ggg gag aaa ctg ttc cga gga gtc | 295 |
|---|---|
| Asn Asn Thr Asp Val Arg Leu Ile Gly Glu Lys Leu Phe Arg Gly Val | |
|         70                  75                  80 | |

| aat gct aag gat cag tgc tac ctg atg aag cag gtg ctc aac ttc acc | 343 |
|---|---|
| Asn Ala Lys Asp Gln Cys Tyr Leu Met Lys Gln Val Leu Asn Phe Thr | |
| 85                  90                  95 | |

| ctg gaa gac gtt ctg ctc ccc cag tca gac agg ttc cag ccc tac atg | 391 |
|---|---|
| Leu Glu Asp Val Leu Leu Pro Gln Ser Asp Arg Phe Gln Pro Tyr Met | |
| 100                 105                 110                 115 | |

| cag gag gtg gtg cct ttc ctg acc aaa ctc agc aat cag ctc agc tcc | 439 |
|---|---|
| Gln Glu Val Val Pro Phe Leu Thr Lys Leu Ser Asn Gln Leu Ser Ser | |
|         120                 125                 130 | |

| tgt cac atc agc ggt gac gac cag aac atc cag aag aat gtc aga agg | 487 |
|---|---|
| Cys His Ile Ser Gly Asp Asp Gln Asn Ile Gln Lys Asn Val Arg Arg | |
|         135                 140                 145 | |

| ctg aag gag aca gtg aaa aag ctt gga gag agt gga gag atc aag gcg | 535 |
|---|---|
| Leu Lys Glu Thr Val Lys Lys Leu Gly Glu Ser Gly Glu Ile Lys Ala | |
|         150                 155                 160 | |

| att ggg gaa ctg gac ctg ctg ttt atg tct ctg aga aat gct tgc gtc | 583 |
|---|---|
| Ile Gly Glu Leu Asp Leu Leu Phe Met Ser Leu Arg Asn Ala Cys Val | |
|         165                 170                 175 | |

| tgagcgagaa gaagctagaa aacgaagaac tgctccttcc tgccttctaa aaagaacaat | 643 |
|---|---|
| aagatccctg aatggacttt tttactaaag gaaagtgaga agctaacgtc catcatcatt | 703 |
| agaagatttc acatgaaacc tggctcagtt gaaaagaaa atagtgtcaa gttgtccatg | 763 |
| agaccagagg tagac | 778 |

```
<210> SEQ ID NO 38
```

```
<211> LENGTH: 179
<212> TYPE: PRT
<213> ORGANISM: mus musculus

<400> SEQUENCE: 38

Met Ala Val Leu Gln Lys Ser Met Ser Phe Ser Leu Met Gly Thr Leu
 1               5                  10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Asn Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide primer ZC37125

<400> SEQUENCE: 39
ctatttggcc ggccaccatg gctgtcctgc ag                                    32

<210> SEQ ID NO 40
<211> LENGTH: 32
<212> TYPE: DNA
<213> ORGANISM: Artificial Sequence
<220> FEATURE:
<223> OTHER INFORMATION: Oligonucleotide primer ZC37126

<400> SEQUENCE: 40
cgtacgggcg cgcctcagac gcaagcattt ct                                    32

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide primer ZC28348

<400> SEQUENCE: 41
cgggatcccg atggccgccc tgcag                                            25

<210> SEQ ID NO 42
<211> LENGTH: 28
```

```
<212> TYPE: DNA
<213> ORGANISM: Artificial Sequence
<220> FEATURE:
<223> OTHER INFORMATION: Oligonucleotide primer ZC28345

<400> SEQUENCE: 42
gctctagacc aatgcaggca tttctcag                                          28

<210> SEQ ID NO 43
<211> LENGTH: 17
<212> TYPE: DNA
<213> ORGANISM: Artificial Sequence
<220> FEATURE:
<223> OTHER INFORMATION: Oligonucleotide primer ZC447

<400> SEQUENCE: 43
taacaatttc acacagg                                                      17

<210> SEQ ID NO 44
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 44
cgttgtaaaa cgacggcc                                                     18

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide primer ZC39289

<400> SEQUENCE: 45
tccgaggagt caatgctaag                                                   20

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide primer ZC39290

<400> SEQUENCE: 46
tccaagcttt ttcactgtct                                                   20

<210> SEQ ID NO 47
<211> LENGTH: 684
<212> TYPE: DNA
<213> ORGANISM: Homo sapiens

<400> SEQUENCE: 47
atgaggacgc tgctgaccat cttgactgtg ggatccctgg ctgctcacgc ccctgaggac        60
ccctcggatc tgctccagca cgtgaaattc cagtccagca actttgaaaa catcctgacg       120
tgggacagcg ggccagaggg cacccccagac acgtctacta gcatcgagta taagacgtac       180
ggagagaggg actgggtggc aaagaagggc tgtcagcgga tcacccggaa gtcctgcaac       240
ctgacggtgg agacgggcaa cctcacggag ctctactatg ccagggtcac cgctgtcagt       300
gcgggaggcc ggtcagccac caagatgact gacaggttca gctctctgca gcacactacc       360
ctcaagccac tgatgtgac ctgtatctcc aaagtgagat cgattcagat gattgttcat       420
cctaccccca cgccaatccg tgcaggcgat ggccaccggc taaccctgga agacatcttc       480
```

-continued

```
catgacctgt tctaccactt agagctccag gtcaaccgca cctaccaaat gcaccttgga    540
gggaagcaga gagaatatga gttcttcggc ctgaccctg acacagagtt ccttggcacc    600
atcatgattt gcgttcccac ctgggccaag gagagtgccc cctacatgtg ccgagtgaag    660
acactgccag accggacatg gacc                                           684

<210> SEQ ID NO 48
<211> LENGTH: 660
<212> TYPE: DNA
<213> ORGANISM: Homo sapiens

<400> SEQUENCE: 48
atggcgtgga gtcttgggag ctggctgggt ggctgcctgc tggtgtcagc attgggaatg     60
gtaccacctc ccgaaaatgt cagaatgaat tctgttaatt tcaagaacat tctacagtgg    120
gagtcacctg cttttgccaa agggaacctg actttcacag ctcagtacct aagttatagg    180
atattccaag ataaatgcat gaatactacc ttgacgaat gtgatttctc aagtctttcc    240
aagtatggtg accacacctt gagagtcagg gctgaatttg cagatgagca ttcagactgg    300
gtaaacatca ccttctgtcc tgtggatgac accattattg acccctggaa atgcaagta    360 gaagtacttg atgattcttt acatatgcgt ttcttagccc ctaaaattga gaatgaatac    420
gaaacttgga ctatgaagaa tgtgtataac tcatggactt ataatgtgca atactggaaa    480
aacggtactg atgaaaagtt tcaaattact ccccagtatg actttgaggt cctcagaaac    540
ctggagccat ggacaactta ttgtgttcaa gttcgagggt ttcttcctga tcggaacaaa    600 gctgggaat ggagtgagcc tgtctgtgag caaacaaccc atgacgaaac ggtcccctcc    660

<210> SEQ ID NO 49
<211> LENGTH: 8
<212> TYPE: PRT
<213> ORGANISM: Artificial Sequence
<220> FEATURE:
<223> OTHER INFORMATION: Gly-Ser peptide spacer of 8 amino acids

<400> SEQUENCE: 49

Gly Ser Gly Ser Gly Ser Gly Ser
 1               5

<210> SEQ ID NO 50
<211> LENGTH: 70
<212> TYPE: DNA
<213> ORGANISM: Artificial Sequence
<220> FEATURE:
<223> OTHER INFORMATION: Oligonucleotide primer ZC39335

<400> SEQUENCE: 50
atcggaattc gcagaagcca tgaggacgct gctgaccatc ttgactgtgg ggtccctggc     60
tgctcacgcc                                                           70

<210> SEQ ID NO 51
<211> LENGTH: 31
<212> TYPE: DNA
<213> ORGANISM: Artificial Sequence
<220> FEATURE:
<223> OTHER INFORMATION: Oligonucleotide primer ZC39434

<400> SEQUENCE: 51
cagtggatcc tggcagtgtc ttcactcggc a                                   31

<210> SEQ ID NO 52
```

<211> LENGTH: 37
<212> TYPE: DNA
<213> ORGANISM: Artificial Sequence
<220> FEATURE:
<223> OTHER INFORMATION: Oligonucleotide primer ZC39319

<400> SEQUENCE: 52
atcggaattc gcagaagcca tggcgtggag ccttggg        37

<210> SEQ ID NO 53
<211> LENGTH: 28
<212> TYPE: DNA
<213> ORGANISM: Artificial Sequence
<220> FEATURE:
<223> OTHER INFORMATION: Oligonucleotide primer ZC39325

<400> SEQUENCE: 53
cagtggatcc ggaggggacc gtttcgtc        28

<210> SEQ ID NO 54
<211> LENGTH: 16
<212> TYPE: DNA
<213> ORGANISM: Artificial Sequence
<220> FEATURE:
<223> OTHER INFORMATION: Oligonucleotide primer ZC39776

<400> SEQUENCE: 54
gggcccgcta gcacct        16

<210> SEQ ID NO 55
<211> LENGTH: 16
<212> TYPE: DNA
<213> ORGANISM: Artificial Sequence
<220> FEATURE:
<223> OTHER INFORMATION: Oligonucleotide primer ZC39777

<400> SEQUENCE: 55
gggtgatccg ctggca        16

<210> SEQ ID NO 56
<211> LENGTH: 36
<212> TYPE: DNA
<213> ORGANISM: Artificial Sequence
<220> FEATURE:
<223> OTHER INFORMATION: Oligonucleotide primer ZC38752

<400> SEQUENCE: 56
ccagccactt tctctctccg tatttcttat attcca        36

<210> SEQ ID NO 57
<211> LENGTH: 39
<212> TYPE: DNA
<213> ORGANISM: Artificial Sequence
<220> FEATURE:
<223> OTHER INFORMATION: Oligonucleotide primer ZC40940

<400> SEQUENCE: 57
ttggtccctc gtggaagcac tcagtcaacg catgagtct        39

<210> SEQ ID NO 58
<211> LENGTH: 39
<212> TYPE: DNA
<213> ORGANISM: Artificial Sequence
<220> FEATURE:
<223> OTHER INFORMATION: Oligonucleotide primer ZC40943

<400> SEQUENCE: 58

```
atgcattcta gatcatggaa tttccacaca tctctcttc                              39
```

<210> SEQ ID NO 59
<211> LENGTH: 57
<212> TYPE: DNA
<213> ORGANISM: Artificial Sequence
<220> FEATURE:
<223> OTHER INFORMATION: Oligonucleotide primer ZC40942

<400> SEQUENCE: 59

```
atgcattccg agattataa ggatgatgat gataagttgg tccctcgtgg aagcact        57
```

<210> SEQ ID NO 60
<211> LENGTH: 10
<212> TYPE: PRT
<213> ORGANISM: Artificial Sequence
<220> FEATURE:
<223> OTHER INFORMATION: Glu-Glu (CEE) Tag amino acid sequence with
      spacer

<400> SEQUENCE: 60

```
Gly Ser Gly Gly Glu Tyr Met Pro Met Glu
1               5                   10
```

<210> SEQ ID NO 61
<211> LENGTH: 10
<212> TYPE: PRT
<213> ORGANISM: Artificial Sequence
<220> FEATURE:
<223> OTHER INFORMATION: C-terminal HIS peptide tag, with spacer

<400> SEQUENCE: 61

```
Gly Ser Gly Gly His His His His His His
1               5                   10
```

<210> SEQ ID NO 62
<211> LENGTH: 484
<212> TYPE: PRT
<213> ORGANISM: Artificial Sequence
<220> FEATURE:
<223> OTHER INFORMATION: Fusion polypeptide hzcytor11/Fc4-CEE

<400> SEQUENCE: 62

```
Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
                20                  25                  30

Ser Asn Phe Glu Asn Ile Leu Thr Trp Asp Ser Gly Pro Glu Gly Thr
            35                  40                  45

Pro Asp Thr Val Tyr Ser Ile Glu Tyr Lys Thr Tyr Gly Glu Arg Asp
        50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
                100                 105                 110

Phe Ser Ser Leu Gln His Thr Thr Leu Lys Pro Pro Asp Val Thr Cys
            115                 120                 125

Ile Ser Lys Val Arg Ser Ile Gln Met Ile Val His Pro Thr Pro Thr
        130                 135                 140

Pro Ile Arg Ala Gly Asp Gly His Arg Leu Thr Leu Glu Asp Ile Phe
145                 150                 155                 160
```

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Gly Ser Gly Ser Gly Ser Glu Pro Arg Ser
225                 230                 235                 240

Ser Asp Lys Thr His Thr Cys Pro Pro Cys Pro Ala Pro Glu Ala Glu
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Leu Val Pro Arg Gly Ser Gly Ser Gly Gly Glu Tyr
465                 470                 475                 480

Met Pro Met Glu

<210> SEQ ID NO 63
<211> LENGTH: 476
<212> TYPE: PRT
<213> ORGANISM: Artificial Sequence
<220> FEATURE:
<223> OTHER INFORMATION: Fusion polypeptide hCRF2-4/Fc4-CHIS

<400> SEQUENCE: 63

Met Ala Trp Ser Leu Gly Ser Trp Leu Gly Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly

```
                   35                  40                  45
Asn Leu Thr Phe Thr Ala Gln Tyr Leu Ser Tyr Arg Ile Phe Gln Asp
 50                  55                  60
Lys Cys Met Asn Thr Thr Leu Thr Glu Cys Asp Phe Ser Ser Leu Ser
 65                  70                  75                  80
Lys Tyr Gly Asp His Thr Leu Arg Val Arg Ala Glu Phe Ala Asp Glu
                 85                  90                  95
His Ser Asp Trp Val Asn Ile Thr Phe Cys Pro Val Asp Asp Thr Ile
                100                 105                 110
Ile Gly Pro Pro Gly Met Gln Val Glu Val Leu Asp Asp Ser Leu His
                115                 120                 125
Met Arg Phe Leu Ala Pro Lys Ile Glu Asn Glu Tyr Glu Thr Trp Thr
                130                 135                 140
Met Lys Asn Val Tyr Asn Ser Trp Thr Tyr Asn Val Gln Tyr Trp Lys
145                 150                 155                 160
Asn Gly Thr Asp Glu Lys Phe Gln Ile Thr Pro Gln Tyr Asp Phe Glu
                165                 170                 175
Val Leu Arg Asn Leu Glu Pro Trp Thr Thr Tyr Cys Val Gln Val Arg
                180                 185                 190
Gly Phe Leu Pro Asp Arg Asn Lys Ala Gly Glu Trp Ser Glu Pro Val
                195                 200                 205
Cys Glu Gln Thr Thr His Asp Glu Thr Val Pro Ser Gly Ser Gly Ser
                210                 215                 220
Gly Ser Gly Ser Glu Pro Arg Ser Ser Asp Lys Thr His Thr Cys Pro
225                 230                 235                 240
Pro Cys Pro Ala Pro Glu Ala Glu Gly Ala Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Lys Phe
                275                 280                 285
Asn Trp Tyr Val Asp Gly Val Glu Val His Asn Ala Lys Thr Lys Pro
290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Ala Leu Pro Ser Ser Ile Glu Lys Thr Ile Ser Lys Ala
                340                 345                 350
Lys Gly Gln Pro Arg Glu Pro Gln Val Tyr Thr Leu Pro Pro Ser Arg
                355                 360                 365
Asp Glu Leu Thr Lys Asn Gln Val Ser Leu Thr Cys Leu Val Lys Gly
                370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
                420                 425                 430
Gly Asn Val Phe Ser Cys Ser Val Met His Glu Ala Leu His Asn His
                435                 440                 445
Tyr Thr Gln Lys Ser Leu Ser Leu Ser Pro Gly Lys Leu Val Pro Arg
                450                 455                 460
```

-continued

```
Gly Ser Gly Ser Gly Gly His His His His His
465                 470             475

<210> SEQ ID NO 64
<211> LENGTH: 699
<212> TYPE: DNA
<213> ORGANISM: Homo sapiens

<400> SEQUENCE: 64
gagcccagat cttcagacaa aactcacaca tgcccaccgt gcccagcacc tgaagccgag      60
ggggcaccgt cagtcttcct cttccccca aaacccaagg acaccctcat gatctcccgg     120 accctgagg tcacatgcgt ggtggtggac gtgagccacg aagaccctga ggtcaagttc     180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc catcctccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaataa                           699

<210> SEQ ID NO 65
<211> LENGTH: 16
<212> TYPE: DNA
<213> ORGANISM: Artificial Sequence
<220> FEATURE:
<223> OTHER INFORMATION: TaqMan forward primer ZC42459

<400> SEQUENCE: 65
tggccaggct cagcaa                                                     16

<210> SEQ ID NO 66
<211> LENGTH: 21
<212> TYPE: DNA
<213> ORGANISM: Artificial Sequence
<220> FEATURE:
<223> OTHER INFORMATION: TaqMan reverse primer ZC42458

<400> SEQUENCE: 66
gcacattcct ctggatatgc a                                               21

<210> SEQ ID NO 67
<211> LENGTH: 31
<212> TYPE: DNA
<213> ORGANISM: Artificial Sequence
<220> FEATURE:
<223> OTHER INFORMATION: TaqMan probe ZC42460

<400> SEQUENCE: 67
aggctaagca catgtcatat tgaaggtgat g                                    31
```